US010647985B2

(12) United States Patent
Collin et al.

(10) Patent No.: US 10,647,985 B2
(45) **Date of Patent: *May 12, 2020**

(54) ANTISENSE OLIGONUCLEOTIDES FOR THE TREATMENT OF LEBER CONGENITAL AMAUROSIS

(71) Applicant: STICHTING KATHOLIEKE UNIVERSITEIT, Nijmegen (NL)

(72) Inventors: Robert Wilhelmus Johanna Collin, Venlo (NL); Franciscus Peter Maria Cremers, Malden (NL); Antonia Ingrid Den Hollander, Groesbeek (NL)

(73) Assignee: STICHTING KATHOLIEKE UNIVERSITEIT, Nijmegen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/197,865

(22) Filed: Nov. 21, 2018

(65) Prior Publication Data

US 2019/0078091 A1 Mar. 14, 2019

Related U.S. Application Data

(63) Continuation of application No. 15/963,229, filed on Apr. 26, 2018, now Pat. No. 10,167,470, which is a continuation of application No. 15/656,635, filed on Jul. 21, 2017, now abandoned, which is a continuation of application No. 14/342,776, filed as application No. PCT/NL2012/050275 on Apr. 25, 2012, now Pat. No. 9,771,580.

(60) Provisional application No. 61/531,137, filed on Sep. 6, 2011.

(30) Foreign Application Priority Data

Sep. 5, 2011 (NL) ..................................... 2007351

(51) Int. Cl.
*C12N 15/113* (2010.01)

(52) U.S. Cl.
CPC ........ *C12N 15/113* (2013.01); *C12N 2310/11* (2013.01); *C12N 2310/15* (2013.01); *C12N 2310/321* (2013.01); *C12N 2310/346* (2013.01); *C12N 2320/33* (2013.01); *C12N 2320/34* (2013.01)

(58) Field of Classification Search
CPC combination set(s) only.
See application file for complete search history.

(56) References Cited

U.S. PATENT DOCUMENTS 6,875,736 B2 4/2005 Rana
7,517,644 B1 4/2009 Smith
9,487,782 B2 11/2016 Rozet et al.
2005/0118625 A1 6/2005 Mounts
2005/0233455 A1 10/2005 Damha et al.
2009/0269755 A1 10/2009 Aartsma-Rus et al.
2012/0108654 A1 5/2012 Campochiaro

FOREIGN PATENT DOCUMENTS

EP 1619249 1/2006
WO WO 2002024906 3/2002
WO WO 2009/121536 10/2009
WO WO 2012/168435 12/2012

OTHER PUBLICATIONS

Jahns, et al. (2015) "Stereochemical bias introduced during RNA synthesis modulates the activity of phosphorothioate siRNAs." Nature Communications, vol. 6:6317. (Year: 2015).*

Baala et al, "Pleiotropic effects of CEP290 (NPHP6) mutations extend to Meckel syndrome", Am. J. Hum. Genet., 2007, 81:170-179.

Bainbridge, et al. "Effect of gene therapy on visual function in Leber's congenital amaurosis," N. Engl. J. Med., 2008, 358:2231-2239.

Baye, "Then-Terminal Region of Centrosomal Protein 290 (CEP290) Restores Vision in a Zebrafish Model of Human Blindness", Human Molecular Genetics, Apr. 2011, vol. 20, No. 8, pp. 1467-1477.

Cideciyan et al., "Centrosomai-Ciliary Gene CEP290/NPHP6 Mutations Result in Blindness with Unexpected Sparing of Photoreceptors and Visual Brain: Implications for Therapy of Leber Congenital Amaurosis", Human Mutation, Nov. 2007, vol. 28, No. 11, pp. 1074-1083.

Cideciyan, et al. "Human gene therapy for RPE65 isomerase deficiency activates the retinoid cycle of vision but with slow rod kinetics", Proc Nati Aead Sci, 2008, vol. 105, 15112-15117.

Collin et al, "Antisense Oligonucleotide (AON-based Therapy for CEP290-Associated LCA", ARVO, May 3, 2011.

Collin et al., "Antisense oligonucleotide (AON)-based therapy for CEP290-associated LCA." Poster presented at: ARVO Annual Meeting, May 3, 2011, Program No. 3324, Poster No. A572.

Coppieters, et al. "Genetic screening, of LCA in Belgium: predominance of CEP290 and identification of potential modifier alleles in AH 11 of CEP290-related phenotypes", Hum Mutat, 2010, 31:E1709-E1766.

Estrada-Cuzcano, et al. "IQCB1 mutations in patients with leber congenital amaurosis", Invest Ophthalmol Vis Sci, 2011, vol. 52, 834-839.

Franchi et al., "Identification of 4370 expressed sequence tags from a 3'-end-specific cDNA library of human skeletal muscle by DNA sequencing and filter hybridization", Genome Research, 1996, vol. 6.1, pp. 35-42.

Gerard et al, "Antisense Oligonucleotide-Mediated Exon Skipping Restores Primary Cilia Assembly in Fibroblasts Harbouring the Common LCA CEP290 C.2991+1655g>A Mutation", Investigative Ophthalmology & Visual Science, Mar. 2012, 1920-1920.

(Continued)

*Primary Examiner* — Jennifer Pitrak McDonald
(74) *Attorney, Agent, or Firm* — Fish & Richardson P.C.

(57) ABSTRACT

The present invention relates to the fields of medicine and immunology. In particular, it relates to novel antisense oligonucleotides that may be used in the treatment, prevention and/or delay of Leber congenital amaurosis.

14 Claims, 5 Drawing Sheets

Specification includes a Sequence Listing.

(56) References Cited

OTHER PUBLICATIONS

Gerard et al., "AON-Mediated Exon Skipping Restores Ciliation in Fibroblasts Harboring the Common Leber Congenital Amaurosis CEP290 Mutation", American Society of Gene & Cell Therapy, Molecular Therapy-Nucleic Acids, Jun. 26, 2012, vol. 1, e29.
Hauswirth, et al. "Phase I Trial of Leber Congenital Amaurosis due to Estrada-Mutations by OcularSubretina Injection of Adena-Associated Virus Gene Vector: Short-Term Results," Hum Gene Ther, Oct. 2008, vol. 19, pp. 979-990.
Helou, et al. "Mutation analysis of NPHP6/CEP290 in patients with Joubert syndrome and Senior-Loken syndrome", U Med Genet. 2007, vol. 44, 657-663.
Hollander et al., "Mutations in the CEP290 (NPHP6) Gene are a Frequent Cause of Leber Congenital amaurosis,"American Journal of Human Genetics, American Society of Human Genetics, Sep. 2006, vol. 79, No. 3, pp. 556-561.
Hollander, et al. "Leber congenital amaurosis: genes, proteins and disease mechanisms," Prog Retin Eve Res, 2008, vol. 27:391-419.
Hollander, et al. "Lighting a candle in the dark: advances in genetics and gene therapy of recessive retinal dystrophies", J Clin Invest, 2010, vol. 120, 3042-3053.
International Search Report in PCT/NL2012/050275 dated Aug. 28, 2012.
Koenekoop, et al. "Genetic testing for retinal dystrophies and dysfunctions: benefits, dilemmas and solutions", Clin Experiment Ophthalmol, 2007, vol. 35, 473-485.
Leber "Uber Retinitis Pigmentosa and angeborene Amaurose" van Graefe's Archives Ophthalmology(1869) vol. 15, pp. 1-25.
Littink, et al. "A novel nonsense mutation in CEP290 induces exon skipping and leads to a relatively mild retinal Phenotype", Invest Ophthalmol Vis Sci, 2010, Vo. 51, 3646-3652.
Maguire, et al. "Age-dependent effects of RPE65 gene therapy for Leber's congenital amaurosis: a phase 1 doseescalation trial", Lancet, 2009, vol. 374, 1597-1605.
Maguire. et al. "Safety and efficacy of gene transfer for Leber's congenital amaurosis,"N Engl J Med, 2008, vol. 358, 2240-2248.
Perraul T, et al. "Spectrum of NPHP6/CEP290 mutations in Leber congenital amaurosis and delineation of the associated phenotype", Hum Mutat, 2007, vol. 28:416-416.
Stone "Leber congenital amaurosis—a model for efficient testing of heterogeneous disorders: LXIV Edward Jackson Memorial Lecture", Am J Ophthalmol, 2007, vol. 144, 791-811.
Valente, et al. "Mutations in CEP290, which encodes a centrosomal protein, cause pleiotropic forms of Joubert syndrome", Nat Genet, 2006, vol. 38, 623-625.
Aartsma-Rus, et al., "Exonic sequences provide better targets for antisense oligonucleotides than splice site sequences in the modulation of Duchenne muscular dystrophy splicing," Oligonucleotides, 2008, 20:69-77.
Aartsma-Rus, et al., "Guidelines for antisense oligonucleotide design and insight into splice-modulating mechanisms," Mol. Ther., 2008, 548-553.
Alloca, et al., "Novel adeno-associated virus serotypes efficiently transduce murine photoreceptors." J. Virol., 2007, 81:11372-11380.
Coppieters, et al., "CEP290, a gene with many faces: mutation overview and presentation of CEP290base," Hum. Mutat., 2010, 31:1097-1108.
Dorn and Kippenberger. "Clinical application of CpG−, non-CpG−, and antisense oligodeoxynucleotides as immunomodulators," Curr. Opin. Mol. Ther., 2008, 10(1):10-20.
Egholm, et al., "PNA hybridizes to comlementary oligonucleotides obeying the Watson-Crick hydrogen-bonding rules," Nature, 1993, 365:566-568.
Frank, et al., "Mutations of the CEP290 gene encoding a centrosomal protein cause Meckel-Gruber syndrome," Hum. Mutat., 2008, 29:45-52.
Friesen and Darby, "Specific RNA binding proteins constructed from zinc fingers," Nature Structural Biology, 1998, 5:543-546.
Geib and Hertel. "Restoration of full-length SMN promoted by adenoviral vectors expressiong RNA antisense oligonucleotides embedded in U7 snRNAs." PLoS One, 2009, e8204.
Gorman, et al., "Stable alteration of pre-mRNA splicing patterns by modified U7 small nuclear RNAs," Proc. Natl. Acad. Sci. USA, 1998, 95(91:4929-34.
Govindaraju and Kumar, "Backbone-extended pyrrolidine peptide nucleic acids (bepPNA): design, synthesis and DNA/RNA binding studies." Chem. Commun., 2005, 495-497.
Goyenhalle, et al., "Rescue of dystrophic muscle through U7 snRNA-mediated exon skipping," Science, 2004, 306:1796-1799.
Hammond, et al., "Genetic therapies for RNA mis-splicing diseases," Trends Genet., 2011, 27:196-205.
Kinali, et al., "Local restoration of dystrophin expression with the morpholino oligomer AVI-4658 in Duchenne muscular dystrophy: a single-clind, placebo-controlled, dose-escalation, proof-of-concept study," Lancet Neurol., 2009, 8:918-928.
Lebherz, et al., "Novel AAV serotypes for improved ocular gene transfer," J. Gene Med., 2008, 10:375-382.
Li, et al., "Gene therapy following subretinal AAV5 vector delivery is not affected by a previous intravitreal AAV5 vector administration in the partner eye," Mol. Vis., 2009, 15:267-275.
Morita, et al., "2'-O, 4'C-Ethylene-bridged nucleic acids (ENA) with nuclease-resistance and high affinity for RNA," Nucleic Acid Res., 2001, Suppl. 1: 241-242.
Nielsen, et al., "Sequence-selective recognition of DNA by strand displacement with a thymine-substituted polyamide," Science, 1991, 254:1497-1500.
Schmid and Jelinek, "The Alu family of dispersed repetitive sequences," Science. 1982, 216:1065-1070.
Simonelli, et al., "Gene therapy for Leber's congenital amaurosis is safe and effective through 1.5 years after vetor administration," Mol. Ther., 2009, 18:643-650.
Smith, et al., "An increased specificity score matrix for the prediction of SF2/ASF-specific exonic splicing enhancers," Hum. Mol. Genet., 2006, 15:2490-2508.
Suter, et al., Double-target antisense U7 snRNAs promote efficient skipping of an aberrant exon in three human beta-thalassemic mutations, hum. Mol. Genet., 1999, 8(13):2415-23.
Van Deutekom, et al., "Local dystrophin restoration with antisense oligonucleotide PRO051," N. Engl. J. Med., 2007, N. Engl. J. Med., 357:2677-2686.
Vandenberghe, et al., "Dosage thresholds for AAV2 and AAV8 photoreceptor gene therapy in monkey," Sci. Transl. Med., 2011, 3:88ra54.

* cited by examiner

A Wild-type *CEP290*

B LCA mutant *CEP290*

C LCA mutant *CEP290* + AON

ANTISENSE OLIGONUCLEOTIDES FOR THE TREATMENT OF LEBER CONGENITAL AMAUROSIS

CROSS-REFERENCE TO RELATED APPLICATIONS

The present application is a Continuation Application of U.S. application Ser. No. 15/963,229, filed Apr. 26, 2018, which is a Continuation Application of U.S. application Ser. No. 15/656,635, filed Jun. 21, 2017, which is a Continuation Application of U.S. application Ser. No. 14/342,776, filed Jun. 16, 2014, which is the U.S. National Phase of International Patent Application No. PCT/NL2012/050275, filed Apr. 25, 2012 and published as WO 2013/036105 AI, which claims priority to Netherlands Patent Application No. 2007351, filed Sep. 5, 2011, and U.S. Provisional Application No. 61/531,137, filed Sep. 6, 2011. The contents of these applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Jul. 17, 2017, is named 069818-9676SequenceListing.txt and is 229 KB.

FIELD OF THE INVENTION

The present invention relates to the fields of medicine and immunology. In particular, it relates to novel antisense oligonucleotides that may be used in the treatment, prevention and/or delay of Leber congenital amaurosis.

BACKGROUND OF THE INVENTION

Leber congenital amaurosis (LCA) is the most severe form of inherited retinal dystrophy, with an onset of disease symptoms in the first years of life (Leber, T., 1869) and an estimated prevalence of approximately 1 in 50,000 worldwide (Koenekoop et al, 2007; Stone, 2007). Genetically, LCA is a heterogeneous disease, with fifteen genes identified to date in which mutations are causative for LCA (den Hollander et al, 2008; Estrada-Cuzcano et al, 2011). The most frequently mutated LCA gene is CEP290, accounting for ~15% of all cases (Stone, 2007; den Hollander, 2008; den Hollander, 2006; Perrault et al, 2007). Severe mutations in CEP290 have been reported to cause a spectrum of systemic diseases that, besides retinal dystrophy, are characterized by brain defects, kidney malformations, polydactyly and/or obesity (Baal et al, 2007; den Hollander et al, 2008; Helou et al, 2007; Valente et al, 2006). There is no clear-cut genotype-phenotype correlation between the combination of CEP290 mutations and the associated phenotypes, but patients with LCA and early-onset retinal dystrophy very often carry hypomorphic alleles (Stone, 2007; den Hollander et al, 2006; Perrault et al, 2007; Coppieters et al, 2010; Liitink et al 2010). The by far most frequently occurring hypomorphic CEP290 mutation, especially in European countries and in the US, is a change in intron 26 of CEP290 (c.2991+1655A>G) (Stone, 2007; den Hollander et al, 2006; Perrault et al, 2007; Liitink et al, 2010). This mutation creates a cryptic splice donor site in intron 26 which results in the inclusion of an aberrant exon of 128 bp in the mutant CEP290 mRNA, and inserts a premature stop codon (p.C998X) (see FIG. 1). Besides the mutant CEP290 mRNA, also the wild-type transcript that lacks the aberrant exon is still produced, explaining the hypomorphic nature of this mutation (Estrada-Cuzcano et al, 2011).

LCA, and other retinal dystrophies, for long have been considered incurable diseases. However, the first phase I/II clinical trials using gene augmentation therapy have lead to promising results in a selected group of adult LCA/RP patients with mutations in the RPE65 gene (Bainbridge et al, 2008; Cideciyan et al, 2008; Hauswirth et al, 2008; Maguire et al, 2008). Unilateral subretinal injections of adeno-associated viruses particles carrying constructs encoding the wild-type RPE65 cDNA were shown to be safe and moderately effective in some patients, without causing any adverse effects. In a follow-up study using adults and children, visual improvements were more sustained, especially in the children who all gained ambulatory vision (Maguire et al, 2009). Together, these studies have shown the potential to treat LCA, and thereby enormously boosted the development of therapeutic strategies for other genetic subtypes of retinal dystrophies (den Hollander et al, 2010). However, due to the tremendous variety in gene size, and technical limitations of the vehicles that are used to deliver therapeutic constructs, gene augmentation therapy may not be applicable to all genes. The RPE65 cDNA is for instance only 1.6 kb, whereas the CEP290 cDNA amounts to about 7.4 kb, thereby exceeding the cargo size of many available vectors, including the presently used adeno-associated vectors (AAV). In addition, using gene replacement therapy, it is hard to control the expression levels of the therapeutic gene which for some genes need to be tightly regulated. It is therefore an objective of the present invention to provide a convenient therapeutic strategy for the prevention, treatment or delay of Leber congenital amaurosis as caused by an intronic mutation in CEP290.

DETAILED DESCRIPTION OF THE INVENTION

Surprisingly, it has now been demonstrated that specific antisense oligonucleotides (AONs) are able to block the aberrant splicing of (CEP290 that is caused by the intronic LCA mutation.

Accordingly, in a first aspect the present invention provides an exon skipping molecule that binds to and/or is complementary to a polynucleotide with the nucleotide sequence as shown in SEQ ID NO: 6, preferably SEQ ID NO: 7, more preferably SEQ ID NO: 8, or a part thereof.

In all embodiments of the present invention, the terms “modulating splicing” and “exon skipping” are synonymous. In respect of CEP290, “modulating splicing” or “exon skipping” are to be construed as the exclusion of the aberrant 128 nucleotide exon (SEQ ID NO: 4) from the CEP290 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules The term pre-mRNA refers to a non-processed or partly processed precursor mRNA that is synthesized from a DNA template in the nucleus of a cell by transcription.

The term "antisense oligonucleotide" is understood to refer to a nucleotide sequence which is substantially complementary to a target nucleotide sequence in a pre-mRNA molecule, hrRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 6, 7 or 8 sequence, preferably in the context of the aberrant 128 nucleotide CEP290 exon (SEQ ID NO: 4) may be assessed via techniques known to the skilled person. A preferred technique is gel mobility shift assay as described in EP 1 619 249. In a preferred embodiment, an exon skipping molecule is said to bind to one of the specified sequences as soon as a binding of said molecule to a labeled sequence SEQ ID NO: 6, 7 or 8 is detectable in a gel mobility shift assay.

In all embodiments of the invention, an exon skipping molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 6, preferably SEQ ID NO: 7, more preferably SEQ ID NO: 8, or a part thereof as later defined herein.

The term "substantially complementary" used in the context of the present invention indicates that some mismatches in the antisense sequence are allowed as long as the functionality, i.e. inducing skipping of the aberrant 128 nucleotide CEP290 exon (SEQ ID NO: 4), is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The present invention provides a method for designing an exon skipping molecule, preferably an oligonucleotide able to induce skipping of the aberrant 128 nucleotide CEP290 exon (SEQ ID NO: 4). First, said oligonucleotide is selected to bind to one of SEQ ID NO: 6, 7 or 8 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity may be assessed by detecting the presence or an increasing amount of a neutralizing antibody or an antibody recognizing said oligonucleotide using a standard immunoassay.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 6, 7, or 8 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein preferably no CpG and/or wherein a more acceptable Tm and/or free energy are obtained by choosing a distinct sequence of CEP290 (including SEQ ID NO: 6, 7 or 8) to which the oligonucleotide is complementary. Alternatively, if an oligonucleotide complementary to a given stretch within SEQ ID NO: 6, 7 or 8, comprises a CpG, and/or does not have an acceptable Tm and/or free energy, the skilled person may improve any of these parameters by decreasing the length of the oligonucleotide, and/or by choosing a distinct stretch within any of SEQ ID NO: 6, 7 or 8 to which the oligonucleotide is complementary and/or by altering the chemistry of the oligonucleotide.

At any step of the method, an oligonucleotide of the invention is preferably an olignucleotide, which is still able to exhibit an acceptable level of functional activity. A functional activity of said oligonucleotide is preferably to induce the skipping of the aberrant 128 nucleotide CEP290 exon (SEQ ID NO: 4) to a certain extent, to provide an individual with a functional CEP290 protein and/or mRNA and/or at least in part decreasing the production of an aberrant CEP290 protein and/or mRNA. In a preferred embodiment, an oligonucleotide is said to induce skipping of the aberrant 128 nucleotide CEP290 exon (SEQ ID NO: 4), when the aberrant 128 nucleotide CEP290 exon (SEQ ID NO: 4) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferably, a nucleic acid molecule according to the invention, preferably an oligonucleotide, which comprises a sequence that is complementary or substantially complementary to a nucleotide sequence as shown in SEQ ID NO: 6, preferably SEQ ID NO: 7, more preferably SEQ ID NO: 8, or part thereof of CEP290 is such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an oligonucleotide according to the invention comprises or consists of a sequence that is complementary to part of SEQ ID NO: 6, 7 or 8. As an example, an oligonucleotide may comprise a sequence that is complementary to part of SEQ ID NO: 6, 7 or 8 and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an oligonucleotide is detectable. Optionally, said oligonucleotide may further be tested by transfection into retina cells of patients. Skipping of a targeted exon may be assessed by RT-PCR (as described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule.

An exon skipping molecule of the invention is preferably a nucleic acid molecule or nucleotide-based molecule, preferably an (antisense) oligonucleotide, which is complementary to a sequence selected from SEQ ID NO: 6, 7 and 8.

A preferred exon skipping molecule, according to the invention is a nucleic acid molecule comprising an antisense oligonucleotide which antisense oligonucleotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule of the invention is an antisense oligonucelotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule comprising or preferably consisting of an antisense oligonucleotide selected from the group consisting of: SEQ ID NO: 10, SEQ ID NO: 11, and SEQ ID NO: 12.

In a more preferred embodiment, the invention provides an exon skipping molecule comprising or preferably consisting of the antisense oligonucleotide SEQ ID NO: 10. It was found that this molecule is very efficient in modulating splicing of the aberrant 128 nucleotide CEP290 exon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 128 nucleotide CEP290 exon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 12. It was found that this molecule is very efficient in modulating splicing of the aberrant 128 nucleotide CEP290 exon. This preferred exon skipping molecule of the invention comprising SEQ ID NO: 12 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule according to the invention may contain one of more RNA residues, or one or more DNA residues, and/or one or more nucleotide analogues or equivalents, as will be further detailed herein below.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O—, S—, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-0,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 128 nucleotide exon of CEP290. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule according to the invention may be indirectly administrated using suitable means known in the art. When the exon skipping molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al, 1998 or Suter D et al, 1999).

The exon skipping molecule according to the invention, preferably an antisense oligonucleotide, may be delivered as such. However, the exon skipping molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of aberrant 128 nucleotide CEP290 exon.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constitutent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CE7P290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.1 and 20 mg/kg, preferably from 0.5 and 20 mg/kg.

A preferred exon skipping molecule according to the invention, is for the treatment of a CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congenital amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides the use of an exon skipping molecule according to the invention, or of a viral vector according to the invention, or a composition according to the invention for the preparation of a medicament, for the preparation of a medicament for treating a CEP290 related disease or condition requiring modulating splicing of CEP290 and for the preparation of a medicament for the prevention, treatment or delay of a CEP290 related disease or condition. A preferred CEP290 related disease or condition is Leber congenital amaurosis. Therefore in a further aspect, there is provided the use of an exon skipping molecule, viral vector or composition as defined herein for the preparation of a medicament, for the preparation of a medicament for treating a condition requiring modulating splicing of CEP290 and for the preparation of a medicament for the prevention, treatment or delay of a CEP290 related disease or condition. A preferred CEP290 related disease or condition is Leber congenital amaurosis. Each feature of said use has earlier been defined herein.

A treatment in a use or in a method according to the invention is at least one week, at least one month, at least several months, at least one year, at least 2, 3, 4, 5, 6 years or more. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the mutation of the patient, the number of exon skipping molecules (i.e. dose), the formulation of said molecule. The frequency may be ranged between at least once in two weeks, or three weeks or four weeks or five weeks or a longer time period.

Dose ranges of an exon skipping molecule, preferably an oligonucleotide according to the invention are preferably designed on the basis of rising dose studies in clinical trials (in vivo use) for which rigorous protocol requirements exist. An exon skipping molecule or an oligonucleotide as defined herein may be used at a dose which is ranged from 0.1 and 20 mg/kg, preferably from 0.5 and 20 mg/kg.

In a preferred embodiment, a concentration of an oligonucleotide as defined herein, which is ranged from 0.1 nM and 1 μM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nm. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1\times10^{9}$-$1\times10^{7}$ virus particles per injection, more preferably from $1\times10^{10}$-$1\times10^{12}$ virus particles per injection.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule according to the invention, or a viral vector according to the invention, or a composition according to the invention for use according to the invention may be suitable for administration to a cell, tissue and/or an organ in vivo of individuals already affected or at risk of developing a CEP290 related disease or condition, and may be administered in vivo, ex vivo or in vitro. Said exon skipping molecule according to the invention, or a viral vector according to the invention, or a composition according to the invention may be directly or indirectly administrated to a cell, tissue and/or an organ in vivo of an individual already affected by or at risk of developing a CEP290 related disease or condition, and may be administered directly or indirectly in vivo, ex vivo or in vitro. As Leber congenital amaurosis has a pronounced phenotype in retina cells, it is preferred that said cells are retina cells, it is further preferred that said tissue is the retina and/or it is further preferred that said organ comprises or consists of the eye.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vivo or in vitro.

The invention further provides a method for the treatment of a CEP290 related disease or condition requiring modulating splicing of CEP290 of an individual in need thereof, said method comprising contacting a cell, preferably a retina cell, of said individual with an exon skipping molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro. A preferred CEP290 related disease or condition is Leber congenital amaurosis.

Unless otherwise indicated each embodiment as described herein may be combined with another embodiment as described herein.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function. This experiment is presently ongoing.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO: 1 containing the nucleic acid sequence coding for the polypeptide should prevail.

All patent and literature references cited in the present specification are hereby incorporated by reference in their entirety.

A) Normal CEP290 mRNA splicing of exons 26 and 27, resulting in wild-type CEP290 protein(figure discloses SEQ ID NOS 17-18, respectively, in order of appearance).

B) The most frequent LCA-causing mutation is an A-to-G transition (underlined and indicated with an asterisk) in intron 26 of CEP290. This mutation creates a splice donor site, which results in the inclusion of an aberrant exon to ~50% of the CEP290 mRNA and subsequent premature termination of the CEP290 protein (figure discloses SEQ ID NOS 19-20, respectively, in order of appearance).

C) Upon binding of sequence-specific AONs, factors involved in splicing will not recognize the aberrant splice donor site in intron 26, resulting in redirection of normal CEP290 splicing and synthesis of a correct CEP290 protein (figure discloses SEQ ID NOS 19, 21, and 20, respectively, in order of appearance).

Figure 2A:
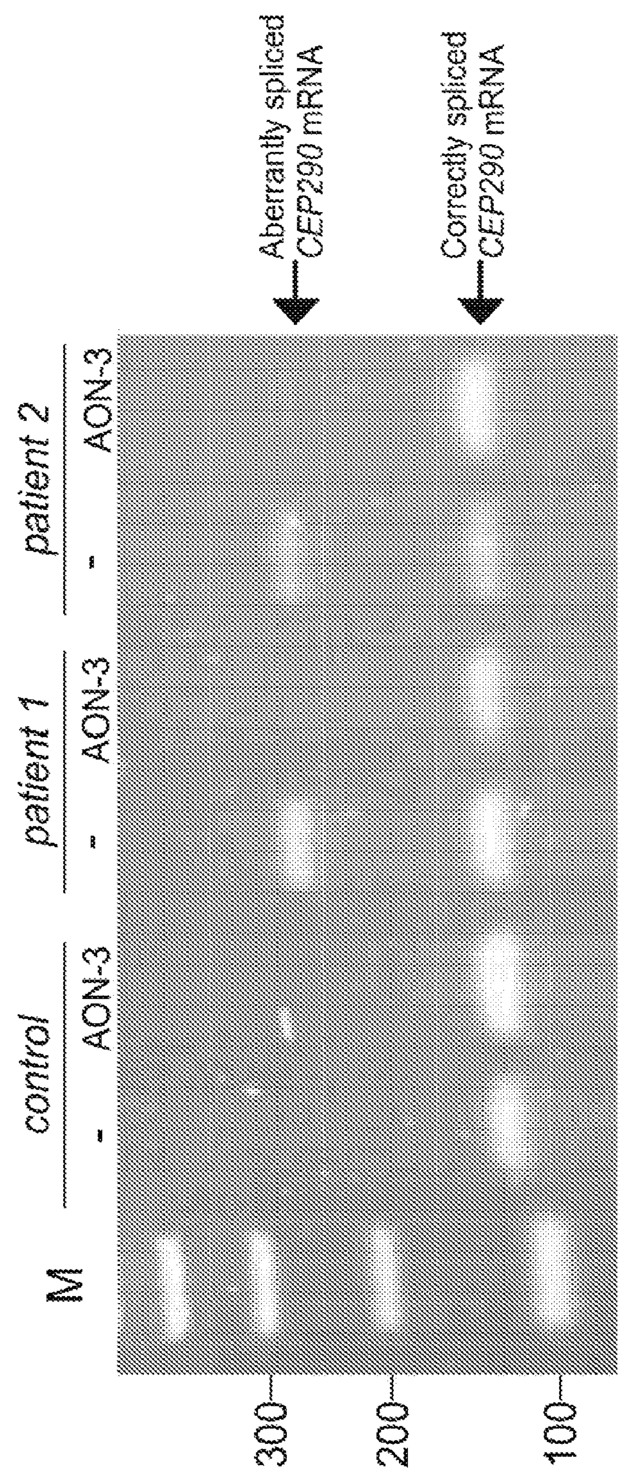
Figure 2B:
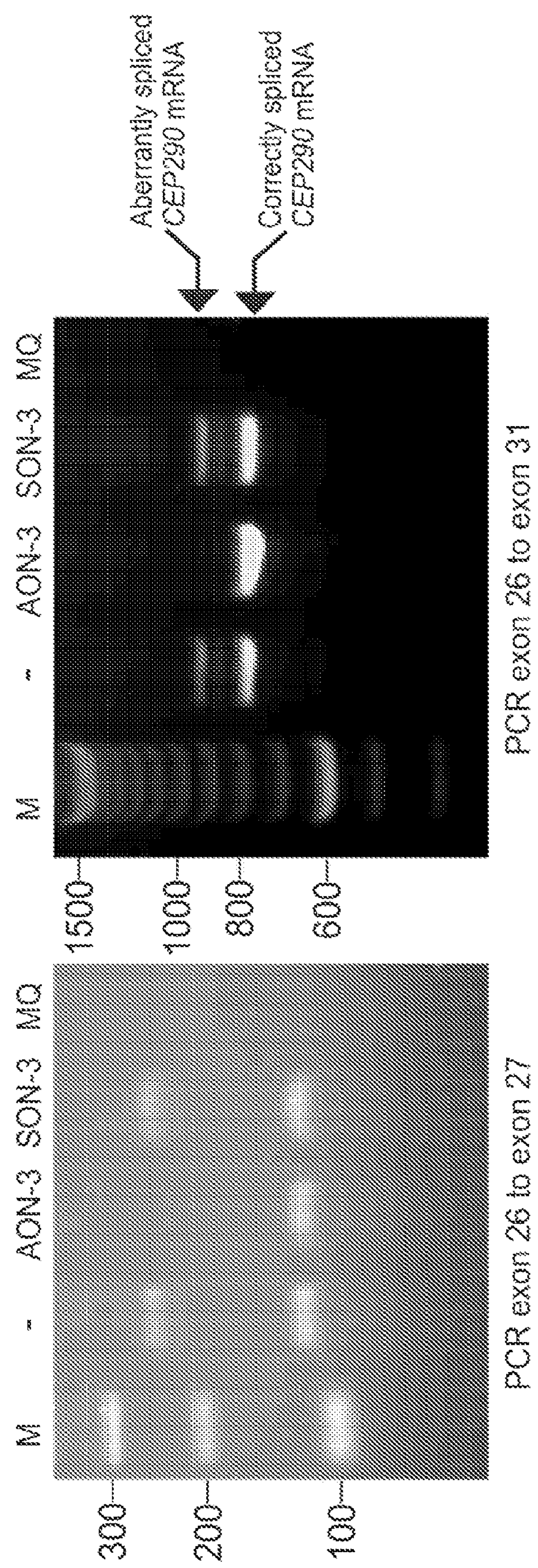
Figure 2C:
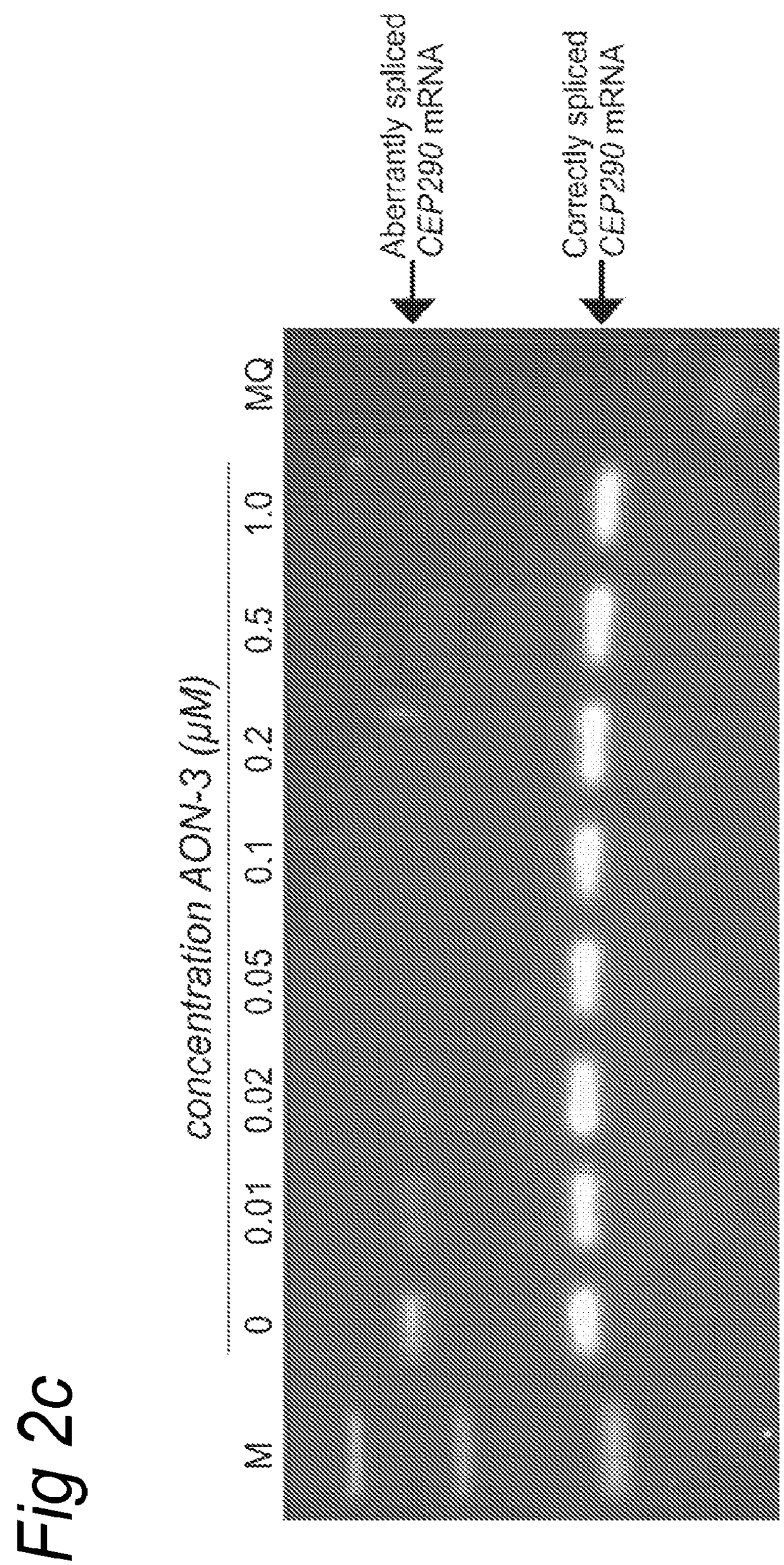

FIGS. 2*a*, 2*b* and 2*c* AON-based rescue of aberrant CEP290 splicing A) RT-PCR analysis of CEP290 mRNA isolated from lymphoblastoid cells of one control individuals and two individuals affected with LCA, that were cultured in the absence or presence of a selected AON (AON-3) direct against the aberrant CEP290 exonin a final concentration of 1.0 μM. The upper band represents the aberrant CEP290 splice product, whereas the lower band represents the wild-type CEP290 splice product. M: 100-bp marker. MQ: negative water control.

B) Specificity of AON-based rescue. Similar to A), cells were transfected with AON-3, or a sense oligonucleotide directed to the same target site (SON-3). Left panel: RT-PCR reaction using primers located in exon 26 and exon 27. Right panel: RT-PCR reaction using primers located in exon 26 and exon 31.

C) Dose-dependent rescue of CEP290 mRNA splicing. Similar to A), cells were transfected with different concentrations of the selected AON, ranging from 0.01 to 1.0 μM.

Figure 3A:
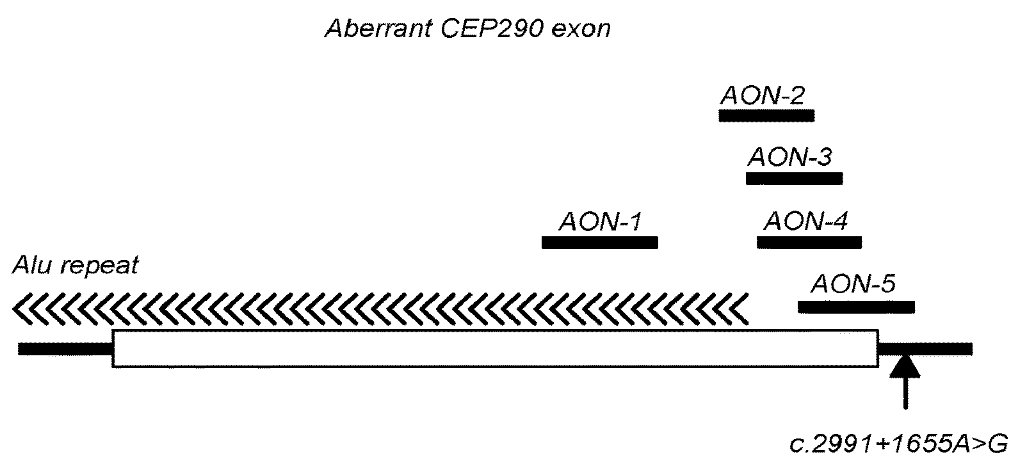
Figure 3B:
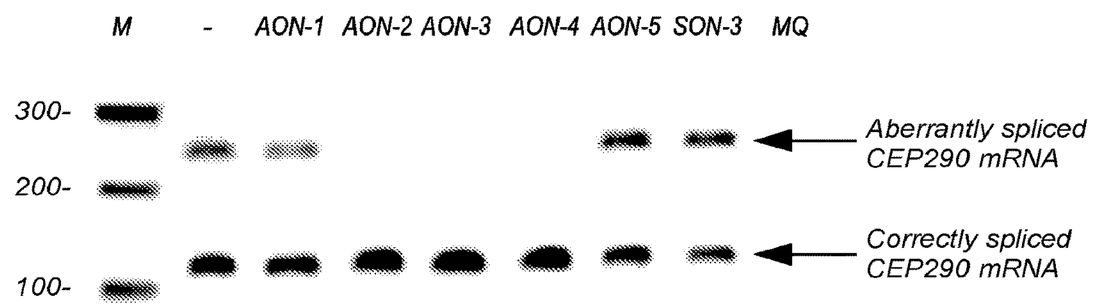

FIGS. 3*a* and 3*b* Sequence specificity in AON-based rescue of aberrant CEP290 splicing A) Overview of the aberrant (CEP290 exon, and the relative positions of the AONs that were selected. The 5'-end of the aberrant exon is part of an Alu repeat.

B) RT-PCR analysis of CEP290 mRNA isolated from lymphoblastoid cells of an LCA patient that were cultured in the absence or presence of different AONs direct against the aberrant CEP290 exon (AON-1 to -5), or one sense oligonucleotide (SON-3). The AONs and SON were transfected in a final concentration of 0.1 μM. The upper band represents the aberrant (CEP290 splice product, whereas the lower band represents the wild-type CEP290 splice product. M: 100-bp marker.

SEQUENCES

All sequences herein are depicted from 5'→3'

TABLE 1

Sequences as set forth in the Sequence Listing

| SEQ ID NO: | SEQ type | Description |
|---|---|---|
| 1 | Genomic DNA | CEP290 |
| 2 | cDNA | CEP290 |
| 3 | PRT | CEP290 protein |
| 4 | DNA | 128 nucleotide aberrant CEP290 exon |
| 5 | PRT | CEP290 aberrant protein |
| 6 | Polynucleotide | 143 nucleotide motif |
| 7 | Polynucleotide | 42 nucleotide motif |
| 8 | Polynucleotide | 24 nucleotide motif |
| 9 | AON-1 | taatcccagcactttaggag |
| 10 | AON-2 | gggccaggtgcggtgg |
| 11 | AON-3 | aactggggccaggtgcg |
| 12 | AON-4 | tacaactggggccaggtg |
| 13 | AON-5 | actcacaattacaactgggg |
| 14 | SON-3 | cgcacctggccccagtt |
| 15 | PCR primer | tgctaagtacagggacatcttgc |
| 16 | PCR primer | agactccacttgttcttttaaggag |

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonucleotide Synthesis* (N. Gait editor); *Nucleic Acid Hybridization* (Hames and Higgins, eds.).

EXAMPLES

Materials and Methods

Design Antisense Oligonucleotides

The 128-bp sequence of the aberrant CEP290 exon that is included into the mutant CEP290 mRNA was analyzed for the presence of exonic splice enhancer motifs using the ESE finder 3.0 program (http://rulai.cshl.edu/cgi-bin/tools/ESE3/esefinder.cgi?process=home). RNA antisense oligonucleotides were purchased from Eurogentec, and designed with a Tm of 58° C., and modified with a 2'-O-methyl group at the sugar chain and a phosphothiorate backbone, and dissolved in phosphate buffered saline.

Cell Culture

Human B-lymphoblasts cells of LCA patients homozygously carrying the intronic mutation in CEP290 were immortalized by transformation with the Eppstein-Barr virus, as described previously. (Wall F E, 1995). Cells were cultured in RPMI1640 medium (Gibco) containing 10% (v/v) fetal calf serum (Sigma), 1% 10 U/μl penicillin and 10 μg/μl streptomycin (Gibco), and 1% GlutaMAX (Gibco), at a density of $0.5\times10^6$ cells/ml. Cells were passaged twice a week.

Transfection of AONs

A day before transfection, $1.0\times10^6$ cells were seeded in each well of a 6-wells plate, in a total volume of 2 ml complete medium. Transfection mixtures were prepared by combining 2.5 μl AON in a desired concentration, or distilled water, 5 μl transfection reagent (ExGen in vitro 500, Fermentas) and 92.5 μl 150 mM NaCl, and incubated at room temperature for 10 minutes, before addition to the cells. Six hours after transfection, 8 ml of low-serum medium (complete medium with only 1% fetal calf serum) was added. Forty-eight hours after transfection, cells were collected and washed with 1×PBS, before directly proceeding to RNA isolation.

RNA Isolation and RT-PCR

Total RNA was isolated from transfected lymphoblastoid cells using the Nucleospin RNA II isolation kit (Machery Nagel), according to manufacturer's protocol. Subsequently, 1 μg of total RNA was used for cDNA synthesis using the iScript cDNA synthesis kit (Bio-Rad). Five percent of the cDNA was used for each PCR reaction. Part of the CEP290 cDNA was amplified under standard PCR conditions supplemented with 5% Q-solution (Qiagen), and using forward primer tgctaagtacagggacatcttgc (SEQ ID NO: 15) and reverse primer agactccacttgttcttttaaggag (SEQ ID NO: 16) that are located in exon 26 and exon 27 of the human CEP290 gene, respectively. PCR products were resolved on a 1.5% agarose gel. Bands presumably representing correctly and aberrantly spliced CEP290 were excised from the gel, purified using Nucleospin Extract II isolation kit and sequenced from both strands with the ABI PRISM Big Dye Terminator Cycle Sequencing V2.0 Ready Reaction kit and the ABI PRISM 3730 DNA analyzer (Applied Biosystems).

Introduction

Here, we describe the use of AONs to redirect normal splicing of CEP290 in patient-derived lymphoblast cells, and show a sequence-specific and dose-dependent decrease in levels of aberrantly spliced CEP290, thereby revealing the potential of AON-based therapy to treat CEP290-associated LCA.

Results

Figure 1:
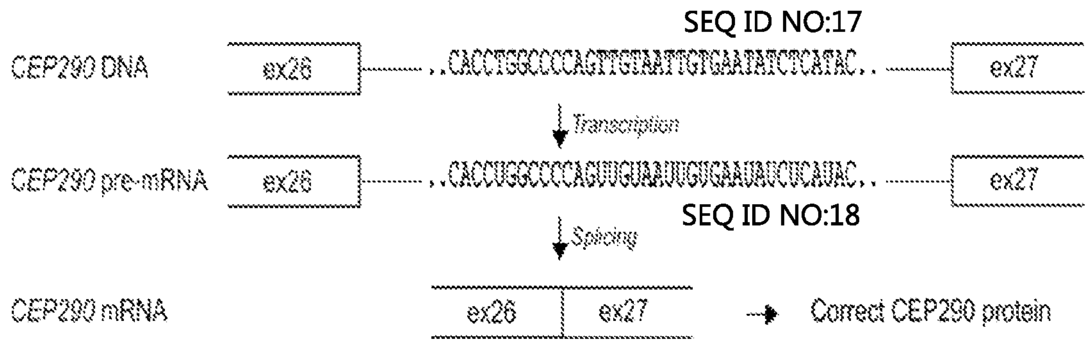
FIG. 1 CEP290 splicing and AON function
Figure 1:
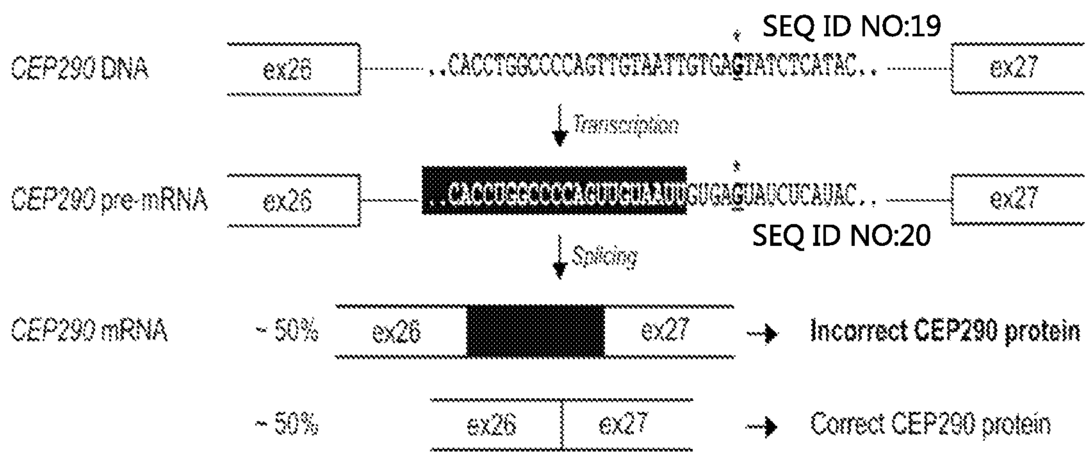
Figure 1:
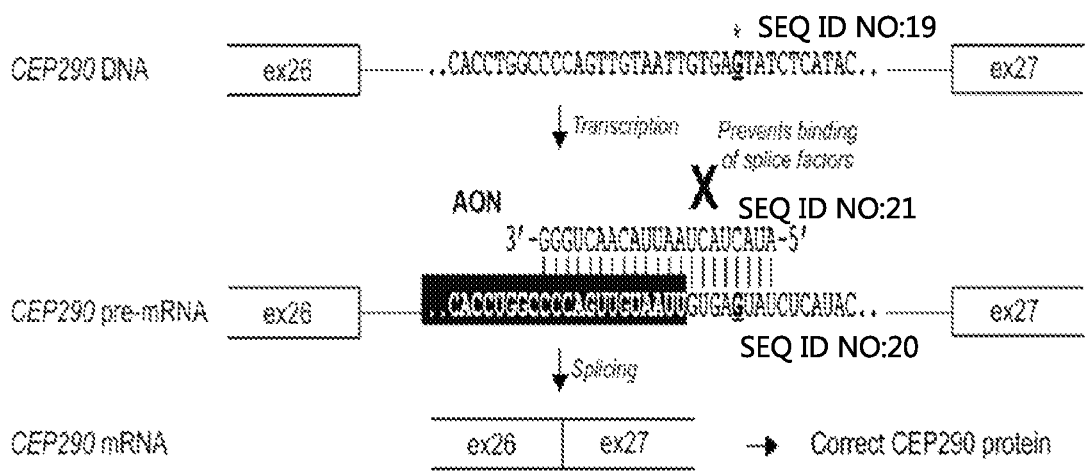

The intronic CEP290 mutation (c.2991+1655A>G) creates a cryptic splice donor site that results in the inclusion of an aberrant exon into the CEP290 mRNA (FIG. 1). Addition of AONs directed against the aberrant exon would prevent the insertion of this exon by preventing the binding of factors that are essential for splicing such as the U1- and U2snRNP complexes, and serine-arginine rich proteins, thereby restoring normal CEP290 splicing and protein synthesis (FIG. 1). AONs can target splice sites as well as exonic sequences, although in the particular case of the Duchenne muscular dystrophy DMD gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant CEP290 exon (128 nucleotides exonic sequence plus 15 nucleotides of intronic sequence on each side) was scrutinized for exonic splice enhancer binding motifs, using the ESE finder 3.0 program (Smith et al, 2006). At the 3'-end of the aberrant exon, two SC35-binding motifs were predicted (data not shown). Hence, the first AON was designed such that it encompassed these two motifs (designated AON-3, SEQ ID NO: 11), and being complementary to the CEP290 mRNA.

To determine whether AON-3 has exon-skipping potential in vitro, immortalized lympoblastoid cells of two unrelated individuals with LCA homozygously carrying the intronic CEP290 founder mutation c.2991+1655A>G, as well as one control individual were cultured in the absence or presence of 1 μM AON-3. As expected, in the control individual, only a band representing correctly spliced CEP290 was observed, whereas in both affected individuals two products were present, one representing correctly spliced, and one representing aberrantly spliced CEP290 mRNA. Upon addition of AON-3, a strong decrease in aberrantly spliced CEP290 was noted, in both individuals with LCA (FIG. 2*a*). Next, the specificity of AON-3 was assessed by transfecting a sense oligonucleotide directed to the same target site (SON-3, SEQ ID NO: 14). RT-PCR analysis showed that in the cells transfected with SON-3, both the aberrantly spliced and the correctly spliced CEP290 mRNA molecules are still present (FIG. 2*b*, left panel), demonstrating the specificity of the antisense sequence. Using an additional pair of primers that amplifies larger products, similar results were obtained (FIG. 2*b*, right panel). Interestingly, the decrease in aberrantly spliced CEP290 appears to coincide with an increased intensity of the product representing correctly spliced CEP290 mRNA. These data indicate that the aberrant product is not degraded, but that the AON transfection truly induces exon skipping, resulting in the synthesis of more correctly spliced wild-type (CEP290 mRNA. To determine the effective dose of AON-3, cells were transfected with various concentrations of AON-3, ranging from 0.01 to 1.0 μM. Even at the lowest concentration of 0.01 μM, a marked reduction in aberrantly spliced CEP290 was observed. The maximum amount of exon skipping was observed at 0.05 or 0.1 μM of AON, indicating that these concentrations are sufficient to convert almost all aberrantly spliced CEP290 (FIG. 2*c*).

The effectiveness of AONs in splice modulation is thought to merely depend on the accessibility of the target mRNA molecule, and hence may differ tremendously between neighboring sequences. To determine whether this sequence specificity also applies for CEP290, several AONs were designed that target the aberrant CEP290 exon (Table 1). This exon consists of 128 base pairs, the majority of which are part of an Alu repeat, one of the most frequent repetitive elements in the human genome (Schmidt et al, 1982), covering the entire 5'-end of the aberrant exon (FIG. 3*a*). Hence, the majority of AONs were designed to be complementary to the 3'-end of the aberrant exon or the splice donor site (FIG. 3*a*). In total, five AONs were transfected at a final concentration of 0.1 μM, which was shown to be optimal for AON-3. Interestingly, besides AON-3, also AON-2 (SEQ ID NO: 10) and AON-4 (SEQ ID NO: 12) resulted in high levels of exon skipping. In contrast, AON-1 (SEQ ID NO: 9) that targets the Alu repeat region, and AON-5 (SEQ ID NO: 13) that is directed against the splice donor site, hardly showed any exon skipping potential (FIG. 3*b*). These data demonstrate the sequence specificity in AON-based exon skipping of CEP290 and highlight a small region of the aberrant CEP290 exon as a potential therapeutic target.

Discussion

In this study, we explored the therapeutic potential of AONs to correct a splice defect caused by an intronic mutation in CEP290. In immortalized lymphoblast cells of LCA patients homozygously carrying the intronic CEP290 mutation c.2991+1655A>G, transfection of some but not all AONs resulted in skipping of the aberrant exon, thereby almost fully restoring normal CEP290 splicing.

AONs have been the focus of therapeutic research for over a decade, for the treatment of a variety of genetic diseases (Hammond et al, 2011). These strategies include the use of AONs to block the recognition of aberrant splice sites, to alter the ratio between two naturally occurring splice isoforms, to induce skipping of exons that contain protein-truncating mutations, or to induce the skipping of exons in order to restore the reading-frame of a gene that is disrupted by a genomic deletion, allowing the synthesis of a (partially) functional protein (Hammond et al, 2011). The latter approach is already being applied in phase I/II clinical trials for the treatment of patients with Duchenne muscular dystrophy, with promising results (Kinali et al, 2009; van Deutekom et al, 2007).

The intronic CEP290 mutation is an ideal target for AON-based therapy, since this mutation results in the inclusion of an aberrant exon in the CEP290 mRNA which is normally not transcribed. Inducing skipping of this aberrant exon by AONs fully restores the normal CEP290 mRNA, allowing normal levels of CEP290 protein to be synthesized. A second major advantage is that although this AON-approach is a mutation-specific therapeutic strategy, the intronic CEP290 mutation is by far the most frequent LCA-causing mutation.[4] Based on the estimated prevalence of LCA (1:50,000), and the observed frequency of the intronic CEP290 mutation in Northern-Europe (26%) (Coppieters et al, 2010) and the U.S. (10%) (Stone, 2007), at least one thousand and, depending on the frequency of the mutation in other populations, perhaps many more individuals worldwide have LCA due to this mutation. Finally, although the LCA phenotype associated with CEP290 mutations is severe, it appears that the photoreceptor integrity, especially in the macula, as well as the anatomical structure of the visual connections to the brain, are relatively intact in LCA patients with CEP290 mutations, which would allow a window of opportunity for therapeutic intervention (Cideciyan et al, 2007).

The study described here provides a proof-of-principle of AON-based therapy for CEP290-associated LCA in vitro, using immortalized patient lymphoblast cells. In order to determine the true therapeutic potential of this method for treating LCA, additional studies are needed that include the development of therapeutic vectors, and assessment of efficacy and safety in animal models. Although naked AONs, or conjugated to cell-penetrating peptides, can be delivered to the retina by intraocular injections, the limited stability of the AONs would require multiple injections in each individual. In contrast, by using viral vectors, a single subretinal injection would suffice to allow a long-term expression of the therapeutic construct. Previously, others have used recombinant adeno-associated viral (rAAV) vectors carrying U1- or modified U7snRNA constructs to efficiently deliver AON sequences, in the mdx mouse model for DMD, or in DMD patient myoblasts, respectively (Geib et al, 2009; Goyenhalle et al, 2004). In line with this, AONs targeting the aberrant exon of CEP290 could be cloned within such constructs, and delivered to the retina by subretinal injections of rAAV-5 or -8 serotypes that efficiently transduce photoreceptor cells where the endogenous CEP290 gene is expressed (Alloca et al, 2007; Lebherz et al, 2008). Using rAAV-2 vectors, no long-lasting immune response was evoked upon subretinal injections of these vectors in patients with RPE65 mutations (Simonella et al, 2009), and also for rAAV-5 and rAAV-8, immune responses appear to be absent or limited, at least in animal models (Li et al, 2009; Vandenberghe et al, 2011). One final safety aspect concerns the specificity of the sequence that is used to block the splicing of the aberrant CEP290 exon. As stated before, the majority of this exon is part of an Alu repeat, and AONs directed against this repeat will likely bind at multiple sites in the human genome, increasing the chance to induce off-target effects. The AONs that were shown to be effective in this study do not fully target the Alu repeat sequence, but are also not completely unique in the human genome. However, when blasting against the EST database, no exact hits are found, indicating that at the level of expressed genes, these sequences are unlikely to induce off-target effects and deregulate normal splicing of other genes. To further study the efficacy and safety of AON-based therapy for CEP290-associated LCA in vivo, we are currently generating a transgenic knock-in mouse model that carries part of the human CEP290 gene (exon 26 to exon 27, with and without the intronic mutation) which is exchanged with its mouse counterpart. Compared to gene augmentation therapy, AON-based therapy has a number of advantages. First, in gene augmentation therapy, a ubiquitous or tissue-specific promoter is used to drive expression of the wild-type cDNA encoding the protein that is mutated in a certain patient. For instance in one clinical trial for RPE65 gene therapy, the chicken beta-actin promoter was used (Maguire et al, 2008). Using these but also fragments of the endogenous promoters, it is difficult to control the levels of expression of the therapeutic gene. In some cases, like for the RPE65 protein that has an enzymatic function, expression levels beyond those of the endogenous gene might not be harmful to the retina. For other genes however, including those that encode structural proteins like CEP290, tightly-regulated expression levels might be crucial for cell survival, and overexpression of the therapeutic protein might exert toxic effects. Using AONs, the therapeutic intervention occurs at the pre-mRNA level, and hence does not interfere with the endogenous expression levels of the target gene. A second issue is the use of the viral vector. Of a variety of different recombinant viral vectors, rAAVs are considered to be most suitable for treating retinal dystrophies, because of their relatively high transduction efficiency of retinal cells, and their limited immunogenicity. The major drawback of rAAVs however is their limited cargo size of 4.8 kb. Again, for some genes like RPE65, this is not a problem. For many other retinal genes however, like CEP290 (with an open reading frame of 7.4 kb), but also ABCA4 and USH2A, the size of their full-length cDNAs exceeds the cargo size of the currently available pool of rAAVs. One way to overcome this problem is to express cDNAs that express only partial proteins with residual activity, as has been suggested for CEP290 by expressing the N-terminal region of CEP290 in a zebrafish model (Baye et al, 2011). Other viral vectors, like lentivirus or adenoviruses have a higher cargo capacity that rAAVs (~8 kb), but are less efficient in transducing retinal cells, and adenoviruses have a higher immunogenic potential (den Hollander et al, 2010). For AON-based therapy, the size limitations of AAV are not a problem, since the small size of the AONs and the accompanying constructs easily fit within the available AAVs.

In conclusion, this study shows that administration of AONs to cultured patient cells almost fully corrects a splice defect that is caused by a frequent intronic mutation in CEP290 that causes LCA. These data warrant further research to determine the therapeutic potential of AON-based therapy for CEP290-associated LCA, in order to delay or cease the progression of this devastating blinding disease.

REFERENCE LIST

1. Leber, T. (1869). Uber Retinitis Pigmentosa und angeborene Amaurose. von Graefe's Archives Ophthalmology 15, 1-25.
2. Koenekoop, R. K., Lopez, I., den Hollander, A. I., Allikmets, R., and Cremers, F. P. (2007). Genetic testing for retinal dystrophies and dysfunctions: benefits, dilemmas and solutions. Clin Experiment Ophthalmol 35, 473-485.
3. Stone, E. M. (2007). Leber congenital amaurosis—a model for efficient genetic testing of heterogeneous disorders: LXIV Edward Jackson Memorial Lecture. Am J Ophthalmol 144, 791-811.
4. den Hollander, A. I., Roepman, R., Koenekoop, R. K., and Cremers, F. P. M. (2008). Leber congenital amaurosis: genes, proteins and disease mechanisms. Prog Retin Eye Res 27, 391-419.
5. Estrada-Cuzcano, A., Koenekoop, R. K., Coppieters, F., Kohl, S., Lopez, I., Collin, R. W. J., De Baere, E. B., Roeleveld, D., Marek, J., Bernd, A. et al (2011). IQCB1 mutations in patients with leber congenital amaurosis. Invest Ophthalmol Vis Sci 52, 834-839.
6. den Hollander, A. I., Koenekoop, R. K., Yzer, S., Lopez, I., Arends, M. L., Voesenek, K. E., Zonneveld, M. N., Strom, T. M., Meitinger, T., Brunner, H. G. et al (2006). Mutations in the CEP290 (NPHP6) gene are a frequent cause of Leber congenital amaurosis. Am J Hum Genet 79, 556-561.
7. Perrault, I., Delphin, N., Hanein, S., Gerber, S., Dufier, J. L., Roche, O., foort-Dhellemmes, S., Dollfus, H., Fazzi, E., Munnich, A. et al (2007). Spectrum of NPHP6/CEP290 mutations in Leber congenital amaurosis and delineation of the associated phenotype. Hum Mutat 28, 416.
8. Baala, L., Audollent, S., Martinovic, J., Ozilou, C., Babron, M. C., Sivanandamoorthy, S., Saunier, S., Salomon, R., Gonzales, M., Rattenberry, E. et al (2007). Pleiotropic effects of CEP290 (NPHP6) mutations extend to Meckel syndrome. Am J Hum Genet 81, 170-179.
9. Frank, V., den Hollander, A. I., Bruchle, N. O., Zonneveld, M. N., Nurnberg, G., Becker, C., Du, B. G., Kendziorra, H., Roosing, S., Senderek, J. et al (2008). Mutations of the CEP290 gene encoding a centrosomal protein cause Meckel-Gruber syndrome. Hum Mutat 29, 45-52.
10. Helou, J., Otto, E. A., Attanasio, M., Allen, S. J., Parisi, M. A., Glass, I., Utsch, B., Hashmi, S., Fazzi, E., Omran, H. et al (2007). Mutation analysis of NPHP6/CEP290 in patients with Joubert syndrome and Senior-Loken syndrome. J Med Genet 44, 657-663.
11. Valente, E. M., Silhavy, J. L., Brancati, F., Barrano, G., Krishnaswami, S. R., Castori, M., Lancaster, M. A., Boltshauser, E., Boccone, L., Al-Gazali, L. et al (2006). Mutations in CEP290, which encodes a centrosomal protein, cause pleiotropic forms of Joubert syndrome. Nat Genet 38, 623-625.
12. Coppieters, F., Casteels, I., Meire, F., De Jaegere S., Hooghe, S., van Regemorter N., Van Esch H., Matuleviciene, A., Nunes, L., Meersschaut, V. et al (2010). Genetic screening of LCA in Belgium: predominance of CEP290 and identification of potential modifier alleles in AHI1 of CEP290-related phenotypes. Hum Mutat 31, E1709-E1766.
13. Littink, K. W., Pott, J. W., Collin, R. W. J., Kroes, H. Y., Verheij, J. B., Blokland, E. A., de Castro Miro M., Hoyng, C. B., Klaver, C. C., Koenekoop, R. K. et al (2010). A novel nonsense mutation in CEP290 induces exon skipping and leads to a relatively mild retinal phenotype. Invest Ophthalmol Vis Sci 51, 3646-3652.
14. Bainbridge, J. W., Smith, A. J., Barker, S. S., Robbie, S., Henderson, R., Balaggan, K., Viswanathan, A., Holder, G. E., Stockman, A., Tyler, N. et al (2008). Effect of gene therapy on visual function in Leber's congenital amaurosis. N Engl J Med 358, 2231-2239.
15. Cideciyan, A. V., Aleman, T. S., Boye, S. L., Schwartz, S. B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.
16. Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada—Mutations by Ocular Subretinal Injection of Adeno-Associated Virus Gene Vector: Short-Term Results. Hum Gene Ther
17. Maguire, A. M., Simonelli, F., Pierce, E. A., Pugh, E. N., Jr., Mingozzi, F., Bennicelli, J., Banfi, S., Marshall, K. A., Testa, F., Surace, E. M. et al (2008). Safety and efficacy of gene transfer for Leber's congenital amaurosis. N Engl J Med 358, 2240-2248.
18. Maguire, A. M., High, K. A., Auricchio, A., Wright, J. F., Pierce, E. A., Testa, F., Mingozzi, F., Bennicelli, J. L., Ying, G. S., Rossi, S. et al (2009). Age-dependent effects of RPE65 gene therapy for Leber's congenital amaurosis: a phase 1 dose-escalation trial. Lancet 374, 1597-1605.
19. den Hollander, A. I., Black, A., Bennett, J., and Cremers, F. P. M. (2010). Lighting a candle in the dark: advances in genetics and gene therapy of recessive retinal dystrophies. J Clin Invest 120, 3042-3053.
20. Aartsma-Rus, A., Houlleberghs, H., van Deutekom, J. C., van Ommen, G. J., and 't Hoen, P. A. (2010). Exonic sequences provide better targets for antisense oligonucleotides than splice site sequences in the modulation of Duchenne muscular dystrophy splicing. Oligonucleotides 20, 69-77.
21. Aartsma-Rus, A., van, V. L., Hirschi, M., Janson, A. A., Heemskerk, H., de Winter, C. L., de, K. S., van Deutekom, J. C., 't Hoen, P. A., and van Ommen, G. J. (2008). Guidelines for Antisense Oligonucleotide Design and Insight Into Splice-modulating Mechanisms. Mol Ther
22. Smith, P. J., Zhang, C., Wang, J., Chew, S. L., Zhang, M. Q., and Krainer, A. R. (2006). An increased specificity score matrix for the prediction of SF2/ASF-specific exonic splicing enhancers. Hum Mol Genet 15, 2490-2508.

23. Schmid, C. W. and Jelinek, W. R. (1982). The Alu family of dispersed repetitive sequences. Science 216, 1065-1070.

24. Hammond, S. M. and Wood, M. J. (2011). Genetic therapies for RNA mis-splicing diseases. Trends Genet 27, 196-205.

25. Kinali, M., rechavala-Gomeza, V., Feng, L., Cirak, S., Hunt, D., Adkin, C., Guglieri, M., Ashton, E., Abbs, S., Nihoyannopoulos, P. et al (2009). Local restoration of dystrophin expression with the morpholino oligomer AVI-4658 in Duchenne muscular dystrophy: a single-blind, placebo-controlled, dose-escalation, proof-of-concept study. Lancet Neurol 8, 918-928.

26. van Deutekom, J. C., Janson, A. A., Ginjaar, I. B., Frankhuizen, W. S., Aartsma-Rus, A., Bremmer-Bout, M., Den Dunnen, J. T., Koop, K., van der Kooi, A. J., Goemans, N. M. et al (2007). Local dystrophin restoration with antisense oligonucleotide PRO051. N Engl J Med 357, 2677-2686.

27. Coppieters, F., Lefever, S., Leroy, B. P., and De, B. E. (2010). CEP290, a gene with many faces: mutation overview and presentation of CEP290base. Hum Mutat 31, 1097-1108.

28. Cideciyan, A. V., Aleman, T. S., Jacobson, S. G., Khanna, H., Sumaroka, A., Aguirre, G. K., Schwartz, S. B., Windsor, E. A., He, S., Chang, B. et al (2007). Centrosomal-ciliary gene CEP290/NPHP6 mutations result in blindness with unexpected sparing of photoreceptors and visual brain: implications for therapy of Leber congenital amaurosis. Hum Mutat 28, 1074-1083.

29. Geib, T. and Hertel, K. J. (2009). Restoration of full-length SMN promoted by adenoviral vectors expressing RNA antisense oligonucleotides embedded in U7 snRNAs. PLoS One 4, e8204.

30. Goyenvalle, A., Vulin, A., Fougerousse, F., Leturcq, F., Kaplan, J. C., Garcia, L., and Danos, O. (2004). Rescue of dystrophic muscle through U7 snRNA-mediated exon skipping. Science 306, 1796-1799.

31. Allocca, M., Mussolino, C., Garcia-Hoyos, M., Sanges, D., lodice, C., Petrillo, M., Vandenberghe, L. H., Wilson, J. M., Marigo, V., Surace, E. M. et al (2007). Novel adeno-associated virus serotypes efficiently transduce murine photoreceptors. J Virol 81, 11372-11380.

32. Lebherz, C., Maguire, A., Tang, W., Bennett, J., and Wilson, J. M. (2008). Novel AAV serotypes for improved ocular gene transfer. J Gene Med 10, 375-382.

33. Simonelli, F., Maguire, A. M., Testa, F., Pierce, E. A., Mingozzi, F., Bennicelli, J. L., Rossi, S., Marshall, K., Banfi, S., Surace, E. M. et al (2009). Gene Therapy for Leber's Congenital Amaurosis is Safe and Effective Through 1.5 Years After Vector Administration. Mol Ther 34. Li, W., Kong, F., Li, X., Dai, X., Liu, X., Zheng, Q., Wu, R., Zhou, X., Lu, F., Chang, B. et al (2009). Gene therapy following subretinal AAV5 vector delivery is not affected by a previous intravitreal AAV5 vector administration in the partner eye. Mol Vis 15, 267-275.

35. Vandenberghe, L. H., Bell, P., Maguire, A. M., Cearley, C. N., Xiao, R., Calcedo, R., Wang, L., Castle, M. J., Maguire, A. C., Grant, R. et al (2011). Dosage Thresholds for AAV2 and AAV8 Photoreceptor Gene Therapy in Monkey. Sci Transl Med 3, 88ra54.

36. Baye, L. M., Patrinostro, X., Swaminathan, S., Beck, J. S., Zhang, Y., Stone, E. M., Sheffield, V. C., and Slusarski, D. C. (2011). The N-terminal region of centrosomal protein 290 (CEP290) restores vision in a zebrafish model of human blindness. Hum Mol Genet 20, 1467-1477.

37. Dorn and Kippenberger, Curr Opin Mol Ther 2008 10(1) 10-20

38. Nielsen, et al. (1991) Science 254, 1497-1500

39. Govindaraju and Kumar (2005) Chem. Commun, 495-497

40. Egholm et al (1993) Nature 365, 566-568

41. Morita et al. 2001. Nucleic Acid Res Supplement No. 1: 241-242

42. Gorman L, et al, Stable alteration of pre-mRNA splicing patterns by modified U7 small nuclear RNAs. Proc Natl Acad Sci USA 1998; 95(9):4929-34

43. Suter D, et al, Double-target antisense U7 snRNAs promote efficient skipping of an aberrant exon in three human beta-thalassemic mutations. Hum Mol Genet 1999; 8(13):2415-23

44. Remington: The Science and Practice of Pharmacy, 20th Edition. Baltimore, Md.: Lippincott Williams & Wilkins, 2000

The invention claimed is:

1. An antisense oligonucleotide that is capable of modulating splicing of CEP290 c.2991+1655A>G, wherein the antisense oligonucleotide consists of 14 to 20 nucleotides that are 100% complementary to a sequence within SEQ ID NO: 6 and wherein the antisense oligonucleotide comprises one or more sugar moieties that are mono- or di-substituted at the 2', 3' and/or 5' position.

2. The antisense oligonucleotide according to claim 1, wherein the antisense oligonucleotide comprises at least one phosphorothioate internucleoside linkage.

3. The antisense oligonucleotide according to claim 1, wherein the antisense oligonucleotide comprises at least one chiral phosphorothioate internucleoside linkage.

4. The antisense oligonucleotide according to claim 1, wherein the antisense oligonucleotide comprises a 2'-O alkyl modification.

5. The antisense oligonucleotide according to claim 4, wherein the 2'-O alkyl modification is selected from the group consisting of a 2'-O-methyl modification, a 2'-O-ethyl modification and a 2'-O-propyl modification.

6. The antisense oligonucleotide according to claim 1, wherein the antisense oligonucleotide comprises a 2'-methoxyethoxy modification.

7. A pharmaceutical composition comprising an antisense oligonucleotide according to claim 1 and a pharmaceutically acceptable excipient.

8. The pharmaceutical composition according to claim 7, wherein the antisense oligonucleotide comprises at least one phosphorothioate internucleoside linkage.

9. The pharmaceutical composition according to claim 7, wherein the antisense oligonucleotide comprises at least one chiral phosphorothioate internucleoside linkage.

10. The pharmaceutical composition according to claim 9, wherein the antisense oligonucleotide comprises a 2'-O alkyl modification.

11. The pharmaceutical composition according to claim 10, wherein the 2'-O alkyl modification is selected from the group consisting of a 2'-O-methyl modification, a 2'-O-ethyl modification and a 2'-O-propyl modification.

12. The pharmaceutical composition according to claim 9, wherein the antisense oligonucleotide comprises a 2'-methoxyethoxy modification.

13. A viral vector expressing an antisense oligonucleotide that is capable of modulating splicing of CEP290 c.2991+1655A>G, wherein the antisense oligonucleotide consists of 14 to 20 nucleotides that are 100% complementary to SEQ ID NO: 6.

14. A pharmaceutical composition comprising a viral vector according to claim 13 and a pharmaceutically acceptable excipient.

* * * * *

SEQUENCE LISTING

```
<160> NUMBER OF SEQ ID NOS: 21

<210> SEQ ID NO 1
<211> LENGTH: 93203
<212> TYPE: DNA
<213> ORGANISM: Homo sapiens
<220> FEATURE:
<221> NAME/KEY: 5'UTR
<222> LOCATION: (1)..(909)
<223> OTHER INFORMATION: Intron from 318 to 882
<220> FEATURE:
<221> NAME/KEY: exon
<222> LOCATION: (910)..(1011)
<220> FEATURE:
<221> NAME/KEY: Intron
<222> LOCATION: (1012)..(1183)
<220> FEATURE:
<221> NAME/KEY: exon
<222> LOCATION: (1184)..(1261)
```

```
<220> FEATURE:
<221> NAME/KEY: Intron
<222> LOCATION: (1262)..(2652)
<220> FEATURE:
<221> NAME/KEY: exon
<222> LOCATION: (2653)..(2722)
<220> FEATURE:
<221> NAME/KEY: Intron
<222> LOCATION: (2723)..(3025)
<220> FEATURE:
<221> NAME/KEY: exon
<222> LOCATION: (3026)..(3072)
<220> FEATURE:
<221> NAME/KEY: Intron
<222> LOCATION: (3073)..(5430)
<220> FEATURE:
<221> NAME/KEY: exon
<222> LOCATION: (5431)..(5574)
<220> FEATURE:
<221> NAME/KEY: Intron
<222> LOCATION: (5575)..(10998)
<220> FEATURE:
<221> NAME/KEY: exon
<222> LOCATION: (10999)..(11052)
<220> FEATURE:
<221> NAME/KEY: Intron
<222> LOCATION: (11053)..(11651)
<220> FEATURE:
<221> NAME/KEY: exon
<222> LOCATION: (11652)..(11672)
<220> FEATURE:
<221> NAME/KEY: Intron
<222> LOCATION: (11673)..(11796)
<220> FEATURE:
<221> NAME/KEY: exon
<222> LOCATION: (11797)..(11949)
<220> FEATURE:
<221> NAME/KEY: Intron
<222> LOCATION: (11950)..(12340)
<220> FEATURE:
<221> NAME/KEY: exon
<222> LOCATION: (12341)..(12523)
<220> FEATURE:
<221> NAME/KEY: Intron
<222> LOCATION: (12524)..(13181)
<220> FEATURE:
<221> NAME/KEY: exon
<222> LOCATION: (13182)..(13271)
<220> FEATURE:
<221> NAME/KEY: Intron
<222> LOCATION: (13272)..(15778)
<220> FEATURE:
<221> NAME/KEY: exon
<222> LOCATION: (15779)..(15901)
<220> FEATURE:
<221> NAME/KEY: Intron
<222> LOCATION: (15902)..(16847)
<220> FEATURE:
<221> NAME/KEY: exon
<222> LOCATION: (16848)..(16971)
<220> FEATURE:
<221> NAME/KEY: Intron
<222> LOCATION: (16972)..(21050)
<220> FEATURE:
<221> NAME/KEY: exon
<222> LOCATION: (21051)..(21220)
<220> FEATURE:
<221> NAME/KEY: Intron
<222> LOCATION: (21221)..(21940)
<220> FEATURE:
<221> NAME/KEY: exon
<222> LOCATION: (21941)..(22103)
<220> FEATURE:
<221> NAME/KEY: Intron
<222> LOCATION: (22104)..(23473)
<220> FEATURE:
<221> NAME/KEY: exon
<222> LOCATION: (23474)..(23574)
<220> FEATURE:
```

```
<221> NAME/KEY: Intron
<222> LOCATION: (23575)..(23646)
<220> FEATURE:
<221> NAME/KEY: exon
<222> LOCATION: (23647)..(23734)
<220> FEATURE:
<221> NAME/KEY: Intron
<222> LOCATION: (23735)..(25071)
<220> FEATURE:
<221> NAME/KEY: exon
<222> LOCATION: (25072)..(25184)
<220> FEATURE:
<221> NAME/KEY: Intron
<222> LOCATION: (25185)..(27034)
<220> FEATURE:
<221> NAME/KEY: exon
<222> LOCATION: (27035)..(27119)
<220> FEATURE:
<221> NAME/KEY: Intron
<222> LOCATION: (27120)..(27654)
<220> FEATURE:
<221> NAME/KEY: exon
<222> LOCATION: (27655)..(27797)
<220> FEATURE:
<221> NAME/KEY: Intron
<222> LOCATION: (27798)..(30358)
<220> FEATURE:
<221> NAME/KEY: exon
<222> LOCATION: (30359)..(30523)
<220> FEATURE:
<221> NAME/KEY: Intron
<222> LOCATION: (30524)..(30865)
<220> FEATURE:
<221> NAME/KEY: exon
<222> LOCATION: (30866)..(31015)
<220> FEATURE:
<221> NAME/KEY: Intron
<222> LOCATION: (31016)..(33035)
<220> FEATURE:
<221> NAME/KEY: exon
<222> LOCATION: (33036)..(33151)
<220> FEATURE:
<221> NAME/KEY: Intron
<222> LOCATION: (33152)..(35118)
<220> FEATURE:
<221> NAME/KEY: exon
<222> LOCATION: (35119)..(35221)
<220> FEATURE:
<221> NAME/KEY: Intron
<222> LOCATION: (35222)..(35311)
<220> FEATURE:
<221> NAME/KEY: exon
<222> LOCATION: (35312)..(35542)
<220> FEATURE:
<221> NAME/KEY: Intron
<222> LOCATION: (35543)..(39205)
<220> FEATURE:
<221> NAME/KEY: exon
<222> LOCATION: (39206)..(39379)
<220> FEATURE:
<221> NAME/KEY: Intron
<222> LOCATION: (39380)..(45217)
<223> OTHER INFORMATION: Aberrant exon included in mutant CEP290 mRNA
      position 40902-41209 mutated nucleotide A>G in LCA patients at
      position 41034
<220> FEATURE:
<221> NAME/KEY: exon
<222> LOCATION: (45218)..(45329)
<220> FEATURE:
<221> NAME/KEY: Intron
<222> LOCATION: (45330)..(48241)
<220> FEATURE:
<221> NAME/KEY: exon
<222> LOCATION: (48242)..(48447)
<220> FEATURE:
<221> NAME/KEY: Intron
<222> LOCATION: (48448)..(49384)
<220> FEATURE:
<221> NAME/KEY: exon
```

<222> LOCATION: (49385)..(49536)
<220> FEATURE:
<221> NAME/KEY: Intron
<222> LOCATION: (49537)..(51377)
<220> FEATURE:
<221> NAME/KEY: exon
<222> LOCATION: (51378)..(51489)
<220> FEATURE:
<221> NAME/KEY: Intron
<222> LOCATION: (51490)..(52729)
<220> FEATURE:
<221> NAME/KEY: exon
<222> LOCATION: (52730)..(53185)
<220> FEATURE:
<221> NAME/KEY: Intron
<222> LOCATION: (53186)..(54272)
<220> FEATURE:
<221> NAME/KEY: exon
<222> LOCATION: (54273)..(54437)
<220> FEATURE:
<221> NAME/KEY: Intron
<222> LOCATION: (54438)..(55718)
<220> FEATURE:
<221> NAME/KEY: exon
<222> LOCATION: (55719)..(55826)
<220> FEATURE:
<221> NAME/KEY: Intron
<222> LOCATION: (55827)..(56043)
<220> FEATURE:
<221> NAME/KEY: exon
<222> LOCATION: (56044)..(56178)
<220> FEATURE:
<221> NAME/KEY: Intron
<222> LOCATION: (56179)..(57364)
<220> FEATURE:
<221> NAME/KEY: exon
<222> LOCATION: (57365)..(57631)
<220> FEATURE:
<221> NAME/KEY: Intron
<222> LOCATION: (57632)..(58262)
<220> FEATURE:
<221> NAME/KEY: exon
<222> LOCATION: (58263)..(58370)
<220> FEATURE:
<221> NAME/KEY: Intron
<222> LOCATION: (58371)..(58986)
<220> FEATURE:
<221> NAME/KEY: exon
<222> LOCATION: (58987)..(59186)
<220> FEATURE:
<221> NAME/KEY: Intron
<222> LOCATION: (59187)..(61821)
<220> FEATURE:
<221> NAME/KEY: exon
<222> LOCATION: (61822)..(62035)
<220> FEATURE:
<221> NAME/KEY: Intron
<222> LOCATION: (62036)..(62987)
<220> FEATURE:
<221> NAME/KEY: exon
<222> LOCATION: (62988)..(63125)
<220> FEATURE:
<221> NAME/KEY: Intron
<222> LOCATION: (63126)..(64298)
<220> FEATURE:
<221> NAME/KEY: exon
<222> LOCATION: (64299)..(64520)
<220> FEATURE:
<221> NAME/KEY: Intron
<222> LOCATION: (64521)..(64872)
<220> FEATURE:
<221> NAME/KEY: exon
<222> LOCATION: (64873)..(64995)
<220> FEATURE:
<221> NAME/KEY: Intron
<222> LOCATION: (64996)..(70290)
<220> FEATURE:
<221> NAME/KEY: exon
<222> LOCATION: (70291)..(70436)

```
<220> FEATURE:
<221> NAME/KEY: Intron
<222> LOCATION: (70437)..(70767)
<220> FEATURE:
<221> NAME/KEY: exon
<222> LOCATION: (70768)..(70923)
<220> FEATURE:
<221> NAME/KEY: Intron
<222> LOCATION: (70924)..(73571)
<220> FEATURE:
<221> NAME/KEY: exon
<222> LOCATION: (73572)..(73695)
<220> FEATURE:
<221> NAME/KEY: Intron
<222> LOCATION: (73696)..(78101)
<220> FEATURE:
<221> NAME/KEY: exon
<222> LOCATION: (78102)..(78236)
<220> FEATURE:
<221> NAME/KEY: Intron
<222> LOCATION: (78237)..(79438)
<220> FEATURE:
<221> NAME/KEY: exon
<222> LOCATION: (79439)..(79525)
<220> FEATURE:
<221> NAME/KEY: Intron
<222> LOCATION: (79526)..(81222)
<220> FEATURE:
<221> NAME/KEY: exon
<222> LOCATION: (81223)..(81387)
<220> FEATURE:
<221> NAME/KEY: Intron
<222> LOCATION: (81388)..(82196)
<220> FEATURE:
<221> NAME/KEY: exon
<222> LOCATION: (82197)..(82319)
<220> FEATURE:
<221> NAME/KEY: Intron
<222> LOCATION: (82320)..(83196)
<220> FEATURE:
<221> NAME/KEY: exon
<222> LOCATION: (83197)..(83369)
<220> FEATURE:
<221> NAME/KEY: Intron
<222> LOCATION: (83370)..(86499)
<220> FEATURE:
<221> NAME/KEY: exon
<222> LOCATION: (86500)..(86641)
<220> FEATURE:
<221> NAME/KEY: Intron
<222> LOCATION: (86642)..(87803)
<220> FEATURE:
<221> NAME/KEY: exon
<222> LOCATION: (87804)..(87877)
<220> FEATURE:
<221> NAME/KEY: Intron
<222> LOCATION: (87878)..(88470)
<220> FEATURE:
<221> NAME/KEY: exon
<222> LOCATION: (88471)..(88565)
<220> FEATURE:
<221> NAME/KEY: Intron
<222> LOCATION: (88566)..(91783)
<220> FEATURE:
<221> NAME/KEY: exon
<222> LOCATION: (91784)..(91863)
<220> FEATURE:
<221> NAME/KEY: Intron
<222> LOCATION: (91864)..(92802)
<220> FEATURE:
<221> NAME/KEY: exon
<222> LOCATION: (92803)..(93033)
<220> FEATURE:
<221> NAME/KEY: 3'UTR
<222> LOCATION: (93034)..(93203)

<400> SEQUENCE: 1

atttgaagtc ctcgttccac gccttctcat catcctgaac accgagctct gggactccgg     60
```

-continued

```
cggagaatct aaacgtaaag catcacccac ggtcgtgaac tgtaggctct cctggcatcc    120

gggatcttat tctggccttg gcggagttgg ggatggtgtc gcctagcagc cgctgccgct    180

ttggcttgct cgggaccatt tggctggacc cagagtccgc gtggaaccgc gatagggatc    240

tgtcagggcc cgcggccggg tccagcttgg tggttgcggt agtgagaggc ctccgctggt    300

tgccaggctt ggtctaggtg ggtggatcct tgtaagcagg attagcgagt cactccacgc    360

tcaggttctt tagcctgagg gcccgtgtgc cacagcatag ctaccccgcc cttccagcct    420

cgggtcccta atactgcctt gcttcggttc cagtttccgc cgcacaactt cactcattcc    480

aaatgttaat ttctgcgttt tttttcagcc ccaattctgt ttctccaaat cagggatgat    540

tgtcggcctt ccacagaccc tcgcgcttgc caggattagg gtgttcgcgc gcattgtggg    600

taggggtgtg gaggaaggga tccagaaatc ttaagtatta acttagatta gtgttagcaa    660

ggaagccgtc acattttatt tagccgggac actctgacag tttgtgccga ctgctatttt    720

tgatcaaggc tattttgccc acttgtctat tttgtggccc aattgtctgt tttgctaaca    780

tcagaaagtt ataatgaaat aatctgcaaa aaatgtaagg tgctagaaaa ccaataatac    840

tgtgtacctt gaaaatgcta atatacacct gttttgttac agaggtggag cacagtgaaa    900

gaattcaag atg cca cct aat ata aac tgg aaa gaa ata atg aaa gtt gac    951
          Met Pro Pro Asn Ile Asn Trp Lys Glu Ile Met Lys Val Asp
          1               5                   10

cca gat gac ctg ccc cgt caa gaa gaa ctg gca gat aat tta ttg att      999
Pro Asp Asp Leu Pro Arg Gln Glu Glu Leu Ala Asp Asn Leu Leu Ile
15                  20                  25                  30

tcc tta tcc aag gtgcttaatt ggtcaataat aatagatata tacattaact         1051
Ser Leu Ser Lys

tatgattaat ttattaataa aatatgaatt tatttttttc agggacaact ataattgtca   1111

caatctggaa gtgttcttat attttgcttg aaggttataa aatataaaac agttgctttt   1171

ctgtttactt ag gtg gaa gta aat gag cta aaa agt gaa aag caa gaa aat   1222
              Val Glu Val Asn Glu Leu Lys Ser Glu Lys Gln Glu Asn
              35                  40                  45

gtg ata cac ctt ttc aga att act cag tca cta atg aag gtttgtatgt      1271
Val Ile His Leu Phe Arg Ile Thr Gln Ser Leu Met Lys
        50                  55                  60

agtaggtttt aactataggt ttggctatta gtggaactat aaaaatctgt tcttatataa   1331

ggtaatcttt gtgaaaatac ctggtaatat ctacatcacc actaaaaaat gcaatatatt   1391

taaatgtgaa ttaagtattt tagtgtataa aacattgcta gtttctactt aaagtttcta   1451

aaagggtgtg taggggaaat agaatgagta tgttgaaaag taacataagg aaatatatct   1511

tgaggtccaa atgacaaatg cagacaatga ctgctatagg gatttgttaa gaggggaaat   1571

gatttaagag atgtcagaag acttcacaaa ggatcaatac tgaggagtag tgttagataa   1631

gtggaaggca atgcagtggt aagatagtaa gggaattcta gagctgttgg ttaccataaa   1691

taaatactga gaacaggaaa tatgtttatt ctttatattt gaggaaacaa ggtgcagcaa   1751

gtttgtagca gactgtagag aaaacaaatc ttgggtaagt actttgagat aggttgttga   1811

gggccttaaa ggtgtatttt atgctatcag caattgagaa ggcagtaaag gttttcgaaa   1871

cacaattgat aggtacaaaa atacacctta agaaggcaaa actgagtata ttatgtagga   1931

caaactgaag gaaattggag ctttgtagac atcacattat agcggagttt aaacctgaaa   1991

ttatggatta gaataatagc aattggaaca gaaaaaaagt agtggaaaga cattacaaag   2051

ggagatgttg cattactgga tataagactt gaggacttga ggtaaaaagg agaatcaaaa   2111
```

```
atgtttcatg ctattaaaaa tctagaaatt gtagtcttaa gtaagaaaat tgcctggcat   2171

ggtggctcac gtctgtaatc ccagcacttt gggaggccaa ggcaggagga ttgcttgagc   2231

ctgggagttc aagactagcc tggataatat agtgagtcct tgcctgtacg aaaaaatttg   2291

ccgagcatga tggcacacca agcatgatgg cacgccaagc atgatggcat gcacctgtag   2351

tcccagctac tcaggagact gagatgggaa gattgcttga gcccaggagg caggaggttg   2411

cagtgagctg agattgtgcc actgcactcc agcctgggtg acaaagtgag gccctatctc   2471

aaaagcaaaa aaaacaaaaa caaaaaccaa aaactattta ttcagcaaat atttactgaa   2531

cgtctccatg tgccagccat tgctggcact aaggatcata acaaataaaa cagaattttt   2591

attttcagtg cttacattcc agtataaagg catattgaaa taacctttttt ttaatgttta   2651

g atg aaa gct caa gaa gtg gag ctg gct ttg gaa gaa gta gaa aaa gct   2700
  Met Lys Ala Gln Glu Val Glu Leu Ala Leu Glu Glu Val Glu Lys Ala
                65                  70                  75

gga gaa gaa caa gca aaa ttt g gtaagcacct tggaaaaagt ttattatggt     2752
Gly Glu Glu Gln Ala Lys Phe
            80

attaaataat gaattccatt tgttcattaa actgtagaaa attaaattat attctataaa   2812

atatatatat tcagtttatt tttaatatat aacatttaat aataaatatt tctagactcc   2872

tattttatgg atctgccata taatactttt tgttacctta taatcatgat ggactctttt   2932

aaaagaatta attttgttat tgaaatttat ttaaaagttt gttttgtggt aactaatcaa   2992

ttaaaacgtt tttctttttt tttaaaaaaa tag aa  aat caa tta aaa act aaa    3045
                                     Glu Asn Gln Leu Lys Thr Lys
                                         85                  90

gta atg aaa ctg gaa aat gaa ctg gag gtatgtcttt ttgtattccc          3092
Val Met Lys Leu Glu Asn Glu Leu Glu
                95

taggatgtaa ttgtcattaa ttttattttg aattgttttc aaattttaaa attattgttg   3152

gctggaaaaa ttataaggat gattgtaatc atggttattt gtttattctg tatatgttct   3212

acatgcctat tatgtgcctt atatagtact aaggactgag catatggttg tgaacaaaat   3272

aagaagttaa ctgctggatg gagcttatag tcttgggaaa tatacagaaa gattactagt   3332

aactgaggtg gagggtgggt ggggatttga ggaatagtga cgaaagggtg ttatagaagt   3392

aatttttgac aaagctgaag gctaaaatat gaatgtattg ttgaagaaca aaatacattg   3452

agattcctga gaaggtagga atgtgataca aatggatcag cctttgaaag gaggaatacc   3512

cttttccttt gtgttaggag aggaggatga gtggatgagc gtgggaagag tggatgtgta   3572

tagaggcttt tatgtttgta ggcataatgc ttggaagttg aggggttggt gatgacatct   3632

tctgttaaaa agagtgggaa atggtgtggt cacattttaa ggaaattagg taaaatttga   3692

aatatattgg agacaggact ggagagttgg ggatctggag tcagacagat ttgagttcta   3752

gtcctgattc ttctactcgt taactctctg aacttggatg acctattgtt tttgattgta   3812

tatccagctc ctgggaaaat gccaagcact ttcaataaat actaaatgaa ttatggagtt   3872

ggatcagttc tgtgttagtg tttagctagg tagctgctgt agaatagaag ggtagcacag   3932

ttgaagatat tggtaggaaa gtggttgaag tgatgattat gaagtcttaa ctgaatagat   3992

aaaatcaaga ttggggttgg gtgggcagaa gggtagggat atggagggag aagatgaggg   4052

gttagagtgt cctgtgaggt cgaaggacag gcatagtggg aataattgaa agaatgttct   4112

ggttggacaa ggatctgatg tgggtgtggg agtgagagac tatagtgaat tcaagaaaaa   4172
```

```
aatagactag aacaaaagtt atgtggagat tgcttagtgg gcatttgata gacatctgtg   4232

ggccacatgc ttaaattccc agtgcatttt gcggagttac tggaaggttg gtggcttgtt   4292

tctaccatga gtaggtaaag atggagagca ggatattttg tgagaaagca gctgaagttt   4352

ctataggatg atggaggaat gataggaatg atcacctgaa gttgcagggt ggggtaaacc   4412

tagaagcacc aacaccttct tctgaccctc atgtatttgg aatctgaaag aatgagcacc   4472

ttccaattga aagagttcca agggcattag tatactaaag gatccaaatt gcagctaagc   4532

caaggagatg gaaaggagga ttcagtaaag aatctgagga tgtgaaatat taatttatct   4592

tggaagagaa ttttagagag cacaatggaa tgctttttgg aggagagaaa gagtaagaac   4652

aatttggtta aggtagagga ataacagaac tataaggtga agaaatgaat gtgagacaca   4712

ttagatgacc aaatgatttg atgttcttgg ccatgacctg aattaacaag actgtgaggt   4772

aaaatggatt taatcggcta caaatcttaa gataaccaaa acctgagctg tttaatatgg   4832

tagcactagc actaaccact tgtagctatt tatatttaca ttggttaaaa ttaaaatgaa   4892

aaatttagtt cttcagttgc actagccaca cttcaaatgc ccgaacatag ctacatgtag   4952

cgagtggcta ttgaactgga cagcactgac agcatgtcca ttatgctaga aagtcctatg   5012

ggacagcact ggtctaaaca gtgcatggta tgagagaaag ggcaggttaa ggcactcagc   5072

ttcactgact ggggtggaga ttctgatggt ttgtactcag gttccagatc cctgaggctc   5132

aggaaccttt gcagtttagt ctggttacct gtggcccagt ggttacaaca gaatgattaa   5192

cagtcaattc tttgcatctc tgggtggctc aggaaaaatt taaggagtta ttagctgtga   5252

actaacctta agtaagttaa attaaaaaaa aaaaagttct taagctaata tgattttaaa   5312

tatctgcact gaagtataat gcaaatttaa attcagcata attatttgct tgttgttgac   5372

tcatttgaac ctcaaaatat aatgggatta atttatactt tgggtttatt actttaag     5430

atg gct cag cag tct gca ggt gga cga gat act cgg ttt tta cgt aat     5478
Met Ala Gln Gln Ser Ala Gly Gly Arg Asp Thr Arg Phe Leu Arg Asn
100                 105                 110                 115

gaa att tgc caa ctt gaa aaa caa tta gaa caa aaa gat aga gaa ttg     5526
Glu Ile Cys Gln Leu Glu Lys Gln Leu Glu Gln Lys Asp Arg Glu Leu
                120                 125                 130

gag gac atg gaa aag gag ttg gag aaa gag aag aaa gtt aat gag caa     5574
Glu Asp Met Glu Lys Glu Leu Glu Lys Glu Lys Lys Val Asn Glu Gln
            135                 140                 145

gtaaagcact tttttttcc atgaatcttc actgttcaag ttacctggct ttttattatt   5634

attggtaaca atatcaattt ttatattgta tgttatattt gaaaaatgat gtacacttat   5694

ctctaaggtt ttatatcact gttcattttg tcatcaccaa ttttaaaata taatggtact   5754

tctagtgaat atgacttgaa gattaattct ttatatttgg aagtacattt ttctcaggac   5814

atcaaacttg ttacctaaaa ttaatgcttt tgtctggaag attggtatca agtaactaat   5874

agattttcat aaagaagtga tctttctagt gccatagttt attttgggta aaagttatat   5934

ttgttcattt caatgtattt atatgattag tagattcgca aatgaatctt tcgatatatt   5994

caataatggt taattaaata tcttgttttt ggttgtacct tattttatgt gagatatata   6054

tatatatgta tagtttttga aaagttgtgt tcatgtcagc agtttataaa tcacatattt   6114

aaaataacat ttttaatgca tagtttttat tacctcgtta ttccttgtta taaactaata   6174

attcttgcag tgttcacttg aatttagttt taggaaaaaa gttttttgca gatcaacttg   6234

tatttcctgg aagaaaattt cctattttac ctcagcttcc tatttaatgt attatttatt   6294

tatttactta acatttattt gtttttttatt tcacctgaac tgttagtaaa cttagtaaaa   6354
```

```
tttggtgcct acatgtggta actgtcctgt cccttatact cagaaacgtt ttccaccttt   6414

gtgtccttta ggtcattgtt gtgttatatt ccatttattt tattttgtcc attgttctct   6474

cagaaattga gggtcataca ttttaagaaa acaatgatat gctatttaag agaatgtatc   6534

ataaattgat ttgtaaggaa aagtatcccc attcttcatg tatgtatttt actctaaaat   6594

gttgaagaat catatagaag ttagctatga aaacaatgtg gtagagaaag tatggatcga   6654

tgccacttaa atgttaggaa gaagctctta gagcattatc tgtttagcta actgcaaaac   6714

atagcagaca tgtggatttt ttaatagtca tcaaggatct aacttataat atacactggt   6774

agaattgctt agggggatgt ctgtggtttt ctggactttt gttcttctat atagacctgt   6834

atcagttgac ttatcattca taccacacac ccttagctaa tcagaactac cttgtccatt   6894

tatatcttag actattgtct tttttcatag tcacacacag agaaaacttg aatatatggc   6954

ctgtgttcct ttttggctgc tcaattcctt gagatgaaat atgggtatgg gttgctttgg   7014

caattacttc tttgccgtta accagtcatt cagttttatt gagtctttac agcataccag   7074

aggctgctag ttactagtga tatagtgggc aactatgttc tggttctcaa gaatattcat   7134

agtcaataat aagcataaca tagtgataat atgatactta gggagataca taaggtcata   7194

ttctggcata ctctggagag agataccgta atcagccttg aggtgcagga tgtgatctgt   7254

aaactgagac ctgaagtata gttagactgg taagaggaat gaggatatat atggtggtta   7314

ataaaagaac attctgggta gaagatatag catttgctaa gacctagagg taagagatgt   7374

tatggagtat ttaggaaact acagttattc attttgactg aaatataagt gaaaatagct   7434

ttcatagagt ccttactatg tgccaggcac ttcatatgca ttaattcatt attgcttatt   7494

tgatacttgt catatgagat agttgtcatt tctgccatga tacagatgaa gaaatggaga   7554

cacagaaaga gtaattgccc atggttgcac agcttataaa tggtaaaggt aggatttgaa   7614

aacagtctta ctcaagagtc tgtgctatct tgccttccca gttttatttt ttatgatcct   7674

ctggagagat aagcaagggc cagttcctaa tgaatttggt tcttttcctg aaaggagcca   7734

gtgaagagtt ttgagcacag gatatcatga tcagatctat actttaaaag tttactgtac   7794

tttgtagaga gtggattgaa aagggccaag actagtaagg aaacatttgt gttaattcag   7854

ggaagtgcta atgatggcat ttgcctgaga aagacaagtg tgagagaagt agatgtaatt   7914

ggatgtggtg aatgtaattg gttgttggag gagagggagg atggagagtc tgcctaattt   7974

tgtgggttgg gccactaaat aggtagatag tgccattcat taaggaggaa cacaagagga   8034

atttggaaag cttgagatta tttcagtttt gtagatgttg agtttgaggt tcttctgggc   8094

atattcaaaa agggtatctg tggatatgga attcacaaga gaccctgtac agatgatgag   8154

gatttatgaa tcatcaatgt agacattatt gaagccagag aagtgattgt aaggcacgtc   8214

tctgagaaat gtctaataaa gcaatgaaat aggaagagtg cttcaaggaa aagctcaaga   8274

aaggagaaac agagtgtgat gtttgagaag acaagggaaa aaaacattaa tagcattaaa   8334

tgctttagca ttaagttctt ggcttctctt cttgtaaaaa tttcccaatt cagaacacag   8394

tgggattatt aactttcaat tgataataat aatgataggc aaacttctaa aatttgtatt   8454

gtagtttgca ttttattata aactttcttt aaatttttat tttgaaaaat gtcatatctt   8514

cataaagatt gtaagaaaca cactgttggt gttaatgtaa attagttcaa ccattgtggg   8574

agacagtgtg gcaattcctc gaagatctag aagcagaaat accacttgac ccagcaatcc   8634

cattactggg tatataccca aaagaatata aatcattttc ttataaagat acttgcacac   8694
```

```
atatgttcat tgcagcacta ttcacaatag caaagacatg gaatcaaccc aaatgctcat   8754

caatgataga ctggataatg aaaatgtgga acatatacat catagaatac tatgcagcca   8814

tcaaaagaga atgagaggtc aagcgtggtg actcatgcct acagtcccag cactttggga   8874

ggccgaggca ggcagatcac ttgaggtcag gagttcaaga ccagcctggc cagtatggtg   8934

aaaccccatc tctacaaaaa caaaacaaaa caaacaaaaa ttaactggtc atggtactgt   8994

atgcctgcag tcccagctac ttgggaggct gaggcaggag aatgacttga acccagaagg   9054

cagaggttgc agtgagctga gatcgcacca ctggactcta gccttagcaa caaaactaga   9114

gtttgtctca aaaaaaaaaa aaaaaaaaaa ccggaacaag atcatgtcct ttgcagggac   9174

atgggatgga ggtggaagcc attatcctca gcaaactcac acaggaacag aaaaccaaac   9234

actgcatgtt ctcacttata agtgggagct gaacaatgag aacacatgga cacatggtgg   9294

ggaacaacac acactgggac ccgtcaaggg gtcggggtgg gagaacatca ggaagaatag   9354

ctaatggatg ctgggcttaa tatctaggtt atgggttgat ctgtgcagca agccaccatt   9414

gtacacattt acctaagtaa caaacctgca catcttacac atgtacccca gaacttaaaa   9474

gttgatggga aaaagaaaaa caataaccac ccacataccc ttcatataga ttcaccagtt   9534

cttaatgttg tgccaacttt gctttatctt tttgtcagta tttttacaca cacatgtatt   9594

tctctgtctc ttgtttgttc aatcacattt tttgctgagt catttaagag ctaattgcag   9654

atatgatact ttgcacttaa atatttcagc ttgtctgttt gaaaaagaaa gatgttctcc   9714

tacaatgaac acaatataat tgtcatgctc aggaatttta atattgattc aacaccatta   9774

tctagtccat aatgagattt cttctaatgg cccaataata tccttcagtc tccccacctc   9834

caatatccaa agttctgtca aggatcacat actacatttg gttctttatt atagactttt   9894

taaatatcgt tgtataccat tgtgattcta tcgtctcctt taataaagag gagaaccaga   9954

aaaatgaaag gtcataagag gaatgaggtt tggagaatag gtgaaaaaag gcatcataat  10014

gtttataata atgtttgcct gttcagagaa acaagaatca cagataaagt cacttatatg  10074

tagataagag aatgctgtat tactttttgc tattctattc actgatcatt tttctaagaa  10134

ctctgtatgc ttcttgttta actcttatgt cagcatgtat gagaaaactg agttaaagag  10194

atgttaagta actcattcat gctttactag aaattggttg atgagggaca taaacctagg  10254

ccggtgtgat tttagattgc ttcttttaac cattgtgttg tattgcctta tatttctaag  10314

taatttatgt tcactgagag caaataatag tctagctatg acttagaaaa gtaaaataaa  10374

gatgttgggc agaaaaccat tttattaggg gtttttttgg aggagcagat taatttgttt  10434

ctgtattctt tggttagttt gtgtgtgtgt tctttttaat tctttaaaat gaaactgttt  10494

aatccttaaa tccttaagtt ttgaaaattt tggcctatta tttatgtgtt aggttgatat  10554

taaatcctta atagctttaa cattttctac tttgttagag aggatttaaa atttaagtag  10614

ataagctgaa tatctggctt tatattaaat tactgctgat ggccaggcac agtggctcat  10674

gtctgaaatc ctagcacttt gggaggttga ggcagatgga tcacttgagg ccaggagttc  10734

aagaccagcc tggctaacac agtgaaaccc cgtctctact aaaaatacaa aaattagcca  10794

gttatggtaa tgcatgccag taattccagc tactcggtag gctgaggtgg gagaattgct  10854

tgaaccggga ggcagaggtt gcagtgagcc gagatcgcac cactgtactc cagcctaggc  10914

gacaaagact ttgtctcaaa aaaaaaaaaa attactgctg aattttatct tcttcttatt  10974

tatttttttt ttttactatt ttag ttg gct ctt cga aat gag gag gca gaa     11025
                            Leu Ala Leu Arg Asn Glu Glu Ala Glu
                                    150                 155
```

```
aat gaa aac agc aaa tta aga aga gag gtaaaaaatt ttagtagttg         11072
Asn Glu Asn Ser Lys Leu Arg Arg Glu
            160                 165

tggtggttca acaaaggtac ttattaaaat aagtacctaa gtttacataa atttatattt  11132

taaccaggac tggagtcttc taagtaactg atgttttcag actgatttta tggtatgact  11192

ttgtctcagg gaaatagaaa acaaagcaaa atgtgaggcc attaagtatt acattcatct  11252

caggtctatg cgggtaaatc tttttttgtt gttttataag ccattctttg ctagttttct  11312

aattgaatag atgactggat ttctattctt atttctctta cccagaatcc tttaaaattt  11372

tttgttactt gtggaatctt ataaattctg attatcattt ggttctactg agccaaataa  11432

tgtttgtaca ttgtttattc tgatagaagt tcttaagttt ctaacataat tgaaatatta  11492

tttgttttgg tagataatta gtattctttc tttggttatt caagataata tgcatcattt  11552

tcccaaaatt tttttgtttt ctttagtttc tgattattat ttttaattat gtattacctt  11612

tctcatttct aattaccgtt ttcctgtcct tttctgtag aac aaa cgt cta aag     11666
                                          Asn Lys Arg Leu Lys
                                                          170

aaa aag gtgaggcttt aagtgtggtg aaatcttggg aatttaaaat atgttgtgag     11722
Lys Lys

agcactattt agaggatatg attttgttat tctgaatagt tttgtaattg aatgttgtgt  11782

ttggttacct tcag aat gaa caa ctt tgt cag gat att att gac tac cag    11832
                Asn Glu Gln Leu Cys Gln Asp Ile Ile Asp Tyr Gln
                        175                 180

aaa caa ata gat tca cag aaa gaa aca ctt tta tca aga aga ggg gaa    11880
Lys Gln Ile Asp Ser Gln Lys Glu Thr Leu Leu Ser Arg Arg Gly Glu
185                 190                 195                 200

gac agt gac tac cga tca cag ttg tct aaa aaa aac tat gag ctt atc    11928
Asp Ser Asp Tyr Arg Ser Gln Leu Ser Lys Lys Asn Tyr Glu Leu Ile
                205                 210                 215

caa tat ctt gat gaa att cag gtaaaatggc tagaagtcaa ttcagagcaa       11979
Gln Tyr Leu Asp Glu Ile Gln
            220

tggttcctaa aaactttaat ttcattacaa tgtaaatata atatttagcc ctacatgtaa  12039

attccctggt ataaatctgt cactatgtac ttgtaaaatg tgaaataaat tacatctttg  12099

aagttgcaac tttttagcca tttttatatt tgcctgtctt ggtcattaag aacaattgag  12159

gtccttatgt actattttct tgattcaatt tgatttaatt ggtcaatgcc aattagtaaa  12219

ggtctataaa gaattctctt tttttctaga ggacacttat ggctgcgttt aattttaatt  12279

tggtttaaat ttcagttttt ttaaaattac tttttaatta tagtgtcttt aacttttttta 12339

g act tta aca gaa gct aat gag aaa att gaa gtt cag aat caa gaa atg  12388
  Thr Leu Thr Glu Ala Asn Glu Lys Ile Glu Val Gln Asn Gln Glu Met
      225                 230                 235

aga aaa aat tta gaa gag tct gta cag gaa atg gag aag atg act gat    12436
Arg Lys Asn Leu Glu Glu Ser Val Gln Glu Met Glu Lys Met Thr Asp
240                 245                 250                 255

gaa tat aat aga atg aaa gct att gtg cat cag aca gat aat gta ata    12484
Glu Tyr Asn Arg Met Lys Ala Ile Val His Gln Thr Asp Asn Val Ile
                260                 265                 270

gat cag tta aaa aaa gaa aac gat cat tat caa ctt caa gtaagaatta     12533
Asp Gln Leu Lys Lys Glu Asn Asp His Tyr Gln Leu Gln
            275                 280

cttttagaat aacttattta ttcagacttc atattatctc attactattt atttgacact  12593

agaaagtact ttttctagga tgtgaatttt tgtctgtctt tttaatagtg taatatcttg  12653
```

```
tcatgttggt atatttgtcc atatgtgttt ctccaatcac ctcacaaaca ctaatttttg  12713

caatttagga tatataaatg atacttgaat gaatgtgtag atagcagtca ttatggggtt  12773

ttctataaaa gactactgaa aatcctgtgg atcataacat ttcattttat cttaaaataa  12833

atacattata aatgtattag aaaccaatac attgttcagt atttatgtgg attaaatttg  12893

tttaaaaggt agaataatgt ttaaaaataa aattttctag taatgaaaga taattatgca  12953

attataagat gcagaaacta ttaaatgtca cctataattc caggatgact tcaatgataa  13013

atacacatat gtaatgtaat gtatccgtat gtatgtgtat ataagtatga atacgtatgt  13073

gtgtgtatgt agatatattt atatatataa tgtatatgta aatatgcaca ggtgtaaata  13133

tatgttacat cagtttgcaa caactcttga aataactttg tcttttag gtg cag gag   13190
                                                     Val Gln Glu
                                                     285

ctt aca gat ctt ctg aaa tca aaa aat gaa gaa gat gat cca att atg    13238
Leu Thr Asp Leu Leu Lys Ser Lys Asn Glu Glu Asp Asp Pro Ile Met
        290                 295                 300

gta gct gtc aat gca aaa gta gaa gaa tgg aag gtattttttt tcaattgaca  13291
Val Ala Val Asn Ala Lys Val Glu Glu Trp Lys
    305                 310

taataacttt ttctttttgt attttagatt taaattttag tcttattttt ctttaaatgt  13351

cttatactgg tttataacac gtttattagg gtttttaaac ataagtttat tttatttatt  13411

ggttagaaaa gctctagaac tgtccttttt gatctctagc taatttgtta ttgaatgacc  13471

tctttcacat caatgagttt aactttaaac tttttgatag aagtctaact ccaaaatata  13531

tttggcatct aaaatatata attcgaaata taatttaaat ttttttactt aactcatagt  13591

taccttatat acattagtta aatagttgca ggtttaattt tagtttttct aactaaatgt  13651

caggttcatc agtgggaatg ggaataagca aagggatcag aataacttgg gaagcctttt  13711

caaaatacac ttttcttcct caccaccact ctccaacctt aaccaaattg tcaggcctta  13771

ccatattaga agctgggatt atgatggttg tatacttgaa aaacatcaga gattattctg  13831

aatgaataat tctaatttta aaaactatca cttctagagt cattgctttc tagtatggtt  13891

cacataaatc ttgtgggcag tttggaactg gttagcatct agggagctca gataacctat  13951

attttaaaca aaagcattag caatggaaat aaggcctata gaatcagtca tgtctccata  14011

aactttatat aaagggccag acagtgaata ttttagacca cctggtctct gctataacta  14071

aactctgctt atagcatgaa agcagccatt gacaatacgt aaatgagtga gcaaggtggt  14131

tttccggtaa aattttattt acaaaagcag atgggaggcc agatttgacc tttgggccat  14191

agtctaccaa cccctggaaa aaacagttgt ctttaccaga ttgaatgttg gcagggtaaa  14251

tggtgacatg ttatatgtat tctgtacttt gttttgactt aataccattt cataattatt  14311

ttatatcagt acgtatagta ttgctgttct ttttaaaggc tatgtaattt ttctttttat  14371

acaggtgtta atttgataat ttgtgaagtt tatgaagttt ccaattttgg ggttgtaaac  14431

tgttttaatg aatatcctta tatatgttat tttgcaaatg tacaagtata tctgtggaat  14491

aaattgctgc aagtgttgta attgtcatgt atgttgcaaa tacattctaa cagtttgtca  14551

ctttttttgc tttatggcat tttttgctgt gaaatatttc tttttatgct tagttaaatt  14611

tattattttt taatgacttt tgacatttgt tataatgaga aaggcttctg agtataaact  14671

tgttttctca tcttttctcc taatatcttg ttttgttttt gtttttgttt ttgtttttga  14731

gacagagtct cactcagttg cttaggctgg agtgcaatgg tacaatctca gctcactgca  14791
```

```
aatgccacct cctgggttca ggtggttctt gtgcctcagc ctcctgagta gctgggatta  14851

caggcatgtg ccgccatgcg cagctaattt ttgtagtttt agtagacatg gggtcacact  14911

gtgttggcca ggctggtctt gaacccctgg cctcaagtga tcctcctgcc tgggcctccc  14971

aaagtgctgg aattacaggt gtgactctgc ctggcctttt tttacattta aatcttcgaa  15031

acatataatt cattttgatg taaggagtat catgtggatt caacagagct actctgttgt  15091

ccaaacatct tttattgatt atttcatctt ttattgaatt gattgatcta ttttctagca  15151

gtgtatactt gttttaattt gtgtatgttt taatatctaa aaacgttatt atttttctgc  15211

ttttagactt ctttatgaat atttttaatg tgaattatag aactggcttg tccagttctt  15271

aaaaaatatc ttgtggattt ttattgggta tgtgttaaag ttataaattg ttttatagat  15331

tgatttagga taaacctttt tatgttattt ggtccttcta gctaaagaac acaagatacc  15391

ttttctttca ttcattcaag atattttatg cctcttggtt gcattttaat gcatacttca  15451

taaagatcaa ttgtataaaa cttttcacag ttgtatggaa gtacttcttg tttataaatg  15511

agttttgaaa ggttgaaata tttttaaaga ttgaattata aaaaaagaaa attcggtata  15571

tattttaaaa tcattttcta tttgaatttc aggttgtata tacaaaagga acagagatta  15631

tgccagtagt tgctcatact ttctcatttc aaataatttt tattttctgt atcataaatc  15691

tactaacggt gtttattatt tatgataatg aagaatgttt tattaacttt ccttttgcat  15751

aacagattct attgtgttta tttctag cta att ttg tct tct aaa gat gat gaa  15805
                              Leu Ile Leu Ser Ser Lys Asp Asp Glu
                              315                 320

att att gag tat cag caa atg tta cat aac cta agg gag aaa ctt aag    15853
Ile Ile Glu Tyr Gln Gln Met Leu His Asn Leu Arg Glu Lys Leu Lys
    325                 330                 335

aat gct cag ctt gat gct gat aaa agt aat gtt atg gct cta cag cag    15901
Asn Ala Gln Leu Asp Ala Asp Lys Ser Asn Val Met Ala Leu Gln Gln
340                 345                 350                 355

gtaaaatctt aacagaattt tgtttatcaa ccagttttat tacagttgga actctgaacg  15961

atgtctttta tttattatat catcagtgcc tagtgtagcg gctggtacta ccaagtgtat  16021

aataatgtct tttgaaattt cttctaccac ctggtcccaa taaaaaatta gaattaagtt  16081

tagatcacgg attagactta gaactagagt tactgtgttt atttttctat gtttatgtgg  16141

atagtacaca cattgttttg gttagaaatt atttaacaag aaatgattaa aaacttttag  16201

aaatttaaaa taattttata ctcttttaag gtttatttta ctgtatctta gtcctaacat  16261

accctataca atgtgaaata agctaaaagc atggttataa tttgactgtg ctacctattt  16321

tatttttagt gaaaataacc caaataaaag gaagtaatac ttttattatt tgtgctgtag  16381

ttatagtcca caagtaagaa gatgatttga aaagtgtatg ctgaataaga acaattacag  16441

gggacaacat tttttaataa agtacgaaag gggaaaaagc taagttgaat aaaagagaaa  16501

gcacagagca aaacagaaac atacaaaatg gtaaaaaggt ggaattgaat ggaggatgag  16561

gaaagtaaca tataaggaag tatagaagcc ataaacatta gggagttctg gaaatcctat  16621

tttccagagt gttagccatt atatccatct ttcagtattg gagtaacagc agtgtaccta  16681

tcattgtgta ttacagttga agtgtacaaa atggtaaaag gcatacttgt acccacaaga  16741

aaatatgttc tacagtcttg ttgaaaaaaa tcagacgtac tttttccctt accttttttag  16801

gttaatattc atgaagggat atatattgtt ttaaaatatt ttatag ggt ata cag     16856
                                                   Gly Ile Gln

gaa cga gac agt caa att aag atg ctc acc gaa caa gta gaa caa tat    16904
Glu Arg Asp Ser Gln Ile Lys Met Leu Thr Glu Gln Val Glu Gln Tyr
```

-continued

```
    360                 365                 370

aca aaa gaa atg gaa aag aat act tgt att att gaa gat ttg aaa aat    16952
Thr Lys Glu Met Glu Lys Asn Thr Cys Ile Ile Glu Asp Leu Lys Asn
375                 380                 385                 390

gag ctc caa aga aac aaa g gtatttttat aaatatatag ttattttata         17001
Glu Leu Gln Arg Asn Lys
                395

tacaattatg tttttaacga ctttattttt attaaaataa aatgtcaagt caatattgag  17061

ttttctccat ttgaatttta tattttcaaa aaattgtaca agatatttat tattatactt  17121

atattactag tgcttacatt tgtaaatgat ggatgcattt tctattattt ttctcctctg  17181

gtgaaaatta cattaacgtt tattaccagg tcactggtat gaaagaaatg aaaaattgtg  17241

atacaattat ttttatttaa ctttttataa ttaacaaaga atggaagata ataaaatttt  17301

gaccagtgta acagcattgc agatagtttt cagaggtaat ttcacattaa tcttacccaa  17361

attaatgttt catcatattc tccttaccct gagccatatt acctttttta acacatcaaa  17421

ttctatgaat ataagttctt acaatatctg tgttgttata tttccatagc actacatact  17481

atagttatgc cagggcacac tagtgcgaac tgttcatggg aaattcatgg acatgtttat  17541

tataattggt gactatgtat atatgtatac actacattta tacacacgcg catggaatca  17601

ctatttcttc ttcatgtcat atatatatac atatatacac atatatatac atgtcatatg  17661

tgtgtgtgta tatatatata tttgtatata tgacatgaag aagaaatagt gattccgtgc  17721

acatatgtgt gtgtaagtgt agtgatgtgt ttgcaggtac ggttgtaatt tcaaaaatga  17781

agcaaaagcc ttgctcagga gataattgaa ccaatactta aaggaagtaa aggagtgaaa  17841

catgcagatg gctctaagca gtgggaataa gttcaaaggc agtaaagcag gagtgtacca  17901

atcatgtctg agaacaacaa agaagtcttt ttggctggag tagagtcagc aagtgaggca  17961

gtgataagac cagagaggta aacagaggcc atatcatatg gggccttata gttcattgtg  18021

cagacttggc ttttaagtga gaagggacac cggggaaagt ttctgaagat agaaatgata  18081

taatttgact taggctgtgt ttgcagtaga ctgtaggagt ggtaaataag aatcagggag  18141

acctgttaga agactattgc aataatctgg agaaaagtga tggtggtttg gggcatggtg  18201

gtagcagtgg agttactgga tgcagcagtt ctggatgtat tttgaaagtg ataaaaatgg  18261

aatttgctaa cagatcagat gtaggatgtg agagagagag aactcttggt ctgaaccaaa  18321

agttttggtc atggtggggt tgtgggaaga gcaggttgag agataatcag gtacttaatt  18381

ttagacatgt taggtttgag atgcttatta gacattcaag tgaaggtgtt aagtaggcac  18441

ttgtatataa aagtttaagg tttaggacaa caatctaggc taaagatatg tttggtaact  18501

gtctctgtaa aagtaattga aataatgagg ctggctaaga tcaccaaggg agtaaatgta  18561

ggttaagaag aaaaatctaa agagcttcta ctttagcagc tggggagata aaaaggagct  18621

accaaaggag actgaaaagg aaagcccaga gagctaggag gaaaagcagg agtatggaga  18681

gccctgaaaa ccacatgagg aatgtaacca aggaagaaga aacaactgct ttcagagctg  18741

tgttcattgc tgctgatagg tcaagatgat cactaaaagt tgactattgg acttagcaat  18801

ggtcattttt ggttcaagag aaaatgggta gagaggaaat gtaataaaga aatataggaa  18861

ccctttccca ggactgtttc tataaagaga aggagaaaac aaggtggtag cttgagggga  18921

aagagggatt aagaaaacat ttttctcttt aagatggaag aaataactca tgattttagg  18981

ttaataggag agctccatta aagaagaaac attaatgaat caatgaagtg gagagagaga  19041

acttctggaa caataatatt tttaagaatg caatgggatg ggatcctagt gtgccagtga  19101
```

```
agaggttggc cttaactagg aacacagagt tcatccataa ttgtagaaaa gaaggtagag  19161

tgtatagata tcgatgtagg tggcttggta gacatcctgg taatgggaat ttgtggaagt  19221

tctaaactgg ttgctgcttt tttctcagtg aacaagggag caaggttctt agctgaaggt  19281

gaggatagga gaagatgttt cataagtttg aggagaaaga agagaagtga aagtataaaa  19341

tggtcatctg aaagattgaa gacgtggaga atgtggtatg actgttgagt aacttcaaga  19401

gcccacgata tatatatgta tttctattta tgtgtttatt atatttgtat cagaacactt  19461

tgaaagtagt ttaaactgct ttaaaaggat gactaatagt atggattgtg cgtattctaa  19521

ttactaggag aaaaagtggc aattgatctc tgctgtcaaa taaggaaaag gacttatctg  19581

ataacacttt agtcagtccg tagttatata atccctaaag ctcacagaag gtgtgtgtac  19641

tagactgtac tctacatctt gaacttaact tgtaaaacgt aatggctaat ggtattcttc  19701

cttcataaga ttaggattag gtttagttat caggaacaga gagctgaaga ataatggcaa  19761

aatcaagata gacatttatt tctcatctat gtaatggcct agaattaagc attccagggt  19821

gttgccttca tctgccccat ccaaaatgga tggaatgcag ctttatctca tgtctgtgtc  19881

ccaaacagca agacagagga agaggggcaa gagttaaaag catgtgctga aggataggca  19941

ggtaaatata gtgtttattg tgtagggcca tgtggaagaa tgataggaga atagatatgt  20001

ggatggaagg gagaatagat actgggggac aactcagcct gtgtcatgtt ccacagctta  20061

gatgttagct ccagacagct gtgctcattt cttaaaaact tttgtgatct caaacgtact  20121

agttttatgc ctaagtccaa tattaaatat ataacctata tattagtaaa tgcttataat  20181

gaatgagtgt gagaatgatc tgtcaatcaa ttttggaatg atagcaatat tatgttttgg  20241

tcttttaaca atttagtaag atattacaag taggcattta ggaagttttt agcttagttt  20301

ggattaaatt tagctgcaag tgacagaaaa atcaagcata atacaataat ttaaacaaga  20361

tagaaattta tttctctata atatagacaa agttgaagca actagggcag gatttgtgtg  20421

acagatgctc aaatatcccc tatcaggaac cctgtctctt gttgctgtgc ctatctcaac  20481

atgtggtttc taactcatgt gaagttgcca ccctcatatc catgtggatt tcagctagca  20541

ggaaggagga aagagaagag agattactcc tttattttaa aaacattttt tttttttttt  20601

ttgaaattca catatgaact ttgcgtttat attccattac tgacatgacc acacatagct  20661

gcttgtgtgt aagtggaaat ttagttcttt atttcaaatg gccacgtgtc aagctaaaaa  20721

tccatagttt tagtacagtg gacaaaaggg aggttaaata ttaggaacag ctagcagtct  20781

gtatcacaat gatcattttt tgtaaagcag tattttgcaa ccttttaaaa tccatacccc  20841

ttcagctaag aaggttttac tgaacttcag ttttttagta aattgtatta gtaaaaccaa  20901

aacaaaactt tcatcttaca aatataaaat gacaacttta aaggattttt ttttaatggc  20961

ataccacttt tcttgccacc atgttgggat cactgatttg aaggaataag tagtcaattc  21021

aattcatgat ttttgttttt actctgtag gt  gct tca acc ctt tct caa cag    21073
                                 Gly Ala Ser Thr Leu Ser Gln Gln
                                             400

act cat atg aaa att cag tca acg tta gac att tta aaa gag aaa act    21121
Thr His Met Lys Ile Gln Ser Thr Leu Asp Ile Leu Lys Glu Lys Thr
405                 410                 415                 420

aaa gag gct gag aga aca gct gaa ctg gct gag gct gat gct agg gaa    21169
Lys Glu Ala Glu Arg Thr Ala Glu Leu Ala Glu Ala Asp Ala Arg Glu
                425                 430                 435

aag gat aaa gaa tta gtt gag gct ctg aag agg tta aaa gat tat gaa    21217
Lys Asp Lys Glu Leu Val Glu Ala Leu Lys Arg Leu Lys Asp Tyr Glu
```

```
            440                 445                 450

tcg gtatgtattt ttatcttgtc attcaaggag cttagaatta ttcttgccat        21270
Ser

tcacagacta ttctgtgcta tttactgcat accatttaaa aaacattcca taagtatctt  21330

ttgataaaga ttatcctcat taatttatac taaactattg aaacctttga gcatttactt  21390

tttgccagaa ttgttttcaa acttttgatc acagtgattt gtccaaataa tcagttttgg  21450

tgaagcagca ggattacttt tttttattat ctgtgttcat tgggccacca tgtagatgtg  21510

acaccactgg ccaatttgac agaatttatg acaggaacat actgtgtcaa tacaacctgc  21570

tctccacttt ttatactttt tcattggtta caactaattc aagcaactaa tgacttactt  21630

attctactgg tattgctgat ttgcttttac taattctttt agtattttgg taagtgtttt  21690

ttatatgtaa tgcatattca gagtcacttt gcctttagga tattatactg gaaagtttta  21750

actgttgcat attacatcat tattattact ggatttggtt tataaaagca caataaaaaa  21810

ccagtgtaat gatataaatt ataggcatat gtacattttc ctttagactt agtaaaaaaa  21870

aaatcatgaa cttgataaat ttattcaagt aaaccatgtt atattttaaa ttaaattgga  21930

tatttttcag gga gta tat ggt tta gaa gat gct gtc gtt gaa ata aag     21979
           Gly Val Tyr Gly Leu Glu Asp Ala Val Val Glu Ile Lys
               455                 460                 465

aat tgt aaa aac caa att aaa ata aga gat cga gag att gaa ata tta    22027
Asn Cys Lys Asn Gln Ile Lys Ile Arg Asp Arg Glu Ile Glu Ile Leu
            470                 475                 480

aca aag gaa atc aat aaa ctt gaa ttg aag atc agt gat ttc ctt gat    22075
Thr Lys Glu Ile Asn Lys Leu Glu Leu Lys Ile Ser Asp Phe Leu Asp
        485                 490                 495

gaa aat gag gca ctt aga gag cgt gtg g gtaagccatg ttttaagtta        22123
Glu Asn Glu Ala Leu Arg Glu Arg Val
    500                 505

catagtttgc gcaacctgat ttacaagtct tttttttaa tttaaatttt gtttattatt   22183

atttattaag tagtttaatg ctttttcaa atgcttttat aaaacattta atacaaataa   22243

aagtggagct aacctgattg aagtggaatc agattttatg ggttggagt ggtgggtggg  22303

cagggctgga acattgcttt atttggtcta gcatctcctc agtaatagct gcttgtttaa  22363

aaagatgaaa gtttattaat accacatatc agagattaac cttttttttt cccaacaaaa  22423

gtagggtctg tattacccat gtttgtttgc aaaatgctct tgtaacagat gagatattta  22483

aacttcttgc tctgtgttgt gattctcctg cctctgcctc ctgagtagct gggattacag  22543

gtgtgcacca ctatgcccgg ctaattttg tatttttggt agagatggga tttcaccatg  22603

ttggctaggc tggtctccaa ctcctgacct taagtgatcc acccgccttg gcctcccaaa  22663

gtgctgggat aataggcatg agccaccgcg cctggcctgt taaaatcttt taaagatttt  22723

taagtacttg atttttataa tttagactac ttacgtttta ctttgttcga gtattttaag  22783

gagtaattag taatatagct tgagagttta tatatttatt ttaataaata gcctattagt  22843

taatattact aatttgagtg ttatgatagt gcagactaag ttgctgcttt aaaatgaaaa  22903

taaatatcta aatatcaatt tcattattgc taaatttcat ttaatgcttt cttagttaaa  22963

aatgatcatt tgtaaaaact attatctaaa gaaaagacaa atagacaaat aagtatttta  23023

tacagatata tatgtgtgaa aagtatctaa cttggatccg tagttgtgct aggaccccaa  23083

attagacttc tgatcaactt ggactatcag atcacagcct tctgatcaac ttggactatc  23143

agatcacagc caagaatctg gaagttccta aagatgactt ctggcccgtc taggtagctg  23203
```

```
tcatagacat catattttct gtgcttaaaa agctccaaat cttggtttat aatttcattt  23263

aggtttttgt taggatttcc attaataatt gtgataaaat tttaacttgg gttacagttt  23323

aaatatctgg aaaattcttt cacagaaagt tacctcattc ttcagtgata ctggctaagt  23383

gaattataac cagttgcttg atggtatatg acatttttgc agcttatttg aatgtttttta  23443

agtttttaat tatattgctt tctattgtag gc  ctt gaa cca aag aca atg att   23496
                                 Gly Leu Glu Pro Lys Thr Met Ile
                                         510                 515

gat tta act gaa ttt aga aat agc aaa cac tta aaa cag cag cag tac    23544
Asp Leu Thr Glu Phe Arg Asn Ser Lys His Leu Lys Gln Gln Gln Tyr
                520                 525                 530

aga gct gaa aac cag att ctt ttg aaa gag gcaagtgtgg tagtcagttg      23594
Arg Ala Glu Asn Gln Ile Leu Leu Lys Glu
            535                 540

attattttct tggctgaact atagagaaat actaataatt tatactttgc ag att gaa  23652
                                                          Ile Glu

agt cta gag gaa gaa cga ctt gat ctg aaa aaa aaa att cgt caa atg    23700
Ser Leu Glu Glu Glu Arg Leu Asp Leu Lys Lys Lys Ile Arg Gln Met
    545                 550                 555

gct caa gaa aga gga aaa aga agt gca act tca g gtatactcag           23744
Ala Gln Glu Arg Gly Lys Arg Ser Ala Thr Ser
560                 565                 570

ttattctaaa cctttaaaaa gaattattga taagtgagtt gtctggatat gaaattattt  23804

gtgtcttagc tgtttttgct gttctattgt ggatctgcta caaatttaat aaatgacaat  23864

aataacctga aggagataag tgagtgtcag tgggttcagt cctgaatctg aaatagacaa  23924

aaacaaaaca aaacaaaata acaaaaacca agcaaacaaa aaagaaaaaa accttagaat  23984

tatggaattt ttgaaaagtt ttatagtata gtattttaat ttctagacag caccaatatg  24044

ttgttattaa taataataaa acttagtagt ttttatgtta atatatgtta ctcaacattt  24104

tccctttcct taaggactat gcattgaaaa gcttttcttg taagttatta ttattattat  24164

tattattaat atttgagatg gagtctgtct tgttctattg cccaggctgg agtgcactgg  24224

tgcgatcttg ctcattgcaa cctccgcctc ccgggttcta gtgattcttg tgcttcagcc  24284

tcctgagtag ttgagactac aggcgtgagc caccacgcct gacttatttt tgtattttta  24344

gtagaaacag ggtttcacca tgttggccca ggctggtctt gaactcctga cctcaagtga  24404

tccatccact ttggctcccc aaagtgctgg aattataggc gtgagccacc atgcctggcc  24464

ttaaattatt cttttctaag tgaaagtaat gttttattga atataaatta acatctttct  24524

tgggtttatt ttacttgagc taaagagaac agttggttaa gttttataat agccattgca  24584

gtgctttttt gtaagaagac cacacagaag gactgtcttt ttcacttgcc ccaaatcccc  24644

aagcacgtat atgagtaata gcagagtggt tctttttagc attatgattt ctataataca  24704

tccaaaactt tctcaagaaa aaacttcatg atttattagt acaataatca gtttactcat  24764

tactcatcat ttatatttac tttatatgtc ttttaactgg tgcttattaa gtagcacttt  24824

aatatagaat aggcaaagaa tggtagagaa gatgaaattc aaaaattagg ttctcacatt  24884

attaatagtt cattaaaagt gagctaaatg agaagcttgt attggctatg tagaattttg  24944

gagggatttt ggaaacaatt attctacctt tgcattaaaa cttgattgta ggttttaaga  25004

attaaagtgt tggaatagta ggagggttat tttaatgttt ttagtttgtt aattctctta  25064

tatatag ga  tta acc act gag gac ctg aac cta act gaa aac att tct    25112
        Gly Leu Thr Thr Glu Asp Leu Asn Leu Thr Glu Asn Ile Ser
                        575                 580
```

```
caa gga gat aga ata agt gaa aga aaa ttg gat tta ttg agc ctc aaa    25160
Gln Gly Asp Arg Ile Ser Glu Arg Lys Leu Asp Leu Leu Ser Leu Lys
585                 590                 595                 600

aat atg agt gaa gca caa tca aag gtaatagtaa agtattgcaa agagagtaaa   25214
Asn Met Ser Glu Ala Gln Ser Lys
                605

ggaaaatatt tttttttttt tttttttttg agacggagtc tcgctctgtc tcccaggctg   25274

gagtgcagtg gcgcgatctc ggctcactgc aagctccgcc tcccgggttc atgccattct   25334

cctgcctcag cctcccaagt agctgggact acaggcgccc gccaccacgc ccggctaatt   25394

ttttgtattt ttagtagaga cggggtttca ccgttttagc cgggatggtc tcgatcttct   25454

gacctcgtga tccgcccgcc tcggcctccc aaagtgctgg gattacaggc gtgagccacc   25514

gcgcccggcc aggaaaatat ttttattgtg ttttcatttc ttccccttt atctcattct   25574

tgaacatcta atcttattat tgttgttaaa taagtagagg gaaatatttg cttatttaac   25634

ctgttgattc aaagattgat taatgagaca ttatttactc tgaatacaga ttaggagttc   25694

agataaagca gagctgctgc ataggagatc atcattcaat accccacagt cagatcagaa   25754

tgagacagaa gagaatatga ccataggatc attatcaaga atgttatctg aaattcacca   25814

tagtgtagaa agtggaatgc atccttttgt ccctttaact agactttctt catccatgca   25874

agttaaagag aattcaactc cagaaactat tacaataaga gagattttta aagcaccatg   25934

tctgcagtct tcaagaaatc tagaatcgtt agtcagcacc tttagtaggg aaagccatga   25994

agaaataaat gacatatgcc ttttttctga tgactgtatg aagaaggtgt caagaagcca   26054

tcaagcacta gagaagacta gttttgtaca aaaaagcaat tcatcttttc atggcttatc   26114

aacagcttca gacataatgc agaagttatc acttaggcaa aaatctgcaa tattttgtca   26174

acaaattcat gaaaatagag ctgacatgga taaatcacaa gtagcaacat tagaagaaga   26234

acaggttcat tcccaagtaa agtatgctga tatcaatttg aaagaagata taataaaaag   26294

tgaagtaccc ttacagacag agatattgaa aaataagctt aaggttaatc ttccagaccc   26354

tgtgtctatt actgcacaat caaaattatc tcagataaat tctcttgaaa atcttataga   26414

acagttacgg agagagctag tatttcttag atctcaggtg agtttttctc caaattatat   26474

ttctgtggtt gttcttttat gacgtctcta acaaagttct gtaacaatta tagttagaat   26534

atttttgttt gcactttaac atcagttata cacattgtac tttttaaaat ctaaaatgca   26594

gtacattgat atgaactcat tgacttgtct aatttattaa atttttcttt agaatgaaat   26654

catagcacag gaattcttga tcaaagaagc agagtgtaga aatgcagata tagagcttga   26714

acatcacaga agccaggcag aacaggtagt gtaaaggcag aacattaaaa gagatgattg   26774

tggtactaaa gacaaaaacc gttatatctt tttgcctctt accatggatg ttgggagagg   26834

gagaaagtgg gattaagatc accatctgct ttactgttta gattttagtt tatttttatg   26894

attgctgcta tgtcttcata gctcgttttt tttgttttgt tttgttatac ttaattgatc   26954

aaacttttct taacttgaaa attatagact tgtgatattt tgttgaaaaa aatcaatttt   27014

attctctctg cttttttcag aat gaa ttt ctt tca aga gaa cta att gaa aaa   27067
                      Asn Glu Phe Leu Ser Arg Glu Leu Ile Glu Lys
                          610                 615

gaa aga gat tta gaa agg agt agg aca gtg ata gcc aaa ttt cag aat    27115
Glu Arg Asp Leu Glu Arg Ser Arg Thr Val Ile Ala Lys Phe Gln Asn
620                 625                 630                 635

aaa t gtaagttaca attatctttt acttttctgt tcttattttt cctatactta       27169
Lys
```

```
aaatcatggg cctaaaaggg cgttaacaca ttctctgttt tctaatctgc tttactccta  27229

attacctctg tactgtatat acttcagtct gtcactatcc agttgatttg ccttgctgtt  27289

ttcattgtga gagaatgtta ctaatatgaa ttttttgtga gaatatataa ctcctttttc  27349

ttgtgtgttc ttcaatcaaa atgaagttag aacaccaaat ttaaaatact ttaatataaa  27409

gcatagttta agttaaggca gaagtatgcc ttatatacgt gtgtatatgc acgtgatata  27469

aataggtctg tcatttaact caactattca cgttggattt atagttgaat ttttttgtat  27529

gtttatttac atttggattt ttccaatgat gtctttggta tatgtgaaat atttgtcatc  27589

tgtatagcat agtgtaaatt gtgaaaaaga tctgatcatc caatgagaaa actgtgtaat  27649

tacag ta  aaa gaa tta gtt gaa gaa aat aag caa ctt gaa gaa ggt atg  27698
      Leu Lys Glu Leu Val Glu Glu Asn Lys Gln Leu Glu Glu Gly Met
                  640                 645                 650

aaa gaa ata ttg caa gca att aag gaa atg cag aaa gat cct gat gtt    27746
Lys Glu Ile Leu Gln Ala Ile Lys Glu Met Gln Lys Asp Pro Asp Val
            655                 660                 665

aaa gga gga gaa aca tct cta att atc cct agc ctt gaa aga cta gtt    27794
Lys Gly Gly Glu Thr Ser Leu Ile Ile Pro Ser Leu Glu Arg Leu Val
        670                 675                 680

aat gtaagttatt tttttcatgt taatgttttt cccctatcac tttagagaga         27847
Asn

ttttctgctg tgtacagatc tccatagttt ctgatgagat atttttagtc atttgaatca  27907

ttgtttccct gtatgtaaag tgtagttttt cttgagctgc tttcaatact tttcttctac  27967

caattggata attgttatta atctgtcttc aagttcactg acattttcct ctttatctgt  28027

gttcttttgg ttcaagggtc agcttgagac cttgaggagt tttttacacc gactttggag  28087

ctcgtttttg ctgactcttt tcttattggg attttccttt cacttatccc atggctttgg  28147

gctgtatcct gtggttttct agatgagaaa gatgatagat ctctgcaatt gcaccctgcc  28207

ctatgactaa atctttaaaa atggcaaagt caatctttgc tggtcctgtc ttccgtattt  28267

gaggggtttt ttcccaaaat ctgcttgctt ttgttcattt tctagaacat ctaggtagtt  28327

ttttttcatt cattttttat ttatgggagt gtagatctct taggaactta tgccatcaga  28387

agtattatga aatggcttta ttctaaatgt ttaaagattt actcattgct acaagaaaga  28447

tttagccatc actaatattc tatatatatt taccatatag ggacttgaga atttcacagg  28507

attcagtatc tgtatataaa cttgaataat atacacattt tagattgtta atatttaagt  28567

atatgtcatt tatgttatct gaacatattt agcgtacatt gtcatattat ttcccaaatt  28627

tgtgcttgat ttcaaatggg aaaaaaattc ttattattta ttgaattgtt tttttaaaaa  28687

aatcatgatt aatcagtaat tggatacttt ttaaaataac actataattg ttaacagaga  28747

atgagagtga tactggtatg ttaaaaactt cctgaggcaa gaaaataatt tgattcccat  28807

tatatctttc tcatactgac tttccttctc tgattggtga ttttgttttg cctctgccac  28867

tttgaatgtc taaaatgatt ctttatgctt tttttatgtg aacatctttt gtccgtgatg  28927

atgcccacta ctgatactgt gtcccagatc aaacttaatt ttccaagggc agctctactt  28987

agtgaccaaa tgaaaacaca gtgaatagcc caagaaatcc taacttctat ttatgttgac  29047

aatctctgga ccttcctgaa gccactgttt gcatagactt catttacttt tatccgggat  29107

tgtcattgtt ttttcagatt cataggccct atctgaaatt cacaaatcac ctagcaatac  29167

ttctctaaga aatcttcaga atccatgaca atttagacca gacaatgctg gattatgcac  29227

ttcagttcac tttttgttac tacaaggtat ttttcagtgc ccccaacagc tatcttaact  29287
```

```
cattctcatt ttaccaaagt ccatgtagac acggcactat tcctcaatga gacaactaac  29347

tagaccacct tgttgtcagt cagagtacct tcctctacct acttttatct tccttatatc  29407

ctctttgagt tagtataagt tattactctg catgacctgc tctaatctcc ttcaggggaa  29467

ggcttttaca aatctactac ctagagttaa accccagatc accttcctga gtaggagatt  29527

gcatttggtt ctattcattt taccttattt ggcttctacc ttcacttttt aagacttact  29587

ttgcctttaa cagtttttc catacagttc atctaaagtc caaatatatt tattagatgt  29647

gtgcattgtg tgtatatact tagatatgcc actgttggag atttcgggcc agtgatgcca  29707

ctctgataat attttaatat ttgacatatt atttttgctt actcattatt cttagataat  29767

atcatgttat gataccttgc ctttattttt atttatgctt caactatgtg gagaggaagc  29827

actgaaaaat tcacttaatt gaatgttgta ttgatcaatt gttcaatatt gtattccatt  29887

cctttgcgca tgctttgaat gcaggtgcta tataatttca gagaaaaata cctcattttg  29947

actgtacaaa aaccccatgt agggagcaga gctcacattg ttttcccctt ttagagacaa  30007

gaaaactaag atacagagaa tttaagtcac ttgcccagct gttaagtgac tgattaaaat  30067

ttgaaccctg gtcatcttat tcccgtctgg ttgtttttct agtctaccag tctattaaga  30127

ttagctaggt gtttttaat tgttttaatg aagtaattac tatgcttggt aatgtaaatg  30187

aaagttttat agattcataa ataagaattt gaattggcat actttattat catgcttggc  30247

aatgaaaata ggaaaatgct taaatgtcca ttttatttaa agacagactg tttttacta  30307

tgattttact gtttttctcc acatttctaa tatataatat aaatttgcta g gct ata  30364
                                                         Ala Ile
                                                         685

gaa tca aag aat gca gaa gga atc ttt gat gcg agt ctg cat ttg aaa  30412
Glu Ser Lys Asn Ala Glu Gly Ile Phe Asp Ala Ser Leu His Leu Lys
            690                 695                 700

gcc caa gtt gat cag ctt acc gga aga aat gaa gaa tta aga cag gag  30460
Ala Gln Val Asp Gln Leu Thr Gly Arg Asn Glu Glu Leu Arg Gln Glu
        705                 710                 715

ctc agg gaa tct cgg aaa gag gct ata aat tat tca cag cag ttg gca  30508
Leu Arg Glu Ser Arg Lys Glu Ala Ile Asn Tyr Ser Gln Gln Leu Ala
    720                 725                 730

aaa gct aat tta aag gtgagaattt tattaaataa aagaaaatgc taaacataag  30563
Lys Ala Asn Leu Lys
735

aatgtagatt taataggaaa tttttaattt tttaaaaaga atgctttatg agaaaatgcc  30623

ccttgaatta attctttcaa tattaagaaa ctggatttct cttataaaat tataagtgga  30683

aaataagtgc cttataagat tgaaaagaat acaaaaattc taaatctcat acctaggcat  30743

ttctaagcag aaactgaagt atggttgagg taaaattcct ggcagggcat tcacatatct  30803

gtcaatttgt ctttctttgg gtgtaagagt tgtgattctc attgctggat ttttttttcc  30863

ag ata gac cat ctt gaa aaa gaa act agt ctt tta cga caa tca gaa  30910
   Ile Asp His Leu Glu Lys Glu Thr Ser Leu Leu Arg Gln Ser Glu
   740                 745                 750

gga tca aat gtt gtt ttt aaa gga att gac tta cct gat ggg ata gca  30958
Gly Ser Asn Val Val Phe Lys Gly Ile Asp Leu Pro Asp Gly Ile Ala
755                 760                 765                 770

cca tct agt gcc agt atc att aat tct cag aat gaa tat tta ata cat  31006
Pro Ser Ser Ala Ser Ile Ile Asn Ser Gln Asn Glu Tyr Leu Ile His
                775                 780                 785

ttg tta cag gtattgaaaa ttttgttaca ggtattgaaa attttacatg  31055
Leu Leu Gln
```

```
tgaataacaa aaatcattgg tagtatgttt ctttatgttt ttatttttat tttactttat  31115

tttaattttt ccatcaccaa agcatgcaga tagtactttt ctcaatattt agtcttcatg  31175

tattcctgag ttctcaaaat agtaacagtg aaatatattt tttatggatt ttgatgttag  31235

atggattata aataaaagca atttatacca ttcattccat tcatctgcat gagcagcatg  31295

ttcatacatc ttgttcgcac acctgtcatt catgtgaaat atatggttca caagcagaac  31355

aacaagcagc tattataaag cagtgttaag taaatgagca cttttatttc ttgctgggtg  31415

gaaaacaaaa gaataaagtc tgtcaaggct ttttagtgtc atgatagaat tgttcccctt  31475

tttgcattca caagtaaaaa ctactttttt tttgagacag agcctcactc tgtcactcag  31535

gctggagtgc agttgcgcta tcttggctca ctgcaacttc cacctcctga gtttaagtga  31595

ttctcatgcc tcagcctcct gagtagctgg gactacaggc atgcatccct ggctaatttt  31655

tgtatttttt tttagtagag atggtgtgtc gtcatattgg ccaggctggt ctcaaactcc  31715

tggtctcaag tgattcgcct gccttggcct cccaaggtgc tagggttaca gacgtgagcc  31775

actgcacaca gccataagca aaaacttcta aaccaaatta ttcttcatct ttgtcttccc  31835

tttacgcaat aaaatgttaa tctaccacca aagaggaaag ggtactctac tatactacct  31895

gccctgggtt tctcagtttt gctgtctata taatggtcgt tatgaatgtc ctaatgacag  31955

atccttttca ttattttatt tgaaatttga ctatctataa catcacatac attataaata  32015

taattacaaa tatatgttca gaatcaatga aaatatattt ttgattatat gggccactat  32075

ttctctctgc taggtgatcc atttgtgagt atacttgagt tataattatt aagtactcat  32135

ttttattttg gaaattacag taattcatct ttttctcaat attgggattt ttattattat  32195

tttatgttgt ctaaggacag ccttaactac ttattagaat attgctttgt atgtgatatt  32255

attattttta aatgtataat tttaacatta ttatttctct tatttacctg aggtatagga  32315

acactatcag caaatattgg tagtatggca ttgtcgtatt ttttgagata aaattcatga  32375

tttttaatct ttgtataaga aatatatcag aagtttgtag tagattagag agtaccaact  32435

gggagtctga aaagctgtcc aaagtggcaa aacaggtact tagactctca atcctaaggc  32495

tgtatagagc tataaacgtg gcaagacctt tggagtcaga cagacccaaa ctcaaatgtt  32555

ggatccatgt atatggaaag cacctgacaa caagcctagc atatgtactt ggtaaaaatg  32615

attgccaagt gtagtgttaa tgagtttttg gatattgagt aagttattta aatttcaatt  32675

tcatctttaa aatgaaataa ttggaaagga taatttgagt gagggtatga aattatgtgt  32735

tcataagaga gggtatgtgg ccgagtgact agaggcgagt ttataactat tctatctaat  32795

aaaactttgt aatctggtaa tttgtgtgct aaaaataact ttacctgttg tatagtactc  32855

tttttttatg ccttaaacta aagtgttcaa aatatcatgg aaaaatgatc tgtgttgctt  32915

acagatttgg tgacttttaa ctttcctata atgttgtcag aatatgaatt tatactttca  32975

aattcagcat ttattctatt gtgttttttt ttgcattctt atttctaaac cacttttcag  33035

gaa cta gaa aat aaa gaa aaa aag tta aag aat tta gaa gat tct ctt    33083
Glu Leu Glu Asn Lys Glu Lys Lys Leu Lys Asn Leu Glu Asp Ser Leu
790                 795                 800                 805

gaa gat tac aac aga aaa ttt gct gta att cgt cat caa caa agt ttg    33131
Glu Asp Tyr Asn Arg Lys Phe Ala Val Ile Arg His Gln Gln Ser Leu
                810                 815                 820

ttg tat aaa gaa tac cta ag  gtataggtat tagcaaaact ataaatataa      33181
Leu Tyr Lys Glu Tyr Leu Ser
            825

ttgcagtata ttcttgttaa ttgtgaaagt aacgtaagaa taatttatgt tttgttcttc  33241
```

```
ccttcttctt cttcctttgc aattgtattt ttttttactc tggtaactac tgttaggaac  33301

ttatttatgg agacagtgta gcttaatgat tacattaagc ctgggattat cctgcctggg  33361

tttgagtcat ttaacgtttg ctttttgtaa gagcttgagc aagtcatctt acctatctgt  33421

gtctcagttt ccttatctgt aagttacttt gtaagtaata cccttttcat aggattattg  33481

taaaacgtaa atgaattatt agatgaaaat gctcggacta gtgtgtggca catatgaaca  33541

gtttgtaaat gttagctgtt gttagcatca ttcatcatca tcacaatcat cattgttcat  33601

atatgtttat agggaactaa catatttctc cttatttctg tcatctcatc taaatcaata  33661

gaatgatttc cttaatagga attagaatac ctaatcaaag gtgatttaaa cactaagaat  33721

aattattatc tgacctaacc agaaccacaa agctagttgt agggcaggtc atatttgaag  33781

gttgttgtta tcgcctatga tggttgtaaa atagctgcat gaattcaaga aagatgatgt  33841

gcccattgaa gaagaggagc atttttttct acatagcttt tatttttaaa taaacatttt  33901

tttctggtga tacctggcag acattgactc cgatctcatt tgctagaatt ggatcacatg  33961

tccaagtctg aaccattcag ttgcaaagag aatgataccg ctatactggg tttatgccaa  34021

gaacattaca catgtttgtg gaatgctcat gtgtagacaa cagtgtctta cacaacttca  34081

aaaaaataat ttatatataa atatgtttta aattactttt taaattcaca agaatttatg  34141

gtatacaaca tggtgttcta tatatgtata tactatgcta tacaacatgg tgttctatat  34201

atgtatatac tatgctatac aacatggtgt tctatatatg tatatactgt ggaatggcta  34261

aatcaagcta cttaacatat gtattacctc gcatactttt tttttttttt ccttgagaca  34321

gagtcttgct ctgtcaccca ggctggagtg cagtggcgct atcttggctc actgcaacct  34381

ctgcctcctg ggtccaagtt attttcttgc ctcagcctcc caagtagctg agattacagg  34441

catgtgccac cacgcctggc taatttttgt atttttggta aagacggagt tttgccatat  34501

tgtccacgct agtctcaaaa ttcctagcct caagcaatct gcccaccttg gcctcccaaa  34561

gtgctgggat tacagcatac ttcttcttat tttttttttt ttttgcacta agaacactta  34621

aaatttactc tcttagcaat tttaaagtat ataatatact gttattaact ttggtcacta  34681

ttttaattag acttaagatg tgtttgtatt caaattattt tgtaagcatt taacacccaa  34741

atttgagagt ggggtcagaa tgttggaatt tgatttctag aattagtata gggtattatt  34801

ttcctacttt ttttctgtgt tcaataaaat gtttataaga ttcagcttca attatattat  34861

aacccattta gtggtgaatc agggaagaat gaaaataatt tgataacttt gttgccttgc  34921

atttatttaa aaaattttta attctaggct aaaccctttt taaatgaaag tttaacttct  34981

tgtgttttca gatactgaat agctatgata cctcttgtgt tgagaaaact ttaaatttgc  35041

ataatctgaa gttatctttt cttataaaca ttttattagg tttacagtat tgtctttttg  35101

ttttgttttg tttttag t gaa aag gag acc tgg aaa aca gaa tct aaa aca   35152
                     Glu Lys Glu Thr Trp Lys Thr Glu Ser Lys Thr
                         830                 835

ata aaa gag gaa aag aga aaa ctt gag gat caa gtc caa caa gat gct    35200
Ile Lys Glu Glu Lys Arg Lys Leu Glu Asp Gln Val Gln Gln Asp Ala
840                 845                 850                 855

ata aaa gta aaa gaa tat aat gtaagtaaaa catttttaac attagtatgc       35251
Ile Lys Val Lys Glu Tyr Asn
                860

aatattgtac aaagtaggat agctagattc aacaagtaat atggatgtgt ctttgtgcag  35311

aat ttg ctc aat gct ctt cag atg gat tcg gat gaa atg aaa aaa ata    35359
Asn Leu Leu Asn Ala Leu Gln Met Asp Ser Asp Glu Met Lys Lys Ile
```

```
        865                 870                 875

ctt gca gaa aat agt agg aaa att act gtt ttg caa gtg aat gaa aaa    35407
Leu Ala Glu Asn Ser Arg Lys Ile Thr Val Leu Gln Val Asn Glu Lys
    880                 885                 890

tca ctt ata agg caa tat aca acc tta gta gaa ttg gag cga caa ctt    35455
Ser Leu Ile Arg Gln Tyr Thr Thr Leu Val Glu Leu Glu Arg Gln Leu
895                 900                 905                 910

aga aaa gaa aat gag aag caa aag aat gaa ttg ttg tca atg gag gct    35503
Arg Lys Glu Asn Glu Lys Gln Lys Asn Glu Leu Leu Ser Met Glu Ala
                915                 920                 925

gaa gtt tgt gaa aaa att ggg tgt ttg caa aga ttt aag gtacatctga     35552
Glu Val Cys Glu Lys Ile Gly Cys Leu Gln Arg Phe Lys
            930                 935

ttcttatttt gctttttctg actatgaaaa atttcaaata tgcagaagat aggatggtat  35612

caataatgct catcacctga attaatagtt aacatttatt aacattttgt cataattgct  35672

tcttctgatt tttgtgggat gtttgaattg cagacattcc tcccctaaat atttaatgta  35732

ccctttttgaa aaaggctttt ttctttaact aaccatagta actttattat acctaacaaa  35792

atgacagtaa ttttctaata tcgcctaata ccctgattat agtcacattt tttacatttt  35852

ttgatcaaag aataagcatt tggatgttac atctcataaa tctttttaat atagaatccc  35912

cttggttttc tttttctcca aaaaatgttt gaagatgtat ctaacttttg tgtgtgtgtc  35972

attttacttg ttcctgtgtc ccttgtatta ctaaaagtta ggtcagaacc ctaagttaca  36032

ttcaggttta aacatttttg gcaagaatac ttcataagta gtgttctata ctttatattg  36092

catcacttca agagtatctg gttgttccat gttttgtaat tgattactct gttaaggaaa  36152

agacaagcag accaagtatg gtggctcatg cctataattc caacattttg gaaggcccag  36212

gcaggaaaat ttcctgagcc cagaccagcc taggcaatat agtgagactc cgtctctaca  36272

aaaaatgttt ttttttttgt ttgtttgttt ttaattagct tggtgtagtg gcacatgctt  36332

gtaatcccag ctacctggga cattgaggtg ggaggatcgc ttgagcccag gaagttgggg  36392

gctgcagtga gctgtgatca tgtgccactg atctccagcc tatgtgcctg tataacagag  36452

cgagtctctc tcttaaaaga aaaaaagaag aagaagaaga agaaaagata accatatacc  36512

tccattatta agcaatttag ctaactggtg atattttggt accatacaaa taacaaatta  36572

tttgtcagtc ctaatgattt tagcatctgc tgatgattgt tgcctaaccc aattattaaa  36632

agttgcaaac atcataattt tctagttata ttatgcactt acatttatta acagacatgc  36692

ttttgtaaaa taaatagcgt ttcctcatta gcccaggcta tttgtttatc ttgaagttta  36752

gctcctacta caaaggcaag ataaatgctt ttctctttaa ttaccagttt tcagaataca  36812

cacttggtgt actctgcact acctgctttt tttgtcccct ccgctttctc ttttttaagt  36872

atcagattag actcacagat ttttaaatat tccatgtgtt ttagttggag tcatattctt  36932

ttgtctcaac tttagccaaa gagagtcctt taaagttgac tcttatattg tcttgacaaa  36992

aattcattag tcttttgaac gaagcctcaa agcttgactt gttttctagc ataagatgtc  37052

ttagacttac ctacatactt catgcccata cttggaataa accatttctt taaagagccc  37112

aggttccttt tagtggggaa ggcatttaga taccaaaaac tggccactgg gcatcattgc  37172

tctcagagta tcattgccac tagtctctca gtagacaagt tagaaaaata tgtatatatt  37232

taaaccatga gttcatattg ttatttccag tttaattata acattatggg gtaagtaaat  37292

agtatcggat ttttactaag cttctttgat tttgcacttg tattttttttc ttacatagaa  37352

aacctttatt attaacatta aaatatttgt tttatcctac aatatacata caataatttg  37412
```

```
aaaaataata cttgaattga tattaatagt aacaacaaca gcactgctgc caaacatagt  37472

ttaaagtttt atttcaggtc ttattttctt cagaatatat cttgctgaga atgtataggc  37532

aaagtattct acacttactt gaaataattg tcttcatgcg gttatgttat acatttgata  37592

tatagttagg ctcatttgtt tttcattttt tttattttag ggattttttt cctttattga  37652

attttaatat atacaatatt tatatatgca aaatatttaa tcagagaaat cttaattctg  37712

gtcttacgcc tttcatatta ttctgctcca ccctctgtag gtaacttatt atctttctca  37772

tgtttccttt ttggaaacat aaacaaagac aagacaggtt acatgacatg tataccettc  37832

tgcacctagt tttatacctt accttgtagt ttatttttaa gcatgtaaat gttcaatgtt  37892

catgactaaa tttggacagg atcataggaa cacagaattc aaagtgaaat taaaatgggc  37952

ttgggttctt tactttccac tttaaaggtt gtaatgggtg atgtcaggct aataaaccta  38012

ttttcagctt gatctaaagc ttaatactga gcatcaagaa attctttaat aaatataagt  38072

gatatttatt cagacatgta ataaggaaat gttcatgtct tatttttgtg ttagattttt  38132

ttagaatcta cttttgttag agttttataa atacagttag tgtttgagat agaaagagaa  38192

aagaattagt tttcttcctc ttctacctgc tcatgaactt gatttttttc tcccaacaat  38252

tgaagagcca agaaaaaggg agattcttaa gagatgggaa atagaatctc atctacccct  38312

gtttccccca gaacagtgaa actgaatctt aagggtaaga tagaatagtg tgtacttaac  38372

ttagatggag aagaaaggct gccaaaatga gatctgaagc gctattacaa atatttccat  38432

cgttactgta cttcagaatg aattacaacc gtaagttttt ttacttcctc attcataaat  38492

ttgattattc cttataccac ttctcagctt tcatcattct ttattgtact tttctatgta  38552

atgtttgcct attatacagc aacttaagag aactgtaagt ttggacattt cattttggtg  38612

ttgataatag aatatctttg aatagttcta tagttgatga gtagaaccat gaaccaagta  38672

acttaaagtc cttgatgtta tttattacag agaactataa tagaagctct cccgctaatg  38732

tttccatcat gtgtacaaaa agttttcttg ttattaaagc tagtccgttt aacttacaat  38792

aagcataaat agctaagctg tgaaagttac ctgtgataat gctaattttc ccatttatta  38852

aaaggcaagt tgttttccga tcataagaaa tttagaaaag ccatccaaag ataaattccg  38912

agtgatatat tcctgctgtt tgttatgttt tctcaaatta attgagtttt attttacaat  38972

gacaggagtt attaaagtat tttattttta ttatgattaa gattttcaaa gtaacatttc  39032

ttatatgaaa gaaattatgt taatgcatgt ttttcttaca tgggaaatca tatattttaa  39092

aaatgatttt aaaattcgtt ttactttaag ttgtattatc tttctcaaaa gtggctagtg  39152

cttgaccaga aaaaaagaca ccagcataac tcagtgtatc tttatttaca tag gaa     39208
                                                            Glu
                                                            940

atg gcc att ttc aag att gca gct ctc caa aaa gtt gta gat aat agt    39256
Met Ala Ile Phe Lys Ile Ala Ala Leu Gln Lys Val Val Asp Asn Ser
                945                 950                 955

gtt tct ttg tct gaa cta gaa ctg gct aat aaa cag tac aat gaa ctg    39304
Val Ser Leu Ser Glu Leu Glu Leu Ala Asn Lys Gln Tyr Asn Glu Leu
            960                 965                 970

act gct aag tac agg gac atc ttg caa aaa gat aat atg ctt gtt caa    39352
Thr Ala Lys Tyr Arg Asp Ile Leu Gln Lys Asp Asn Met Leu Val Gln
        975                 980                 985

aga aca agt aac ttg gaa cac ctg gag gtaagtttgt gtgattcttg          39399
Arg Thr Ser Asn Leu Glu His Leu Glu
    990                 995
```

```
aaccttgtga aattagccat ttttcttcaa tatttttgtg tttgggggga tttggcagat  39459
tttaattaaa gtttgcctgc atttatataa atttaacaga gatataatta tccatattat  39519
tcattcagtt tagttataaa tattttgttc ccacataaca cacacacaca cacacaatat  39579
attatctatt tatagtggct gaatgacttc tgaatgatta tctagatcat tctccttagg  39639
tcacttgcat gatttagctg aatcaaacct cttttaacca gacatctaag agaaaaagga  39699
gcatgaaaca ggtagaatat tgtaatcaaa ggagggaagc actcattaag tgcccatccc  39759
tttctcttac ccctgtaccc agaacaaact attctcccat ggtccctggc ttttgttcct  39819
tggaatggat gtagccaaca gtagctgaaa tattaagggc tcttcctgga ccatggatgc  39879
actctgtaaa ttctcatcat tttttattgt agaataaatg tagaatttta atgtagaata  39939
aatttattta atgtagaata aaaaataaaa aaactagagt agaatatcat aagttacaat  39999
ctgtgaatat ggaccagacc ctttgtagtt atcttacagc cacttgaact ctataccttt  40059
tactgaggac agaacaagct cctgatttgt tcatcttcct catcagaaat agaggcttat  40119
ggattttgga ttattcttat ctaagatcct ttcacaggag tagaataaga tctaattcta  40179
ttagctcaaa agcttttgct ggctcataga gacacattca gtaaatgaaa acgttgttct  40239
gagtagcttt caggattcct actaaattat gagtcatgtt tatcaatatt atttagaagt  40299
aatcataatc agtttgcttt ctgctgcttt tgccaaagag aggtgattat gttacttttt  40359
atagaaaatt atgcctattt agtgtggtga taatttattt ttttccattc tccatgtcct  40419
ctgtcctatc ctctccagca ttagaaagtc ctaggcaaga gacatcttgt ggataatgta  40479
tcaatgagtg atgtttaacg ttatcatttt cccaaagagt atttttcatc tttcctaaag  40539
attttttttt tttttttttg agatggagtt tcattctgtc acccaggctg agtgcagtgg  40599
cacgatctcg gcttaacgct tactgcatcc tctgcctccc agattcaagc agttctcctg  40659
cctcagcctc tgagtagctg ggattacagg tgtgcaccac cacaccagct aatttttttt  40719
tttttttttt tttttttgag gcagagtctc gctctgtcac ccaggctgga gtgcagtggc  40779
gccatcttgg ctcactgcaa gctccacctc ccgggttcag gccgttctcc tgcctcagcc  40839
tcctgagtag ctggtaccac aggcacccac catcatgccc ggctaatttt ttgtattttt  40899
agtagagatg gggtttcacc ttgttagcca ggatggtgtc gatctcctga actcgtgatc  40959
cacccgcctc ggcctcctaa agtgctggga ttacagatgt gagccaccgc acctggcccc  41019
agttgtaatt gtgaatatct catacctatc cctattggca gtgtcttagt tttatttttt  41079
attatcttta ttgtggcagc cattattcct gtctctatct ccagtcttac atcctcctta  41139
ctgccacaag aatgatcatt ctaaacatga atcctaccct gtgactccca tgtgactccc  41199
cgccttaaaa actgtcaaaa gctaccggtt acctgaaggg taaaagtcaa gtcccctact  41259
tacctcatgt catctagagc aagagatgaa ctagctgagt tttctgacca cagtgttctt  41319
tcttatgtat gttcttttgt acgtgctctt ttctatatat agggaaccat ttctctcttc  41379
cagttgtttt gctcagtgaa tttctattcc tgtttcaaaa cttgttcagg cattaccttt  41439
tttttcttaa gcatactttt tttaatggaa caaagtcact cctgtctaca ctagttctgc  41499
atcttataca taggttttgt acatagtaca tatttatatc acatcaaatt atatgtgttt  41559
acatatctgt cttccttaat ggaatataag tcttttgata taaggaacta tttaatttgt  41619
ttctgtgtgt tgagtatctc ctgtttggca cagagttcaa gctaatacat gagagtgatt  41679
agtggtggag agccacagtg catgtggtgt caaatatggt gcttaggaaa ttattgttgc  41739
tttttgagag gtaaaggttc atgagactag aggtcacgaa aatcagattt catgtgtgaa  41799
```

```
gaatggaata gataataagg aaatacaaaa actggatggg taataaagca aaagaaaaac  41859
ttgaaatttg atagtagaag aaaaaagaaa tagatgtaga ttgaggtaga atcaagaaga  41919
ggattctttt tttgttgttt tttttttga aacagagtct cactgtgttg cccaggctgg  41979
agtgcagtgg agtgatcttg gcttactgca acctctgcct cccaggttca agcgattctt  42039
ctgcttcagt ctcccgagta gctggaatta caggtgccca ccagcacggc cggctaattt  42099
agtagagaca gggttttgcc atgttggccg ggctggtctc aaactttgga tctcaggtaa  42159
tccgccagcc tcaacttccc aaagtgctgg gattacaggc atgagccact gtgcccagcc  42219
tgttttttt tttttaaagg agaccagtga agtttcagga ggagggaaag aaaatttaga  42279
gttactaggg agagagtgat gaagataaga gatgaaagtg gtaataaggg aaatagcaaa  42339
atatcagggt aggtgggaga aaaagagatt tgtaacaaac aataggatta tcctgtgaaa  42399
aaggatgaaa ggaagaaaaa aatggataga aagatattta aaacaccctc agcctcctgt  42459
tttccctcct gtgtattcat agtatataaa actataatta tgtactttac ttaaaaaata  42519
tattattatt accttatcgt gcttatttaa tcatagcatg tcctcttttt agtctcatta  42579
ccctgtttgt attattcttc ataacactta atacctgaca ttgtattata tattggctta  42639
ttttccaggt actccactca aatataagtt ctaggatata atttatttat cactgaaatc  42699
cattgcttag agtacctggc atgtagtaaa taggcattct gtttttcaa ataaaaaata  42759
aaggaactta agatatatat ttatgttata tcgccagcct ttttcctcac agctctattc  42819
tgttgtacag aattacctac tttacaattc ctgtgtttca aggggatctc aaatttaacg  42879
tgtccacaat gaactcctga tttctgtttc tctcctagtc attcttattt caatatatgt  42939
tcagttacct aaccagctag tcaaggcaga tactttagag ttattctgta gtcattcttt  42999
ttccctacca tttttgtttt ccaaatgtaa tttatgtgtg tcttcttcat cctcgcagct  43059
ctaacccttg tccaaaccag catcatcact catctggagt tccacaatgt ctttctggct  43119
agtttccctg atttctctat tgaccccttt attctccaca gtgcagccag aatgattgtt  43179
taaaacttcc tccttaaaat ctttaaattg ttttctttta tacgttaagt taaattccag  43239
ttccttgtct tggcatgcca tgccctgcct ggtgtggccc ctgatggtct ctccaacttc  43299
atgttttact actattgact cttatttttg cttactctgc ttgggtgctc cagtcctcca  43359
aatcatttcc tgctccaatc atttcaatca ttttttcctc tcagatctta tagtattcca  43419
aatgctttct tcctttggag catctgggtt tactaataaa tacttcgtac ctcacagttc  43479
agcttaaata tcaattattt ggtggttaag acatccttca accgctctat ctaaatgttc  43539
ctttctatta ttcactggct cagtactctg tttttatttt ctttctaaat gtcaactttt  43599
tttttttga gtcagggtct cactgttgcc caggctcgag tgcagttgca caatcatagc  43659
tcattgcagc cttgccctcc tgggatcaag taattctccc acctcagcct ccaaaatagc  43719
tgggattaca ggtatgcatc accatgctca gctaattttt tgtgtttttt tgtagagatg  43779
aggtctcact ttgttgccca ggctggtctc aaactcctgg actcaagtga ttctcccacc  43839
tcagcctccc aaagtgctgg ggttacaggt gtgagccact gcacctggtc gatactgact  43899
ttttttttt tttgagatgg agttttgctc tgttgcccag gctagagcgc agtggtgtga  43959
tctcagctca ctgcaacctc cacctcccag gttaaaggga ttcttctgcc tcagtctcct  44019
gagtagctgg gattacaggc aagtgccatc atgactggct aatttttgta tttttagcac  44079
tatgtttagt actgtgttgg ccaggcttgt ctcgaactcc tgacctcaag tgatccaccc  44139
```

```
acctcagcct cccaaagtgc tgggattaca ggtgtgagcc accgtaatcg gccaacattg  44199

acatttttag tagacttttt gtttgtttac ttgcttatta tctgctgcct tccacactct  44259

ggcgaaatcc tgccacccac ccacacacac ataggcactg aatgggcaga actctgaagg  44319

ccagaatttt atatttcttt tcactgtaaa catcatcatc tgtcactgat ggcacactag  44379

gatgctcagc aactgtgtgc atgaaggaag taagcactag tttgtgaagg ctgcaaaact  44439

cttgagtatt ctaagagttt tggccaaaat gaatgtacag ctttagtggc agaagctaat  44499

actcagaaat tgaggccgta tattggataa cacaggattt ggatgattat tttaaaataa  44559

tattttacat tgtatatatg tgtgtgtgtg tgtgtgtgtg tgtgtgtatg tgtgtgtgtg  44619

tgtatatata tatgtatgta tgtgtattag tccgttctca tgctgctatg aagaaatacc  44679

tgagactggg taatttataa aggaaagagg tttaattgac tcacagttcc acagagctgg  44739

ggaggcctca gaaaacttaa cagttatggc agaaggggaa gcaaacacat ttttcttcac  44799

atggtggccg gaattagaag aatgtgagcc gagcaaaggg gaaagcccct tataaaacca  44859

tcagacatcg tgagaactta ctattatgag aatagcgtgg gggaaaccac ccccacgatt  44919

caattacctc ccaccaaatc cctcccatga catatgagga ttatgggaac tatgattcaa  44979

gatgagattt gggtagggac acagccaaac catatcagta tgtatatgta tacaagtatt  45039

atatatatat gtatgtgttt gtatgcatac atgtattata tatggaggaa attctaattt  45099

tgtaaaaaac tggattgtga gttttaagga gatgttatat aaagttaaga caatgtcatt  45159

ttgtggtatt ggtctgaatt acaatgtagt ttcttagtga tatttttcct ttattcag    45217

tgt gaa aac  atc tcc tta aaa gaa  caa gtg gag tct ata  aat aaa     45262
Cys Glu Asn  Ile Ser Leu Lys Glu  Gln Val Glu Ser Ile  Asn Lys
        1000                 1005                 1010

gaa ctg gag  att acc aag gaa aaa  ctt cac act att gaa  caa gcc     45307
Glu Leu Glu  Ile Thr Lys Glu Lys  Leu His Thr Ile Glu  Gln Ala
        1015                 1020                 1025

tgg gaa cag  gaa act aaa tta g gtaagtttta tgactctgat aatataaaat    45359
Trp Glu Gln  Glu Thr Lys Leu
        1030

gattaacatc taataatgaa tatttcttat ttaaagttcc ttttttatgc tagattaaaa  45419

ggaagtattt tgactaaaaa aagaaagaac tttctgccta ataatttaac ttaggcagat  45479

gaataatcct gtacttaacc ccaccaaagt ttagttttca gtccttaagt tagatttgtt  45539

tctaatgaaa tcatatatgt taaaaattta tgactaagta ttagctactt tgaaccgttt  45599

aacaattaaa actgatgata ttttattaat ggtattatga gttctttcac tgagtgcaag  45659

ttatattagt tatatatcac ttgatatttt taaattaaaa gataccagga aacagcaaag  45719

aaaatgtgaa aagaagttgt atttctcata gttttactac tatattactg tatatttttg  45779

ctcctatatg cttacatatt ttatatattt taaattatta taaacatggt tttatactgt  45839

atttagatag taatatcaaa aatattttta tggccggcgc agtggctcac acctgtaatt  45899

ccagcacttg ggaggctgag gagagcagat cccctggggt caggagttcg agaccagcct  45959

ggccaacatg gcaaaacccc atctctacta aaagtacaaa aattagccag gcgtggtggc  46019

agttgcctgt aattccatct actcaggagg ctgaggcagg agaattgctt gaacctagga  46079

gtcagaggtt gcagtgagcc aagatcatac cacagcactc cagcctaggc gataagagtg  46139

agactccgtc tcaaaaaaaa aaaaaaattt gttttattca tcatacttat aaatacttat  46199

acaatagcct aatgtgtttg agtgattaaa tcactagctt tttatatttt tgctattgct  46259

tatagtgcca cagtgaacat tttcatgtat atctaacaga gatattactg tctcagaagg  46319
```

```
tattgaaatc tttgttgctc tcattagagt tttccatatt aatttttcaa acagttatat  46379

agtttataag attttcataa ttttatctca tatattgtgc ttcataattt tcaaataaat  46439

ttgctgcttt cgataatgta ttttcatgta tttgtttcct agacgttaga gctattcaag  46499

gtttttatta ctaaatagag ctgttctctt aaattggtaa tgagatactt ggtttagaga  46559

agcctaacac tgggaaatct tacataagct acttttagaa atgtaatttt tagctcaata  46619

agagattaaa tatgaattga cttttgtgta gtatttgcat ggaagaaggt accatttaaa  46679

tgaagacatg agagtattac gtacaatttt agtaggttct ttttatttta tcatctttat  46739

ttttaataaa tgctgaattc cctacagaaa ttctttaatt tttacatatc ttgatctctt  46799

tcatatatgg atttatatca ccgaagtttt aagagtgttt ccctattccc tgttgccctt  46859

atatctttgt ttaaaaatgt cacatcatta gcttttttttc atctaggaat ttgttagtgt  46919

tgggctgttg tgctctaccc tctctttaag aaaactccaa acccaaaaac atacaagatg  46979

gctagtctgc ttcagccttt gtgatgtgct tttctcttct aatcagagtt tagcacaata  47039

cagaatggag aaggactcct ttatatattg gtatttattg cagtattttt ctacatggtg  47099

cctaaggtta cttgaatgag tctttattcc ataatgaact gatttactaa tgcttttagc  47159

acctgttagt gatccattat tgttagttac ttgattactg cttgccacag ctattctaaa  47219

ataatacatt ttaaagataa atacagaaca taatgaagta ctttttaaaa ctgagataga  47279

gaccaatttt tttttcagga aatgtatatt actttgagaa aactcagtta taaaacttga  47339

acttatgaag ctggaaaaac aggagggggc attattggta ttgtaaaagg ctgtttacaa  47399

agtgagttgc tgcttagttc ctttaagtaa ttggctaccc taaacacatc agttttaagt  47459

tgctgaaaag caaaacactc taccaaattt tgtttttttt ctagaccatg tttacaaagc  47519

aaaagtatgt tttcttcccc ccccctcaaa aaatgactaa tgacactcct atgcgatgcc  47579

tttttatggt aaattgaggc ttttagttct ctttccattt agccacagac ttttgtgtcc  47639

aaagacaagc tgcgtaactg catatataag gttaaggcat aactactaat aaaagaatgt  47699

aaaatatttg atattaggtc tgtacaaaga ccaaataata ctcatgatta gacaagatta  47759

tatttggtag aatctatcca tcatatggct tcagatttta cttttcagct tggctttgtg  47819

agactttaaa aatcaagtca ttgcacttat attcacaaag tcacattgct ttactgcatt  47879

gcttctcata cagtttatct cctttcagta aaatgtttac ttgccatttt taaaatttct  47939

tatatgtgac acttctacac taagtccttt atgttgttag ttccacaatt ctgtgaggaa  47999

taggtttttt tttttaatca tttgattgat gaagaacatt aagttccaca gagattaaat  48059

ggtacaggca tcacacaggc aggaagtaac agagctaaga ttagagtcca ggtctgatgg  48119

aattcagaaa gctaatgtgc tttccatgga actataatgc tttctaatat acagcatcta  48179

aaatatctga ggtaatttta atataaacag catgagattg acttaaatat tattgcatgt  48239

ag gt   aat gaa tct agc atg  gat aag gca aag aaa  tca ata acc aac  48285
   Gly  Asn Glu Ser Ser Met  Asp Lys Ala Lys Lys  Ser Ile Thr Asn
   1035                 1040                 1045

agt  gac att gtt tcc att  tca aaa aaa ata act  atg ctg gaa atg     48330
Ser  Asp Ile Val Ser Ile  Ser Lys Lys Ile Thr  Met Leu Glu Met
1050                 1055                 1060

aag  gaa tta aat gaa agg  cag cgg gct gaa cat  tgt caa aaa atg     48375
Lys  Glu Leu Asn Glu Arg  Gln Arg Ala Glu His  Cys Gln Lys Met
1065                 1070                 1075

tat  gaa cac tta cgg act  tcg tta aag caa atg  gag gaa cgt aat     48420
Tyr  Glu His Leu Arg Thr  Ser Leu Lys Gln Met  Glu Glu Arg Asn
```

```
1080                1085                1090

ttt  gaa ttg gaa acc aaa  ttt gct gag gtttgatatt ataagtttta       48467
Phe  Glu Leu Glu Thr Lys  Phe Ala Glu
1095                1100

tcatacaatt atagaataaa gaattagttt tggtagacat tgtattattg ttaagtggtt  48527

tgtctggatc tctgaaatat cttattaata tagtgcctat gttttgtgta ataaataaat  48587

aaaagattta aatctgaatt gtttaaaagg aaagcagata tttctgtaag tttttctcac  48647

caatgttata ttattagatt taatttatga aatgttattt actaaacaat ggaattgcct  48707

ttcaccacca tcccttcatt taacaaatat ttattcattg cctattacat gtcagaccct  48767

gtgttgggac tggcagtata gcaagaaaca aaatagacaa taatctctac tttcagggac  48827

tttacattct aattggtggt tttatatatt tttgatgtgg tcagaatcat taaactgtgt  48887

ggcagtaaat atagtttgca agtatttaac aatttatgat taaacacaac tcttacagtg  48947

tttgcttacc ttgagattta atatattttc aaagcattta tatcattttt gttttaacta  49007

tgtcactaaa tctatatgag taagatttta ttaactcatt tggatttatt tatagatgat  49067

acaattgaag taaaatataa tgagcagatt gcattctaag caaagtaaga atattgcaag  49127

ttcagatatt attagataat gagttgccta ataaaaatga cttttggtgg attggaatat  49187

aaccagagtt tccatagttt gtttctgatt ctttcatatt ttttaccctc cttcagtctg  49247

ttcttaacac ttcacactta atataatatg tgaactaagg ccaagtaaag aggattgcag  49307

tactttaaaa gctaaattac aaagaaaacc tcaccaaaaa ttgatgtatc tgaacatttt  49367

ttgttacatt tccttag ctt acc  aaa atc aat ttg gat  gca cag aag gtg   49417
                   Leu Thr  Lys Ile Asn Leu Asp  Ala Gln Lys Val
                       1105                1110

gaa  cag atg tta aga gat  gaa tta gct gat agt  gtg agc aag gca     49462
Glu  Gln Met Leu Arg Asp  Glu Leu Ala Asp Ser  Val Ser Lys Ala
1115                1120                1125

gta  agt gat gct gat agg  caa cgg att cta gaa  tta gag aag aat     49507
Val  Ser Asp Ala Asp Arg  Gln Arg Ile Leu Glu  Leu Glu Lys Asn
1130                1135                1140

gaa  atg gaa cta aaa gtt  gaa gtg tca aa  gtaagtgcat ataagcattt    49556
Glu  Met Glu Leu Lys Val  Glu Val Ser Lys
1145                1150

tagccatttg actagatgta tcttctttaa tttgtcttta agaaacccaa ttacaggtat  49616

acaattctta gtagtaattg atactgattt ctttttataa gaacaggatt aagtaatatt  49676

aagatcggtt ttaacagggt taaataataa tattgacgag aataatattg ttaaagagga  49736

agtgacctct caagatttgc attttttaga gttcaggaat attattgcag aaaggtccag  49796

ttcctccaca tattgatttt ttggggaagg ggtgatggag gaggaatggt tgtttattgt  49856

atttaaactt aagtttcttc attttaataa gggagtaata gtacctcttc tacctgtttc  49916

ataaggttgc tgtaagaata taataaaaaa ttcagatttt gatttagttt acatttatcg  49976

ggcatctact atgtactagt cacggtgcaa ggtattaaac atatattgac ttgtacaatt  50036

atacttaacc ttgaggttat atttttgttt tcattttaca tgaagaaata tgcccagcta  50096

gtttagaaca caaaatatat ataaggagta aatactgcgt gctggctggg cgtggtgaca  50156

tgtgcctgta gccccagcta ctcgggaggc agaggcagga gaatcgcttg atcccgggag  50216

gtggaggttg cagtgagccg agatcgcgcc actgcactcc tgcctggtga cagagcgaga  50276

ctctgtcaaa caaacaaaca aacaaagaaa aacaaaacaa aaaaaccgtg tgccagctat  50336

atgctgtatt ttcattctct tttgtaatta ggtgatattt cagtagaaaa gtataaggag  50396
```

```
cacttagtta atctgtcaag cataaatagt aaaaatattt tatggcctac tcataaaaat  50456

ataaccattc ctttggagcc ttgatagttc tcttgggaat atcagttttt gacatctttt  50516

tcactatgaa agaccctttt ttttaaaaaa attgatcctt tcttctcatg gacctctttt  50576

gatataaact aacttataat agttcatttt aatcatattt tgttaatcat gcaactggca  50636

atgagagcct ctcatcagta tgaggaaacc tgccttatct ataatactga actaaaatta  50696

ttctaaccca aagcaaagaa actttacatt ttgctttgcc tgtattagct tatcacagta  50756

ttcatgaggg aatttgaagg acttattacc attaggctat ctcttttttt ttttttttgt  50816

aattttatta aatgcatgtt ttgtttcttt tcacattact gataacttgt agattaaaac  50876

aaatcaaaac atgcattaat ccatctaagg atcctagaaa ttttacattt ctgtgttctt  50936

aactgtgtga tggtcttaga taaatgtact aaatacctta tcctagcata ttccaaatta  50996

tgacaataaa tgttttatgg aaaaaagtat gggaacagaa gttctttggc tatatacatt  51056

tggaaaatac tatatagtaa gtatgatttg agataattat atatgataga acctctggga  51116

gcactgaata tatgttagga atattcaaga gggaggaggg atgttgagaa tgaagttttt  51176

tttatatagc aaacatgata acctctgatg gaattatgtt tcatgaaaca gtttaggaaa  51236

tcctgtttta atatttcata caaagaagag atagatgctg aaaacgaatg gctttttgaa  51296

aaagggtcta gaaattttga attttggcat ttacttagaa agtgtactta attgttcctg  51356

aaatacctta tcatttccta g a ctg  aga gag att tct gat  att gcc aga    51405
                          Leu  Arg Glu Ile Ser Asp  Ile Ala Arg
                          1155                 1160

aga caa  gtt gaa att ttg aat  gca caa caa caa tct  agg gac aag     51450
Arg Gln  Val Glu Ile Leu Asn  Ala Gln Gln Gln Ser  Arg Asp Lys
    1165                 1170                 1175

gaa gta  gag tcc ctc aga atg  caa ctg cta gac tat  cag gtatgtgcag  51499
Glu Val  Glu Ser Leu Arg Met  Gln Leu Leu Asp Tyr  Gln
    1180                 1185                 1190

tattggctct tctacataga atccactttt ttccctaaat ttacattaga tgttgggagt  51559

gggatatgtt atactttttg tttgtttcga gatagggtct cattctgttg cccagggtgg  51619

agtgcagtgg tacattcaag gctcattgca gccttcacca cctgggttca ggtgatcctc  51679

ccacctcagc ctcttagaca gctgggacta caggcacgtg ccaccacacc taattttttt  51739

gcattttttg tagagacagg gtttcaccat gttgcctagg ctggtcccaa actcctgggt  51799

taaaatgatc tgcccacctt gacttcccag aatgctggga ttacaggtat gagccaccat  51859

gctgggccat tgttacattt ttaatcaaaa gatataccaa ccagaggctg ttattcttgt  51919

tagttggaac ctgattagaa agctctttaa tttgaaatat tgttcagtaa tccagtacag  51979

catttaaatg cctatagatg aattatgctg ctgatcaaaa ttaggacact gagaattgta  52039

gttagtaaat ctttaataac aatattttct cttgtattta tatgtaactt tttacatatt  52099

cttacgttat atatgttggg aattataaaa acatacacat tgtcctgatc agtattatgt  52159

tacttgcaat ggaggttaaa aaaaaactgt aacagtcagg catggtggct cacgcctgta  52219

atcccagcac tctgggaggc cgaggcaggc ggatcacgag gtcaggagtt cgagaccagc  52279

ctgaccaata tggtgaaacc ccgtccctac taaaaataca aaagttagcc aggcgtggtg  52339

gcatgtgcct gtaatcccag ctacccagga ggctgaggca ggagaattgc ttgaacccgg  52399

gaggtggagg ttgcagtgag ccaaaatcac gccattgcac tccagcttgg gtgacagagt  52459

gaaactctgt ctcaaaaaaa aaaaaaaaaa acaccagtaa catacccact gttattcagt  52519
```

```
tacatttgga ttttaagttt gtttgattct aggtttttc ttttacagtt ctttggtaat  52579

tatttgtatt aaagcaaagt tacatttttg tagatctcat gtgccactgt gttaaaactt  52639

tgcttagtaa attgtgaatt ttaaatctgt gataactttc actggaaaaa tttgaaactt  52699

actacaaata tatattttt ttaatatcag gca cag tct gat  gaa aag tcg ctc  52753
                                 Ala Gln Ser Asp  Glu Lys Ser Leu
                                             1195

att  gcc aag ttg cac caa  cat aat gtc tct ctt  caa ctg agt gag     52798
Ile  Ala Lys Leu His Gln  His Asn Val Ser Leu  Gln Leu Ser Glu
1200                 1205                 1210

gct  act gct ctt ggt aag  ttg gag tca att aca  tct aaa ctg cag     52843
Ala  Thr Ala Leu Gly Lys  Leu Glu Ser Ile Thr  Ser Lys Leu Gln
1215                 1220                 1225

aag  atg gag gcc tac aac  ttg cgc tta gag cag  aaa ctt gat gaa     52888
Lys  Met Glu Ala Tyr Asn  Leu Arg Leu Glu Gln  Lys Leu Asp Glu
1230                 1235                 1240

aaa  gaa cag gct ctc tat  tat gct cgt ttg gag  gga aga aac aga     52933
Lys  Glu Gln Ala Leu Tyr  Tyr Ala Arg Leu Glu  Gly Arg Asn Arg
1245                 1250                 1255

gca  aaa cat ctg cgc caa  aca att cag tct cta  cga cga cag ttt     52978
Ala  Lys His Leu Arg Gln  Thr Ile Gln Ser Leu  Arg Arg Gln Phe
1260                 1265                 1270

agt  gga gct tta ccc ttg  gca caa cag gaa aag  ttc tcc aaa aca     53023
Ser  Gly Ala Leu Pro Leu  Ala Gln Gln Glu Lys  Phe Ser Lys Thr
1275                 1280                 1285

atg  att caa cta caa aat  gac aaa ctt aag ata  atg caa gaa atg     53068
Met  Ile Gln Leu Gln Asn  Asp Lys Leu Lys Ile  Met Gln Glu Met
1290                 1295                 1300

aaa  aat tct caa caa gaa  cat aga aat atg gag  aac aaa aca ttg     53113
Lys  Asn Ser Gln Gln Glu  His Arg Asn Met Glu  Asn Lys Thr Leu
1305                 1310                 1315

gag  atg gaa tta aaa tta  aag ggc ctg gaa gag  tta ata agc act     53158
Glu  Met Glu Leu Lys Leu  Lys Gly Leu Glu Glu  Leu Ile Ser Thr
1320                 1325                 1330

tta  aag gat acc aaa gga  gcc caa aag gtaaacattt aaacttgatt        53205
Leu  Lys Asp Thr Lys Gly  Ala Gln Lys
1335                 1340

ttttttttta agagacagta tcttgatctg tttcccaggc tggagttcag tggtgcaaac  53265

atagctggaa ctcctgggct caagggactc tctagcctca gcctcctgag tagttgtagc  53325

tggcagtaca ggtgcacacc accataccta cctaattttt taaaattttt aaattttttt  53385

gtagagacaa ggtctcactt tgtcacccag gctggccttg aactcctggc ttcaagtaat  53445

cctcctgctt tggtctctca aaagtgctga gattacaggc atgagccact gtgcccagcc  53505

aattttaaat tcattatctt caaaagagtt acatgataat ttcttaatat atgcctatat  53565

gaaaaatgct taagatacaa attccaatta tgattcatta atttagattt tataacttag  53625

cagtgttggc tatttgaatg tctattatac gtaaaaataa aattaggctt ttctaaccaa  53685

agattttagt gggaatgttc agattgtata atagcaaaga attttaatta ctataggaaa  53745

atttatatta attaaacact aattattata tttaaacatt gtagtagtta tcagttgatt  53805

tctactgttc ataattatct ttgatctaca agtagtgggc ccacatttac ttttaatatg  53865

gtttaatctt catttagaaa gaattaaatg aaaaataatt atcttgcaac tacatcctgt  53925

tctctaggct agaaacattt aggatttctg tttttgaaag taataccaaa gttccaatga  53985

cctgcttata gtcagtgttc aataaacgta taacaaatga aagtgaatat tagtgatgtc  54045

cattccaaca taatttgaag atttttattg taaaatccca catatttgta gaaaagtcta  54105
```

```
tggaaatcct aaataagatt ttgtcatgta gtttgacaaa agataacatt gtgtcttatt  54165

ttattttaga atggccatta ctttcaatta aaatcattat catcaatgga ggaatgttat  54225

ttgttaatat agcatttata tttgtgtata taaattgtaa atcttag gta atc  aac    54281
                                                    Val Ile  Asn
                                                        1345

tgg cat atg aaa  ata gaa gaa ctt cgt  ctt caa gaa ctt aaa  cta     54326
Trp His Met Lys  Ile Glu Glu Leu Arg  Leu Gln Glu Leu Lys  Leu
            1350                 1355                 1360

aat cgg gaa tta  gtc aag gat aaa gaa  gaa ata aaa tat ttg  aat     54371
Asn Arg Glu Leu  Val Lys Asp Lys Glu  Glu Ile Lys Tyr Leu  Asn
            1365                 1370                 1375

aac ata att tct  gaa tat gaa cgt aca  atc agc agt ctt gaa  gaa     54416
Asn Ile Ile Ser  Glu Tyr Glu Arg Thr  Ile Ser Ser Leu Glu  Glu
            1380                 1385                 1390

gaa att gtg caa  cag aac aag gttttatttt atatttattt catttttttc      54467
Glu Ile Val Gln  Gln Asn Lys
            1395

cctaagtttt tttttttttt tttttttttt gagatggagt ctcactctgt cgcccagact  54527

ggagtgcagt ggcgtgatct cggctcactg caagctctgc ctcccgggtt catgccattc  54587

tcctgcctca gcctcccaag tagctgggac tacaggcacc cgccaccgtg cctggctaat  54647

tttttgtatt tttagtagag acggggtttc accatattag ccaggatggt cttgatctcc  54707

tgacctcatg atccgcccgc ctcggcctcc caaagtgctg ggattacagg cgtgagcccc  54767

taagatttta aacaagaata ttgcacaaat gactatgtta tccttctaat taagtgcacc  54827

ttccattact aattgattat ataataattt gtttttttatt ttctaaacta ttctaaaaat  54887

tcatatttat ttagctttta taacagtagt cttaatctta aaaacggcaa tacataagca  54947

acctcatttg gtaagttaat ttttattttg atattggtta tttgactttt cacagttcca  55007

cgtttctact ggctctcact gatagagtaa gaagtcagct tcttatagaa taaagtatat  55067

acttcagaga cagatgaaat tcgtcaaaca tatgactgtc tcagagattg ttccccctgc  55127

ttaaattgtt cttaccctag ataccttttgg tatttacact gtcagtgcct gcaggtctta  55187

gctcaaatgt cttaccttat cagtgtatcc ttcaccagcc acctaatata caacagtaaa  55247

tcctactatc cagattccta aatagagatt aattaactta atttttctcc aaagtgcttg  55307

taaccttctg acgtattaca tacttactgg tttattattg actgtctttc cttcgccaga  55367

atgcaagttc cgtggtgaca cggacttggt tttgtttact gccatgtttg tatttcctag  55427

aatgatgctt ggcacataat atatgtcatc aaatatcttt cgtatagctg aacggatgga  55487

tggatggatg gatggatgga tggatagact gaaatcctta cttcacatct gcctttgtga  55547

tcttacacaa gttacttcac ctctctgagt ttgtattttt ttccataaaa ggaaaataat  55607

tacagtttct tcaatgtgtt gtgaggatta gataagaaaa tatatataaa atgcctgtta  55667

tgtgcctgat gtcttcgtgt atgtgtctga cacaaattgt ccttttttta g ttt cat   55724
                                                         Phe His
                                                             1400

gaa gaa aga caa atg  gcc tgg gat caa aga  gaa gtt gac ctg gaa      55769
Glu Glu Arg Gln Met  Ala Trp Asp Gln Arg  Glu Val Asp Leu Glu
                1405                 1410                 1415

cgc caa cta gac att  ttt gac cgt cag caa  aat gaa ata cta aat      55814
Arg Gln Leu Asp Ile  Phe Asp Arg Gln Gln  Asn Glu Ile Leu Asn
                1420                 1425                 1430

gcg gca caa aag gtatgaatga ttaatcttgt ttgttactct gtagcatagt        55866
Ala Ala Gln Lys
```

```
ctagagtgtt aactcacaga aatatttcct gtatcagatg taattttaat tgatgttata  55926

ttgtatattt aaaatataag aggggtttaa tctatgtttt atcatacagc tgtaaaaatt  55986

aatagttact ctcaatgctg caactgcttt tttaaaaaac atactatttc ttaatag     56043

ttt  gaa gaa gct aca gga  tca atc cct gac cct  agt ttg ccc ctt     56088
Phe  Glu Glu Ala Thr Gly  Ser Ile Pro Asp Pro  Ser Leu Pro Leu
1435                1440                 1445

cca  aat caa ctt gag atc  gct cta agg aaa att  aag gag aac att     56133
Pro  Asn Gln Leu Glu Ile  Ala Leu Arg Lys Ile  Lys Glu Asn Ile
1450                1455                 1460

cga  ata att cta gaa aca  cgg gca act tgc aaa  tca cta gaa gag     56178
Arg  Ile Ile Leu Glu Thr  Arg Ala Thr Cys Lys  Ser Leu Glu Glu
1465                1470                 1475

gtaattagaa gaatttgcat tttgattagt gtattatttg gtatgtttgg ggggctttct  56238

aaataatatt tctttatgag ggcaatgcat agaatgatga atctattgct aatttcacta  56298

tttttctatt ctcctataat gtttctaata gccaataatg aacagcagat atagttaatt  56358

tgaattcact atttaattat tagttggtac ctttcggtac actgaatatg aaaggaaata  56418

aaaagcattt aattgtagtt ctatgagcaa tatattctct tatatgatct ctttattctt  56478

actttttggg ttttattttg aagtgcatgt tacataatct atgaatcaat tttcagttca  56538

ttgcctttaa tgcatggtta aagggttgaa ggtaaattag aaattacttt ctgttttaac  56598

ctagatcttg aatttgatta gtaggtgatc aaatctgtca tcttcattaa attattcaga  56658

aaataatgta aactgaatgt gttttcattt tagttttcat ctaaataaac tgcaaataca  56718

tttaaaatat acataaagaa gtttttcaag taaaactgta catttttaat catttcagga  56778

aacgtagatt ttcttcagta attttaagat ttgtcattta tgtgaattgc cattgaatta  56838

cttaatttaa aatactcacc ttaatcctct tgaagagtaa aaatttttct gttttttctt  56898

ctttgtttta ataagctgcg gattttatat tcgtaattta ttgagttggg cctctaaaat  56958

tccagttttg tacttaactg acttatagat tagtctccta atgctctgct agtcaatgga  57018

ccaaaataaa agaaataatt tattacatat tcttcctaaa tctagtacca ccatacatgt  57078

ataattctaa actgtaatat ctcaataaag taccttaatt aaattttatg ttcatcataa  57138

caatgaagtt tctagcatat gtaatagtct tataaataag catgcaaata actgctgtca  57198

attagaatta gtcagtttaa ccttattaag tatcaaatgg ctattgtaca tatgatgtga  57258

aaaataaagt gaattttttt tggctaataa ctaatctaaa attcagatga agcattttaa  57318

agggaaaaag atactttaat gatttattat aatttaatca ttgcag aaa  cta aaa    57373
                                                   Lys  Leu Lys
                                                   1480

gag aaa gaa  tct gct tta agg tta  gca gaa caa aat ata  ctg tca     57418
Glu Lys Glu  Ser Ala Leu Arg Leu  Ala Glu Gln Asn Ile  Leu Ser
        1485                 1490                 1495

aga gac aaa  gta atc aat gaa ctg  agg ctt cga ttg cct  gcc act     57463
Arg Asp Lys  Val Ile Asn Glu Leu  Arg Leu Arg Leu Pro  Ala Thr
        1500                 1505                 1510

gca gaa aga  gaa aag ctc ata gct  gag cta ggc aga aaa  gag atg     57508
Ala Glu Arg  Glu Lys Leu Ile Ala  Glu Leu Gly Arg Lys  Glu Met
        1515                 1520                 1525

gaa cca aaa  tct cac cac aca ttg  aaa att gct cat caa  acc att     57553
Glu Pro Lys  Ser His His Thr Leu  Lys Ile Ala His Gln  Thr Ile
        1530                 1535                 1540

gca aac atg  caa gca agg tta aat  caa aaa gaa gaa gta  tta aag     57598
Ala Asn Met  Gln Ala Arg Leu Asn  Gln Lys Glu Glu Val  Leu Lys
```

```
        1545                1550                1555

aag tat caa  cgt ctt cta gaa aaa  gcc aga gag gtattttatt          57641
Lys Tyr Gln  Arg Leu Leu Glu Lys  Ala Arg Glu
        1560                1565

atattatgag ttatgctgtt atccattagt ttttttaagc aaatgctaaa tattatttta  57701

ccctaaagtg gtatttcttt tcttgctttc aaatgattct atttaagaat tgttacttgc  57761

atgtgattgg attacacctc tgtcagtaaa actggaagtt tgtgtacatg tatctttcta  57821

ttatacactg actaaaccac gagtagctat catggtgaaa tcatatgatt ttgaaaaata  57881

ttttaattga gtttataggt gaggattgag gcaatagggt ggaatgaaat atatcacacc  57941

ggtaatcagt agaaatcaga tttgttagaa cttcgtgggg gaaagctaac atttaatttt  58001

ttctagaagt aagttaaaag atgatagata catgtcattc taatgttaag aataaattat  58061

gaactgaggc tgggcttgtc aacttgaaca ttgtctgagg ggacatgcat accagtctag  58121

atacatacat atatggagat actgtttctt cctcatctca aaggaatttt agaagattga  58181

agagaaaata tataaggtct tcaaaatgtg aatttgtttt aatcacaatt taagatatag  58241

tttcgatttt ctgtaaaaca g gag caa  aga gaa att gtg aag  aaa cat gag  58292
                        Glu Gln  Arg Glu Ile Val Lys  Lys His Glu
                            1570                1575

gaa gac  ctt cat att ctt cat  cac aga tta gaa cta  cag gct gat     58337
Glu Asp  Leu His Ile Leu His  His Arg Leu Glu Leu  Gln Ala Asp
    1580                1585                1590

agt tca  cta aat aaa ttc aaa  caa acg gct tgg gtaagattct          58380
Ser Ser  Leu Asn Lys Phe Lys  Gln Thr Ala Trp
    1595                1600

aagaactttg ttccattctt tattgatttt tgtgaccatg taaattaaaa ttcagctctc  58440

ttcttttttg gaatggaagt taccctttt gttgccaaaa taatcttctg aaaacatagc  58500

tctgatcatt cttcctcctg tagctcaccg ctgttcacaa aattatattt ataattctta  58560

gccatgtact caatctgcta tgaacctacc tgcctttctt ttcaaattct actcactgtg  58620

agtttagcta tatctaactt ccagaattca gctcatattt gcctcttttg accattctgt  58680

tccatatgta tgaaatgaca tgtctttcat cttttaatgt gtaaccttag catatttgag  58740

cattacctcg ttaattcggt caacacttat tgatctcctg ctacgtgcag acattttgct  58800

agctattgta aatacaaata ataaagtctg catttcctgt cttctttaag ccttcattgc  58860

ctattaaatc attacatttt agattagata ttatattttg atcatttgag gaaccaaatt  58920

aaaaatatgg aataagtatg gcattgaatt atacatgcct attgctaata tattcatatt  58980

ttatag gat  tta atg aaa cag tct  ccc act cca gtt cct  acc aac aag  59028
       Asp  Leu Met Lys Gln Ser  Pro Thr Pro Val Pro  Thr Asn Lys
       1605                1610                1615

cat ttt  att cgt ctg gct gag  atg gaa cag aca gta  gca gaa caa     59073
His Phe  Ile Arg Leu Ala Glu  Met Glu Gln Thr Val  Ala Glu Gln
    1620                1625                1630

gat gac  tct ctt tcc tca ctc  ttg gtc aaa cta aag  aaa gta tca     59118
Asp Asp  Ser Leu Ser Ser Leu  Leu Val Lys Leu Lys  Lys Val Ser
    1635                1640                1645

caa gat  ttg gag aga caa aga  gaa atc act gaa tta  aaa gta aaa     59163
Gln Asp  Leu Glu Arg Gln Arg  Glu Ile Thr Glu Leu  Lys Val Lys
    1650                1655                1660

gaa ttt  gaa aat atc aaa tta  ca  gtaagtcttc gaaatgtatt           59206
Glu Phe  Glu Asn Ile Lys Leu  Gln
    1665                1670

gtaaaaatag gcaaatgata agtgatataa tgaagataaa cataagtgtt tgctatgcca  59266
```

```
ggcactgttc taagactttt aagtatattg tctcattttt atcctcagga ctgctggtta  59326
catatgttat cattttcccc attttaaaga gaggatatgg cctcaggaat gcttaatagc  59386
atgtctgggg gtagatggga aagccataat ttgaaactag tcagtctgac tcaaaagcca  59446
atacaaattc ttttccagaa tctcattttt accttctttg agcctcagtt tcatcttatt  59506
tatttatttt tatttttgag acaaggtctg gctctatttc ctaggctgga gtgcagtgac  59566
ataatctcag ctcactgcaa ccttgacctt ccaggctcaa accatcttcc cacctcagcc  59626
tgcagagtag ctggcactac aggcaggtgc caccacacct gggtagtttt tttgtatttt  59686
tgtagagaca aggtttctcc atgttgccca ggctggtctt gaactcgtga gctcaagtga  59746
tccgcccact tcggcctccc aaagtgctgg gattacaggc ctgagccatt gcacccagcc  59806
tcatcatctt taaaatggaa ataataatac ttaccctggc cctttcaggg tggttatatg  59866
aaggtcaaat tataccgtgt atgaaagtaa tttgaaaact gtaaaataac atacagatag  59926
aaaacttttg attacacact tataagagtg tctgtcatat aatagagatt ctaaacattg  59986
ttcaaccact ttatcagaac gtagatttta aactcaaaat aggtttatag ttaggtagtt  60046
tctaatcatt ataatattat ctctatgggc ctaaatttta ttatctgaaa aaacatgaga  60106
aaattgaact gcttgactta taattccatt tcagctctca agcccctgct agagtctttg  60166
attctttact cacttattca aatgcctctg acagaattaa cactattttt gctttgctaa  60226
ggagctgcca ctgttaagaa attactctct aaaagaaaga aaattggcaa cagcatatgt  60286
gtattttcag tctcttttcc tcactctatt aaattttgta caagagatgt tatttttggt  60346
ctagtaaatt tctgtcatgt tttggagtat aaaattactt gtgcttttgc atctaatttg  60406
tgggtgtaga aaatcataat cttttgaaat accttatata atacattttt ttgccacagg  60466
aaatacttga agttattgtt gtgtacctta cgtcatttta gtccaaaatt atacttgtgt  60526
tctctgtgtg catattttga tatgtattag gagattatgg atctgtgtga tttcttaagt  60586
aaatcctgat attttcacaa tttgatgatg actctttaaa gttagactta agttttgcca  60646
aaagcaagaa gcctcaaaga gtaacatttg ttcatgtctt aacactatct ccctcttatt  60706
ggtcagaatc tcagtatgga tgcagtgtcc atatgcacaa caatatatta attcagttta  60766
acagacttaa tgctgaataa gcaataagat taattgaatt aactaaatct tttgatagta  60826
tccacttcca tatatatagt tatagatata atgctagtga atttgaacca taaacaaatt  60886
aataatacat gtgatttctg tgaaaattta tattagtctt ttcaatatgt caatataggg  60946
cagtatttct caaatataga ggatcagttt ttcaccattg tccctcttgg ggacatttgg  61006
cgatgtctgg agacattttt gattgtcatg gctcgggggt gctactggta tccagtgggt  61066
agaatcaaaa gatgctgcta aacatcctat catgcacaag gcagccccac caccaacaaa  61126
gaattatcca gtcaaaaatg ttactagtag tatggttagg aaactatcat atagaggaag  61186
caatcacatt ttacaagagc cataatattt aaaatgcctt tttgttcatt ctctgtatat  61246
ttgactagag tcacaaaata acttgataag attgttgcca aaaatattag aaactagaag  61306
aaaaatgtgt tgttaagtct aagagtagtt aaatgaaata aagaattatt cttctttgga  61366
tttggatgcc tgcatcaaga tttagattgt aaggatactt aggactgaac atttgctcta  61426
tatgaaattt gtattaatca aggtatgaat tgcagcaacc actctattaa ttacatatgt  61486
ttggccaggt gtggtggctc acacctgtaa tcccagcaat ttgggatgcc aaagcgggct  61546
tatcacctga ggtcatgcgt tcaaactggc ctggccaaca tggtgaaacc ccatctctac  61606
```

```
taaaaataca aaaattagct gggcctgatg gtgcacgccc gtagtcccag ctactcagga  61666

agttgaggca aaaaaatcac ttgaatctgg gaggcagagg ttgcagtcag ccgagattgc  61726

gctgctgcac tccagcctgg gtgacagagt gagactgggt ctcaaaaaaa ttaaaaatta  61786

aaaaacacac acacacatat gtttatttac atcag g ctt caa gaa aac  cat gaa  61840
                                         Leu Gln Glu Asn  His Glu
                                                     1675

gat gaa gtg  aaa aaa gta aaa gcg  gaa gta gag gat tta  aag tat     61885
Asp Glu Val  Lys Lys Val Lys Ala  Glu Val Glu Asp Leu  Lys Tyr
        1680                 1685                 1690

ctt ctg gac  cag tca caa aag gag  tca cag tgt tta aaa  tct gaa     61930
Leu Leu Asp  Gln Ser Gln Lys Glu  Ser Gln Cys Leu Lys  Ser Glu
        1695                 1700                 1705

ctt cag gct  caa aaa gaa gca aat  tca aga gct cca aca  act aca     61975
Leu Gln Ala  Gln Lys Glu Ala Asn  Ser Arg Ala Pro Thr  Thr Thr
        1710                 1715                 1720

atg aga aat  cta gta gaa cgg cta  aag agc caa tta gcc  ttg aag     62020
Met Arg Asn  Leu Val Glu Arg Leu  Lys Ser Gln Leu Ala  Leu Lys
        1725                 1730                 1735

gag aaa caa  cag aaa gtaagtaaca acagaaaatt atcaacattt aggaaaaata   62075
Glu Lys Gln  Gln Lys
        1740

tgtggtagat tgcttttaga gaagatttgt aaatttataa aagatggtag tataaatctc  62135

cgtgttgtaa taaaaagtat gagctttatc ttatgctgtt aaacaaggta ttttagacaa  62195

tgctgttttt gtgggcagat atagtccaat ttatcttttt atgttttcgt caatctgatt  62255

tgtgaattat ctatatgaag ttaggaaaaa tcttaatgta cattacaaaa atataatata  62315

tattacattg tattttcttt ttttctactg gaattttatg ctactgaggc tatttttaac  62375

aaatgaacaa ttttgaacaa tttgagggat tgagggaagt atgataatga caaaaaggga  62435

tgaaaaaagg gggtcataga gatgtttttg tgagaaggag ttggtcagtg tattctgatt  62495

tattagggtt ttttttagtt tatctcagat ttgatctatt taaattgttt tagaagatgc  62555

tggtgttttt ctgtgctagc tatgaaattt atgggtaaac tttaagcctt tcctagtcct  62615

tttgttgtct acctaaattc aattaatttc atatggaagg atgtagtaag tgagtaatat  62675

aaatatctaa aattggatgt ttgaaaacaa aacatacctg ttttttgtaa tagcttgatt  62735

taatgctgag ttctcaaaat cattattaag attttgaact ttcacattca atgtggaaag  62795

aattgagtgt aattacaaaa gatttatttg aaaaagttga gttgttaatt tgtgaaatat  62855

gttccattaa actcataata ttttagaaaa atagtaggaa gtaataaagc ttgtttattt  62915

tttatatcat atattcatat aaaatgtcag ttttccttta aaaattacat tttttttttg  62975

gttaattttt ag gca ctt agt  cgg gca ctt tta gaa  ctc cgg gca gaa    63023
              Ala Leu Ser  Arg Ala Leu Leu Glu  Leu Arg Ala Glu
                      1745                 1750

atg  aca gca gct gct gaa  gaa cgt att att tct  gca act tct caa     63068
Met  Thr Ala Ala Ala Glu  Glu Arg Ile Ile Ser  Ala Thr Ser Gln
1755                 1760                 1765

aaa  gag gcc cat ctc aat  gtt caa caa atc gtt  gat cga cat act     63113
Lys  Glu Ala His Leu Asn  Val Gln Gln Ile Val  Asp Arg His Thr
1770                 1775                 1780

aga  gag cta aag gtgaacatca acacgtgtta atgtaacaaa atttctgata       63165
Arg  Glu Leu Lys
1785

attcctattg gaagagaatt cactatgata tatagtaatt ttgttgatga atagggaatt  63225

tataatgcac tgttggtggc tagacataga cacacacatg catttttcaa caataagtct  63285
```

```
ctttatgata ctcatttact gattatcatc ttggggatta ggaaaggata ggccattatg  63345

aactactgtt tctaatgaaa ttaaatttaa gaaatatttt acttaggatt ttttttaaga  63405

ctttattatt tttttagagc aattttaggt tcacagcaaa attgagagga aggtacagag  63465

atttcctgta tatctcctac cctgaaagtg gtacatttgt taaaattgat gaacctatat  63525

tgatacatca taatcaccca aagtccaagt ttacctctat tttagctctt ggtattttac  63585

actctgtgtg tttagacaaa tgtataatga tatgtatcca tcattatagt attatacagg  63645

gtattttcac tgccctaaaa atcttctgtg cctctcttct tcattccttc ctctgcacct  63705

caccaaaccc ctggcaacca gtgatctttt tactgtctcc atagtttcac cttttccaga  63765

atatgttata gatggaaaca tacagtgtgt ccccatcatt ctcaccatag gacagctagg  63825

aactcctttc tagtggcata catattgtct agtattgtaa gttacccttt tatatcttat  63885

ctttgtaaac taggttagaa attacttcaa gtcagagatt tgttctgtac tactcttatg  63945

cttcatagtg tttaaaacgt tgtcatatat attgttatat acttgtttgt ttaattaatt  64005

cagccaaaat gaaacgtgca tatttgataa aattttgttt gtgggtgttt gttgaagatg  64065

aattgcttta cactagtttt tttttttttt ctcaaagtcg actttttttcc tcaaggtaga  64125

cttgacatga atatggaaaa atatatgtag tttgtggtta ttttttttct cttgtgtact  64185

taaaaattca gactgaattt ttcttataat ggtatatttt ctgttttatg ttccttttat  64245

cattgatact tcttgaagag tcatgaataa tacctttctt tttctcttat tag aca     64301
                                                           Thr

caa  gtt gaa gat tta aat  gaa aat ctt tta aaa  ttg aaa gaa gca     64346
Gln  Val Glu Asp Leu Asn  Glu Asn Leu Leu Lys  Leu Lys Glu Ala
1790                 1795                 1800

ctt  aaa aca agt aaa aac  aga gaa aac tca cta  act gat aat ttg     64391
Leu  Lys Thr Ser Lys Asn  Arg Glu Asn Ser Leu  Thr Asp Asn Leu
1805                 1810                 1815

aat  gac tta aat aat gaa  ctg caa aag aaa caa  aaa gcc tat aat     64436
Asn  Asp Leu Asn Asn Glu  Leu Gln Lys Lys Gln  Lys Ala Tyr Asn
1820                 1825                 1830

aaa  ata ctt aga gag aaa  gag gaa att gat caa  gag aat gat gaa     64481
Lys  Ile Leu Arg Glu Lys  Glu Glu Ile Asp Gln  Glu Asn Asp Glu
1835                 1840                 1845

ctg  aaa agg caa att aaa  aga cta acc agt gga  tta cag gtaattttat  64530
Leu  Lys Arg Gln Ile Lys  Arg Leu Thr Ser Gly  Leu Gln
1850                 1855                 1860

atttaactct gataatgtct gatttacaat atagaggtag tagtttattt ctactttatc  64590

attttatcta tggtatttgt taaaactgac tttcaaatca ctttgattaa tgtaattaat  64650

ttcttttgtg acttctattg tgtttatagt tctagagtag catattagta tgttgtatta  64710

aaatgcagaa gcagctacca gattatctta tgtattaagt gtcatttaga aagtatggtc  64770

agtgatagct tcagaaagtt gctattatat aattgaaata tttactgtct attttgtttt  64830

acatttattt gtaaaaatat aaagttacat tttatttttt ag ggc aaa ccc  ctg    64884
                                                Gly Lys Pro  Leu
                                                             1865

aca gat aat aaa  caa agt cta att gaa  gaa ctc caa agg aaa  gtt     64929
Thr Asp Asn Lys  Gln Ser Leu Ile Glu  Glu Leu Gln Arg Lys  Val
            1870                 1875                 1880

aaa aaa cta gag  aac caa tta gag gga  aag gtg gag gaa gta  gac     64974
Lys Lys Leu Glu  Asn Gln Leu Glu Gly  Lys Val Glu Glu Val  Asp
            1885                 1890                 1895

cta aaa cct atg  aaa gaa aag gtatgtgaag aaacatactg acttatatgc      65025
```

```
Leu Lys Pro Met  Lys Glu Lys
            1900

ttaaggtagt gacagagtaa gttaaataca tagctgatta acagttaata tactgcctta  65085

atttgatgac ctggctgtat taattctgta ttaattttga ggactataag cagtattgaa  65145

taacgtagaa aagtctaagt ttctgttctg taggaattta gagtctactt gaggagatac  65205

ctataatgta actcttattt ggaaattact acatcaattt cattcatctt tctgacatta  65265

gagtacctct gaagttcctt cacaccttaa catattcaac tgtgtatcat ttctctccaa  65325

agtaatcatt tacacaggtt ggtgcttttg acttttggga cagaaagata gacattttaa  65385

gataccccac tttgacccaa ataggtcctt tttaatcctt caggagacta ggctgttatt  65445

tcagatagca aagttatttg gaatatcttc agtatttgca gtaataatca gtaaccaatc  65505

tgctcataga ttaattctgt gggagaaatt gcttaaaatt ttatagttca tagtaaactg  65565

ttttgtaata aaaattactg attgaaataa ccccaaaaaa aactaaaatt ggctaaaatg  65625

cgtgtaatta aatttgttat ggacaataaa ttggagataa cttgttggta acattcaaaa  65685

tatcgaaagt gaactgggaa atgttgatgt tagcagtaat atttgccatt gaagaaaatc  65745

agtatggagg agctatggtt aggaaaattt ttattataaa atttacccag aaaatattta  65805

atgtctataa aataatttca atcacatgaa aatggaaaag aaaattctgt ctttaaaggc  65865

attgaataga aaataggtaa tggaattcaa atttcttaat agagtatgct cccaaaatta  65925

ttttctatga aaattcatta atgtcagtgt aatttattga cactatttgc gtggagtcac  65985

aacatgcttg ctgtcagaag ctttgctggt gaaaactgta agatcaaagt gtccttaatc  66045

ttttggattt ccatctttct aactccctaa ttggggatag gcctgatctt atccctaaat  66105

ggggataggt tagaaactgg tatgtttgtt cctaactggt gtgtttctat accagtttct  66165

aacctgattc ctatcagaat gttttaagag ccttgtggct ttgcctggac tcttctatgc  66225

tacagtttat ttagtttatt tattcagttt attcctcctt aaagtgggaa taatactatc  66285

tgtattgcca gtttctcagg attattttac ataaaatgat atgatatgcg gaagtctttt  66345

gtaagccatc acatccatag cagtataaga tattactact aactagaaag agaaaacagg  66405

ggtctatgcc cagtattaaa attggcattc aggaatctag tgagaatatt ttttcaggtt  66465

cattgcttgg gcatttctaa tttatactca agaaatgctt tcatattgtt tggaaatttt  66525

agtacccttt tctctgtaaa cagaatttgt agtctaccta tgtaacaaaa cccacccctg  66585

tgccttgcat ttcattctcc ttagcattta ttactatctt aacatactag acatgtactt  66645

gtcttttgtt catctttttt ttttcttttt ttattagacc ataaactttg atggcaggaa  66705

ctttgcctat tttatttatt attgtattcc cagcacctag aacaatcgct ggcacatagt  66765

agatgctcag tatttgttga atgaatataa atttttaaat gttataataa tattattctg  66825

aaatctatgc atacgaagct tttggtacag aaaacatgaa aagagaacta ctgccttatc  66885

atccagtctt cttccctctt ctcattcagt ctagaacata acctgttttg gaaaaagttc  66945

tcaaaccata tgtttatctt gccctcaaac cataacaaca atcaatgcaa aagacttctg  67005

tgacccccag aatatgtggg gatttctcca catcagcaag caagcagttg gttttgtagc  67065

agacaccaac tgggtgtcgt ccaattcaat tcatcatcta cctggagata gtgtcagatc  67125

ccacagatat cttacttcga tcaaatcaca agtccaggcc tccgtgactt ccgaagttcc  67185

cacatcccca gcccccagct ttgggtttga ttaatttcct ggagtggctc acagaactca  67245

gggaaacatt tacttacatt taccagttta taataaaggt tattacaaag gatacaggtt  67305
```

```
aagagatgtg taagaagaga tatgggggaa ggggtgtgga ccttccatgc ctttctgggg  67365
tgccaccttc ctctagaaac ctccacatgt tcagttctcc agaacctctc tgaacccagt  67425
cctcttggtt tttagggaag cttcatgaca tcagtatttc ttctcctagg gtatggggca  67485
ggacccccctc gtattagggt tttaagaccc acagtcagaa aggcagggga agattacagt  67545
cctgccttag ggcaggtgaa aggaggatgg gagaaggtca gagagactct tttctgaggt  67605
gtgctcggaa ggcctaacac actcaatatt ataactaaag atgaggacaa gggctatgag  67665
agttataagc caggaaccat ggaaaaaagc ctatatgtaa taacaccaca atacccatgg  67725
taccattcac gtttgttgtt tttctgtttt tcaattgttc tttcagtctt ggttccctta  67785
atcttaattt agcaagtaat gccaggtggg ataaaattgc ccaaacccaa caaagtactg  67845
tgtgctgcag gattatttaa tgacatacct tatgtccccc actagtattt acatttctgg  67905
gagtacagaa aaattcttgt acatatttca gaaaaaatga aattaataac tatcaaccac  67965
ttagtgaagt ttttactttt tttttgaga tggagtttta ttcttgtcac ccaggctgga  68025
gtgcaatggc gcaatctcag ctcactgcaa cctccgcctc ctgggttcaa gtgattctcc  68085
tgcatcaacc tcccaagtag ctgggattac aggtgcctgg caccacgact ggctaatttt  68145
tgaattttta gtaaagatgg ggtttcacca tgttggccag gctagtctca aactcctgac  68205
ctcaggtgat ctgcccgcct tggcccccca aagtgctgga ttacaggtat gagccaccac  68265
acccagactg aagtttttac atttttttaaa gggcacttat tagctgaatt aaataaggta  68325
aaaaattgac tagtattaga gacaagaatt ggagaatata gttctctagt attcgagaaa  68385
gtcgttttga taggacaact aatcttagtg agaatttggc tttatttcat attttttttaa  68445
tttttgaga tgacgtctta ctatgttgcc ctggctggtc tttgaactct gggctcaaac  68505
aatcttcctg cctcggcctc ccaaagtgct gagattataa gcatgagcca tctccccagg  68565
aatttgactt taaaccatgg ttctcaaccc tttcagattc aacattccct ttaataaaaa  68625
atataatgtt tcataatttc ccctttacta ttataattga aatgcatagt taacataaac  68685
tctacctact tacataattt caaaaatgtc attatgaatg tcctaaatga aatatatagg  68745
gggaacataa aaggaatatt catatttcaa catgtaaatg ctttggcatg actccattgg  68805
aaaatataat gaactagtca tgtgcttgca ccttcattaa tgtgagttca aagctacgat  68865
tgcagactga cacaaatgtg ttctattggc aactgatggg tcatgatggt attgccattt  68925
gtaatttgat ttccaaaatg gtaaacaaat tgttggtgca gttctcagca aaacaatgtc  68985
tataatctta ccttttataa gactgttgta ttcctagaaa acttagtgta tagtaaaacc  69045
attaaaaaat tacttagtgt gaatatgtta gttggagata aattcttagc tcagaccagt  69105
gtaagcagaa ttttttactg tattaatatc cagtagaaca tttgaaagtt gttcagtgca  69165
tgagactatt ctgcattgga taggctttct ttggctcctt tatcatagtt ataataaacc  69225
atgacaccta cccctgaaat gccctaattc ccttccgttt ctttttcttt tttcttttta  69285
gcacttaaaa ctagctaact tactacaaaa tagatttaga tttatttctt gttttgttat  69345
ctgtatcgtt tgctcccttc tccccaatct atctaaccaa ctagtataaa ctagatagta  69405
agattcatga agatacactt ttttatctga ttttattcat ttgttctatt cctattgcct  69465
ctagagtagt acttggcaca tggttagcac taaataagta cctgtcaaat gagtgaagta  69525
atgtgcattg aagacttgaa ggggctctga tgctaggaaa ttgtcatggg ataatagatg  69585
aggttggtcg tttgtacaga ggattcttgt tagaagctta ctctagtcat gattgtatta  69645
gaatcttcat ttaaaggctc ctgaagggtg ttggcattag tcagaactgt ctcccagaat  69705
```

```
tttatttgtc ttgtgataga ataaagcata gttagcctaa agagcagttt tcctaatagc  69765

tcggcatgcc caaagattct aggagttata caggttgaac atctaatcca aaaatctgaa  69825

atgctccaag atacaaaatt ttttgagcac caatatgatg ccacaagtgg aaaattctga  69885

tgtgacctca tatgatgagt cacagtcaaa acacagtcaa aactttgttt catgtacaaa  69945

attattaaaa aatattgtat aatactacct ccaagctatg tgtagaaggt gtatgtgaaa  70005

cataagtgaa ttttgtgttt ggacttggga cccatcccta agatatctca ttatgtatat  70065

gcaaatattc caaaaatatt ttttaaaaaa atccaaattc taaaacacgg ctggttccaa  70125

gcgtttcgta agggatactc aacctgtata gcaaaatgaa catatttaca tattctctag  70185

gaaatattag tttacaattt ttctaggcaa attataattg ataaatcata aagaaaattt  70245

aaaataacac tggtaatttt cctacctcct tcgttattgt tacag aat gct  aaa     70299
                                                  Asn Ala  Lys
                                                      1905

gaa gaa tta att  agg tgg gaa gaa ggt  aaa aag tgg caa gcc  aaa     70344
Glu Glu Leu Ile  Arg Trp Glu Glu Gly  Lys Lys Trp Gln Ala  Lys
            1910                 1915                 1920

ata gaa gga att  cga aac aag tta aaa  gag aaa gag ggg gaa  gtc     70389
Ile Glu Gly Ile  Arg Asn Lys Leu Lys  Glu Lys Glu Gly Glu  Val
            1925                 1930                 1935

ttt act tta aca  aag cag ttg aat act  ttg aag gat ctt ttt  gcc     70434
Phe Thr Leu Thr  Lys Gln Leu Asn Thr  Leu Lys Asp Leu Phe  Ala
            1940                 1945                 1950

aa  gtgagtttaa atatcattat aaaactaatt atgtgtaaaa tcctttagtg         70486
Lys

acctggaaat tatatagctt tatcatagtt gataatatga gaaatggtct agtttaaatg  70546

atcatttatt atctatgatt tacttacttt ttattttctt taaaatctgt tttaaatata  70606

ttgtaacaat tatagatgga ttttcctgtg atctcgttgt aaattagctt atgacaaata  70666

tagggtgtta caattattgt aatttggttt ggtaatgagt atgcaattga aaagccaaac  70726

actgaatggt atatttcatg attctatatt aaattccaca g a gcc gat aaa  gag   70780
                                               Ala Asp Lys  Glu
                                                            1955

aaa ctt act ttg  cag agg aaa cta aaa  aca act ggc atg act  gtt     70825
Lys Leu Thr Leu  Gln Arg Lys Leu Lys  Thr Thr Gly Met Thr  Val
            1960                 1965                 1970

gat cag gtt ttg  gga ata cga gct ttg  gag tca gaa aaa gaa  ttg     70870
Asp Gln Val Leu  Gly Ile Arg Ala Leu  Glu Ser Glu Lys Glu  Leu
            1975                 1980                 1985

gaa gaa tta aaa  aag aga aat ctt gac  tta gaa aat gat ata  ttg     70915
Glu Glu Leu Lys  Lys Arg Asn Leu Asp  Leu Glu Asn Asp Ile  Leu
            1990                 1995                 2000

tat atg ag  gtaagctatt atgtggaaat gtgccaccca ttgtaatgaa            70963
Tyr Met Arg

aaactggttg accccctagaa attgaaataa taaatgtgtg ttgtcttaag cttgggttat  71023

gttttctttt cccatgtgaa ttgagatatt cctggttctt catatgccac ataattttgg  71083

tgtatttttg atcttttgaa tattatattg tgagactctg gttcttgttt aaattctatg  71143

ggaaaatgta gatacttttg ttttagcatg caatcggtct aattaggttc aggccacaag  71203

ttccaacctc atttcttggg ctgtggttcc atttttcaaa gccttttcaa tactcttcag  71263

atctgtcctg cctgtgtacc tcacaatagg tgatctggta tgtgagctat gtaccattag  71323

ttcagttctt agaaactttg gtattctgat taggatcgat ccatacattt gcagctcaag  71383
```

```
agtgagccca gaagttcata aacaacttta tagggtccct ttcttgagct cctccctctt  71443

tgccatctct ctgatacttt gtttccctag ggatttccat ttggggcttt agttacccag  71503

tgatgccatg tacttcagga attgcacact tctgcagcca agcaagcaag aggagagtag  71563

aaagaggaag aaaaaaacga cttttacctt accctcttag tatcatagct ctaccaattg  71623

gagatttccc tcccaaaaaa tattagcttc tgtgagttcc cattgcagcc tctattacca  71683

ctgctatggg atggcttaag ggttggggca tgaaagaaca gatagaagaa aaaaaaagtg  71743

aggtgttttc atattgtctc ttgagtgtta aaagattccc tttctcttta ctcgagctag  71803

aattagaagg tttacctgga gctctctctg tcagtgcaga cacccatctt caggtttcaa  71863

ataatgttgt cttcagggca ggcagtaaca gaataaaaga aaaggtaaat tcatcacctg  71923

tttgctgcta ctttaagtcc tggtattcta ttgtaatctg ccttctactc ctttgcaaag  71983

tcctcaaatg gttgctccat gcatttagga gagagaagat tgaatgtatt tactccattg  72043

tacctggaac cagatgccct tgccctgcat caccccatgt catttcttag cagagccttt  72103

gagatttttg tgtgtgtgtg ctttacaatc tctttccaag ttatatcttc tgatacagtc  72163

atggtcgtga aaagcaaaat aaaatcatgt gttaacattt aaaacttttt aattttattc  72223

tgacaacagc taaaactatt taatcttctg tttcgctcat ttcttccaag gtaaacttca  72283

gttggtttta cgtgatttgc tatttcttct tctttgcatt tacaaatgat ctgtgatcat  72343

attactgatc tttgtaaagg gctaatatct acctgcaaca tttggatatg acagtattta  72403

ccctttgtaa atacacattt tctatttatc ttcaaaaatt accattcatt agtctgtgtt  72463

aatgtctgtt tactattgtg tcattatgaa tgtgatgtga acatacgaag ttgaacttat  72523

ttaaacgaac actctcatga gcttctaatc cacattcctt ccttttcctt ctaagttacc  72583

atttcttaaa aatcttttag aagtttcctt gatagggaaa acacaaatta ttgaggaatt  72643

tttctttctc ttgacatctg tttatagtta ctctcttgtt ccagcagtgg atatttcccc  72703

tccatgtttt tctttgtcta aacatatgtt caaaacaaaa cacttttatt cttctttgca  72763

ggttttacaa ggatcaactt ttagttttga aacctgctat tacttttaga ggccattttt  72823

tttttctcta ataatgtgag ttcatgcggg ctgaagtaat tggaatactt tatagaaaag  72883

attgaatttg tcttctctct gaactctagt ttgaatttct aaattttatg aatcatctag  72943

atattaaaga ggaggggcat atcaaagagg agaaccctag cagagataag aggcaagagt  73003

aaatgtttca tgtatgggta agagtggatt tgtatttacc taagtaaagg tagaccctgg  73063

acaataaggt tggatagatg tggaggtggc aaaccatgga gggtcttgta ggtcaagtgg  73123

atgtttttag acttgaagtg ttaaattatt atctgaaatc attaagagtc tttttagatc  73183

cttgagcttc ttgagaagac catggatatt atgcagttat tatataatgt tttaaaatag  73243

taagtatttt agtttaactg tcttatgtaa ttccatataa atggatgcat gttctttaaa  73303

aatgttaatg tatttcagta aatcaaaata tactttttga ctcatcattt aaaggaggcc  73363

ttcagtgaat gctctgtaga ggattatttt ataatactaa ttttgatatc ctaatttatt  73423

tgttataaag tttagaaggt ttgaagaatt taaaatatag tgttaataaa cacactgaac  73483

ttttcttttt ttatcttgta tttttatata gtacaacaga aaaaagatga aatgtgaata  73543

gtaaagagtc tgtgattgtt gttcatag g gcc  cac caa gct ctt cct  cga     73593
                                 Ala  His Gln Ala Leu Pro  Arg
                                 2005                2010

gat tct gtt gta  gaa gat tta cat tta  caa aat aga tac ctc  caa     73638
Asp Ser Val Val  Glu Asp Leu His Leu  Gln Asn Arg Tyr Leu  Gln
            2015                 2020                 2025
```

```
gaa aaa ctt cat  gct tta gaa aaa cag  ttt tca aag gat aca  tat     73683
Glu Lys Leu His  Ala Leu Glu Lys Gln  Phe Ser Lys Asp Thr  Tyr
            2030                 2035                 2040

tct aag cct tca  gtaagtgtat atcttttatt attttttttct tttttccatg      73735
Ser Lys Pro Ser
            2045

ttaaaatgca tgaaagtgaa atcaacttct ttcttaatct ggccaaaagc attacatctt  73795

tctcattaat agtaatacag taaattcaac ttttattttt aacaggtagt gatgtgtaat  73855

aatttattta atccttttta acataataac agtaaactta agattcttaa gcttttcata  73915

aagctcataa atgatttcta gaaattttaa atatgtagtt atcattatgt attttgctgt  73975

agcagcagta tacagttaaa taaaatagga aaacatgttc caagactgtt ttcattcaaa  74035

tatttatgct atatttttag cttataaaaa ctcattaatc attaatgtaa aattatttgt  74095

tggatttttt aaatatttag tgtattattt ttgtttcttt tttctttcca tgtttcttca  74155

ttcttccacc ttaagcagaa tcaggtgtgt gacacaacta tgttttctat ccttgttacc  74215

attattaata aatacaaggg catgatattt ttcacaaaag aaacactttg ttcagaacca  74275

aaaaagatca tggcaacagt cagaattaaa aatggtaaaa gactaggtgc caaagatgac  74335

ttacataatt gggtacctag aaatattcta tggtattaca gtaatgatga aaaatacaaa  74395

ttagaacaca ttttagatcc tattgagtta aataaatcag agtcaagacc aaacaataaa  74455

taaagtcaat ttacgtcaac aaatggtaag ttggcagatt ttaactccct ttttgaaaat  74515

gaaccatgat cctaaggttg gtaaaattaa tcaagaatgt tgtcaaaatg ataaagataa  74575

aaatgaggaa gagaataaga taggcaagag tgagaaagga aagagacaca tagctgaaaa  74635

tgtgagtcac aacaactaca tagatccgta gaatctgcta tggaggactg tgattatgtg  74695

acagttgctg atgccgtggc ttagtgagct gagggtgatg cacaggcagg cgatgtaact  74755

gatgcgtcag tccagccaag aaaggacgcg tccctggttt ggctacgtgg ccgtccttta  74815

tttctttgtt aactgaattt tcttatagta agtagcttac gtacatatat agtgcaaatg  74875

ggaaagtgtg taagatttag aaaaagcatt aactattagt aaactttatc ttaagctcta  74935

acttttgatt agttcctaca aaaattagtg aatatgcatt ttctaattta gtgctttttt  74995

tttttttaca attggtgttc acttaatgtt atattagata aatgaatagc aaaaataagg  75055

tactttagag ttgattgttt tgccttacaa acttctaatc catccagctg tatttagaag  75115

taagatctca ctacagcgaa ttatatcagt aaaattttgt tacagtgttg tgcagtgtcc  75175

taagatgtat actaagttcc ttcagtggct ttttttgcca tgttttataa cagataattt  75235

tgttataatg agaaaaggaa acttggatgt gttgctgtct atattgtgtt aggctcaggc  75295

aggatgctgt ggcttactca tttaatcact ttgggaggca ggggcaggaa gattgcttga  75355

ggccaagagt ttgagatcag cttgggcagc atagccagac cctgtctcta caaaaaaattt  75415

agacagatgt ggtggaacac atttgtagtc ctagctatta gggaggctgt ggtgggagga  75475

tcatttgagc ccaggagttt gatgttacat tgccctattg cactccagac tgggcaacag  75535

agtgagacct gtctctaaaa taataataat gataatgata aatggtgtta ggctctgtgc  75595

ctaagtatat ttttcacata ggctgggtaa agtggctcat gcctgcaatc ccagcacttt  75655

gggaggccaa ggcagcagga gcatttgagg ccaggagtca aagaccagcc ttgagagacc  75715

ccatctctac cagaaaaaaa aaaaaaaaga aacaattagc tgggtgtgat tgtgcacacc  75775

tgtagtccta gctactcggg aggcagaggt gggcagatca cttgagccca ggagtttgag  75835
```

```
gttatagtga gctaagattg tgccactgca ctccagactg ggcaacagag caagactgtc  75895

tcaaacaaaa acaaacaaac aaaaagcact ttgcagaata tcagtctaac tctacagttt  75955

atggactttt tatgtacgta ctacttttgg ctagcttaca ttgagataca gaataaaagt  76015

ttgttcatag catttatcgt tttttcttt atactgtcca cctgagatat tccagtcacc  76075

taagtcatgg aaacatcaac taaaattaaa tatctatgtt aagagaaaat ggctgaaagt  76135

gatttaattc ataacacttt ttttcacatg ctaataaata agagtttgag acttccacta  76195

ggcattatct ctaactccta tccactaaga atttgatttt aagtagttga tggcttttaa  76255

ccggattatt cttctgtaag agtttggaag tctcgtgaag ttcgttatac aagaattctg  76315

tttacaagag agcattacat tagaatttgt ttttcagaaa tttggactat ctcaacgaat  76375

acctttagtt ttattatttc aaaatgcaag ggaaaaaatg agccataatc actaatagta  76435

actgcatcat attttagtga gaaatgtgtt aaaaatatcc tcatgtgaga tcttccttag  76495

atagaattac cctctactct aatatttaat atattttata tctaccaatc agtgatatta  76555

ataggtgttt atcatttgct gaatcaaata ggtacaacag aagacaggaa gtttgggaga  76615

tagaagagct cagggacagg aaatcacaga tgtccatatc tgaaataacc ttaaaagtta  76675

tcctgtctaa tgccttcact tataaactgt agtggtagaa tttgcctagt attaacctaa  76735

tagtggtaga tttgaatgta tacttgggct ttcttattaa gtggaaatgt attcctgtga  76795

tttacatata tcaacaaaaa tgtttgtctt ctttttttg ctacgacata tgtgcatgtg  76855

cacacacatc tcctcaaaca aaaatcagat ggacacatgc agtcattgga tctaaaagat  76915

gttataaagt tgtgtataat aggtatttta taataatata ttttaagacc cataatgtcg  76975

gtggagtaac tgactttaca gcccatcaag ccaatagaga gagaaaggag aaaaaaatga  77035

aagttgtgct gaataattaa aaaaaattat ttcctatgat gcttataaca gtcctatgag  77095

gtaggtggta ttctaattta tagaaaaaat gcatagaaaa atataattaa gcacagttaa  77155

aaaaaataaa gtttagaatg agaagtaaca acataaataa tgacccaatg tagattcagg  77215

tcaaaagaaa tgaaaatata atattaatgg ttttcaaaga gggaaccatt actttagctc  77275

aaagaatgaa ggagggcttt ccgaaggagt aaagaattat ggcagttctt ttgtagccta  77335

gtgtattcat ttgctaaggt ggctgtaaca gactactaca gatttggtgg cttaaacaat  77395

agaaatttat ggtcttagtt ctggagacct agaagtccaa aatcaagaca tcagcagggt  77455

tgatttcctc tgcacaatca gagggaaaga tctttcccaa tcctctctcc ttggcttata  77515

aatgtccatg ttttccctgt ttctttttat catcttcctt ctgtacatgt ctctgtgtct  77575

aaatccccaa attttctctt ttcataagga taccagtcac agtcgaatag ggtttaccct  77635

gaaatctcat tttaacttga atacctctgt aaagacccag tctccaaata aagtcacatt  77695

ctgaggtact ggaaattatg actttaatat ataaatgtgg agggtaaggg gaacacagtt  77755

caacccataa cggttagata acaatcgtgc tttattttgg actagtaaaa ccaccataga  77815

tcagtttaac cattatgaaa ttatacatga aggcattata tgtatggaca ttattaagtc  77875

atacttgctt tgcttccatt gtaattaaaa caaaccatac tacctttgtt ctgcaagttt  77935

tgtattctaa cttatttatt tttggctttc accagaacac tccgattttc tcatattcct  77995

ttgaggaaaa aaagttacct tttgacagta ttttcttatc cagtatgtct tttatggctt  78055

ttatttatta aactttaaaa atattcctaa tttcatttcc ctgaag att tca gga     78110
                                                    Ile Ser Gly

ata gag  tca gat gat cat tgt  cag aga gaa cag gag  ctt cag aag     78155
Ile Glu  Ser Asp Asp His Cys  Gln Arg Glu Gln Glu  Leu Gln Lys
```

```
    2050                2055                2060

gaa aac  ttg aag ttg tca tct  gaa aat att gaa ctg  aaa ttt cag     78200
Glu Asn  Leu Lys Leu Ser Ser  Glu Asn Ile Glu Leu  Lys Phe Gln
    2065                2070                2075

ctt gaa  caa gca aat aaa gat  ttg cca aga tta aag  gtgaatttaa      78246
Leu Glu  Gln Ala Asn Lys Asp  Leu Pro Arg Leu Lys
    2080                2085                2090

tgttttttat taggaaatct aatgcctaaa actccttcct tagttgttat gtttactttt  78306

attagcttat taagaagtca aaaatgcata ttcctaatat atcatggtga tggtatactt  78366

tatacatttg ctctttagca tttatttgtt gaaggcctac tttatattaa acactcctcc  78426

agatgctggg aaacagcagt caaaaaattc cttatactca taggacttac gttctagtgg  78486

agaagactga caataaacaa gtcactaaat agtatgtcat ctgatgttag tgctaaggag  78546

agaaataaag catgattggt gtaaagagta tggggagaga gaaggggtgt aactgaaaat  78606

agagtagtaa gggaggtctt ccttaataag atgatatatg aacagagagc taaggagggg  78666

taaaggaagt gagtcataca gatactagaa aaataattac agacaacaga aatagcaagt  78726

tcagatgtcc taaggtggga ggatgcgtgg tatatttcat taaaaattat cacactgtaa  78786

aatataagaa taatttgttt cttttagaaa ttttacttta ttctgatatt aataatgatt  78846

ttttaatctt tggttttcca agtcttaccc tatttatggg aatctttttt ttcttttggc  78906

tagctaattg cttcagtttt gttttctaat ctagaatgtt agcaatctgt taattccact  78966

ggtaatgata tagttaagct atgtcttgct tctcacactt tatttattta tttactcagg  79026

gcactaatct gccatttttt cgcacttttt ttcctttttt ttttttttgg tactgcttct  79086

tattctggtt tttacattga tagaaccaat gttagacgtt catttgcctt ttgctgtgta  79146

tatttgggta aggatctata tgtgcaatat atgggacagt taaaatcaga attctaaatt  79206

tgtattattg catcaggcaa taatgtggga aataccttga catttcatat acacaatatt  79266

cttgtattaa tttaacgtct tagttcaaaa tcttccttgt taatatagag accctattat  79326

ttggtttggc aatacagttg aagagattga tggttcttat gaattgtttg ccttttcttt  79386

tcaatggctg tagctatgtt aaattattac atgtttgctt gttatctttc ag aat caa  79444
                                                          Asn Gln

gtc aga gat  ttg aag gaa atg tgt  gaa ttt ctt aag aaa  gaa aaa     79489
Val Arg Asp  Leu Lys Glu Met Cys  Glu Phe Leu Lys Lys  Glu Lys
        2095                2100                2105

gca gaa gtt  cag cgg aaa ctt ggc  cat gtt aga ggg gtatgtgaga       79535
Ala Glu Val  Gln Arg Lys Leu Gly  His Val Arg Gly
        2110                2115

atttaccata catttgtttt ggtttcagca gtgataagcc agaaatgaaa agtttagata  79595

tgttgtaaaa gtactgatat gcctctacaa gtgccctgta gtttcagtgt ttattctgca  79655

tctgtaatat aaaacagtaa gcatttctat gtgtctcaaa gtattttatc atctgttata  79715

ccttacatac tttcatctct ctttttattg aatatgcctc cataccttga aaacatttaa  79775

cttccaggaa tccttttgtt tatggaggta actgctaact ggtccttggt ccaatgctgc  79835

cattttgtaa ccatttgtta tgatatcttc ccagcttggt ataatgtttt ataattacat  79895

tgttcctccc cctctttttt tgtgttcttg taattttctc cctatgttat tttgtattca  79955

ttttatataa tgaataaatg ttgcttatga ggtcaaggcc aaagacttaa gctcctgttg  80015

atttcatgtt gctgagtgtc ataaatggaa gcaatcataa tgcagagtca ttctggtagt  80075

aatattaaat atatgatgga ttcagtgaaa atattatgtg ttattagaaa aatattcaga  80135
```

```
acaggccggg ggcagtggct cacacctgta atcccagcaa tttgggaggc cgaggcgggc  80195

agatcactgg aagtcaggag ttcaagacca gcctggccga catggtgaaa ccccatctct  80255

actaaaaata tgaaaattag ctgggcatgg tggctcatgc ctgtaatcct agctactcag  80315

gaggttgagg caggagaatt gcttgaacct ggcaggcgga ggttacagtg agccatggtc  80375

acacaactgt actccagcct gggcgacaga gcgagactcc atcttttaaa acaaaaaaaa  80435

aaaaggaaaa atattcagaa cagtatcttg ctggcagcaa catttgtttc atcaatgaaa  80495

atatgtgtta atttgacctt ttctatctaa gttaattatg aaagtgcata ctaaaatgat  80555

gtaaaagttt atatttcagg attattctta ttcatggatg attaactaaa atgcaaaaag  80615

aaattaagca tactgtttgg ctaaactgtt aaaaattatt tttattttaa atgataagca  80675

gttaaactta ttaagtgatg actcatctct gctgatatat ttatgcaagg tttttttattt  80735

cagataactc ttctatttat attaaacaga aactgtattt ctaagcaata gcatttctta  80795

gagaaaattg cctctattat gttgcaatta aaatttaatt actcatgagc tctttaaaga  80855

cacaatttct cttgtgtggt tttatttcat ataaagaaaa actctgatat actggagaga  80915

acattagcta aatagactat ttagacttaa tcattttgat cagacatcaa ggctagacta  80975

tttaagctgt tacttattag ctgcatgatt ttaggaatgt caaatttcct aagtcttggt  81035

tttcttgtat ttaaaatgga aattataatt cctatctcat agaattgttt taaggatgaa  81095

ttgaattaat acagttttga cttcaaatat taggaattat tgagtataat aagcctgttg  81155

tattgttggt acttcgtatt atacttacta aaatatttga ttaaagattt aacatattct  81215

ttcgtag tct  ggt aga agt gga aag  aca atc cca gaa ctg  gaa aaa     81261
        Ser  Gly Arg Ser Gly Lys  Thr Ile Pro Glu Leu  Glu Lys
        2120                 2125                 2130

acc att ggt  tta atg aaa aaa gta  gtt gaa aaa gtc cag  aga gaa     81306
Thr Ile Gly  Leu Met Lys Lys Val  Val Glu Lys Val Gln  Arg Glu
        2135                 2140                 2145

aat gaa cag  ttg aaa aaa gca tca  gga ata ttg act agt  gaa aaa     81351
Asn Glu Gln  Leu Lys Lys Ala Ser  Gly Ile Leu Thr Ser  Glu Lys
        2150                 2155                 2160

atg gct aat  att gag cag gaa aat  gaa aaa ttg aag gtaatttttt       81397
Met Ala Asn  Ile Glu Gln Glu Asn  Glu Lys Leu Lys
        2165                 2170

ttaatgtgat catttttagg ggaatatttt acgttttgtt actatttagg aaaatttcaa  81457

atatgctcat tactatataa aatggcttta atgaatacaa tacatatttt ataaatatag  81517

aaaaaaactt atgagaggca aggctaaggg ttatagagta ggtctacctg atctttcttg  81577

ttatttcaag accaatactt ttcacttttc tctctgacag catagattaa ttacctgtgt  81637

ctctcttttt tttttctttt gagatggagt actgctttgt cacccaggct ggaatgcagt  81697

ggtgcaatct tgactcactg caagctctgc ctcccgggtt catgccattc tcctgcctca  81757

gcctccccca gtagctggga ctacaggtgc ccaccaccac gcctggctaa cttttcgtat  81817

ttttagtaga gatggggttt caccatgtta accaggactg tctcgatctc ctgacctcgt  81877

gatccgccca ctgcggcctc tgtgtctctt tgtgaaaata cagatgccca agctcccatc  81937

cctgaaattg atttaattat tttagggtgg gtcctgacac agatatgtat gttgttgtta  81997

ttttaagtca tcaatttatt ctaatatgta gccaacgttg ggaacttcgt tctcactaat  82057

attcaaatga agactttaat tctaatcata tcaaatatgg tttctaaaac tactttgaag  82117

atttatgagt ttataagatt atcttttatt tccttgtttt gataatgtat actttttatt  82177

ttgtttgttt ttttactag gct  gaa tta gaa aaa ctt  aaa gct cat ctt     82226
```

```
                    Ala  Glu Leu Glu Lys Leu  Lys Ala His Leu
                    2175                 2180

ggg  cat cag ttg agc atg  cac tat gaa tcc aag  acc aaa ggc aca     82271
Gly  His Gln Leu Ser Met  His Tyr Glu Ser Lys  Thr Lys Gly Thr
2185                2190                 2195

gaa  aaa att att gct gaa  aat gaa agg ctt cgt  aaa gaa ctt aaa     82316
Glu  Lys Ile Ile Ala Glu  Asn Glu Arg Leu Arg  Lys Glu Leu Lys
2200                2205                 2210

aaa  gtatgacttt tatgactgat tataactttt gatttttatt ttacttaata       82369
Lys
2215

cctcttggaa aaactggaag tagatccttg atgagagtgt ctgtaaaggt agatattaag  82429

agattgagga attgtgtttc tatgcctgct gtcatcacat tccaccatga aaaacattga  82489

taataaaagt taatacattt aggctgggca cggtggctca cgcctgtaat cccagcactt  82549

tgggaggcca aggcgggtgg atcacgaggt caggagatcg agaccatcct ggctaacacg  82609

gtgaaacccc gtctctacta aaaatacaaa aaattagccg ggcgtggtgg cgggcgcctg  82669

tagtcccagc tactcgggaa gctgaggcag gagaatcgct tgaacccggg aggcagaggt  82729

tgcagtgagc cgagatcgca ccactacact ccagcctggg caacagagcg agactccatc  82789

tcaaacaaac aaaaaaaaga aatgatctac gttgcttaca cataccttat gcttatagct  82849

aggtctcgta agcattagga agtcaaaaca aagaatcttt tacatgtgta aaggtataaa  82909

ctatcccatt tttctaaaaa tatagaggaa caaagtgtca aatttaaagt aatcactagt  82969

aactaaatat attcctctga cctcattttc gtgatctgtt gttctaatta ttattggcca  83029

tattgctgct ttaaaggaga gatgttgaat ttgttgaaat tttaatcagc atttagagcc  83089

ccaggttatt tttgttttcc aatttgtaat gataattttg aatacactga atctatgaga  83149

acagtattat gttttctcat aaaatactaa ttagcattta atgatag gaa act gat    83205
                                                    Glu Thr Asp

gct gca  gag aaa tta cgg ata  gca aag aat aat tta  gag ata tta     83250
Ala Ala  Glu Lys Leu Arg Ile  Ala Lys Asn Asn Leu  Glu Ile Leu
    2220                 2225                 2230

aat gag  aag atg aca gtt caa  cta gaa gag act ggt  aag aga ttg     83295
Asn Glu  Lys Met Thr Val Gln  Leu Glu Glu Thr Gly  Lys Arg Leu
    2235                 2240                 2245

cag ttt  gca gaa agc aga ggt  cca cag ctt gaa ggt  gct gac agt     83340
Gln Phe  Ala Glu Ser Arg Gly  Pro Gln Leu Glu Gly  Ala Asp Ser
    2250                 2255                 2260

aag agc  tgg aaa tcc att gtg  gtt aca ag  gtaggaacag agttttaaac    83389
Lys Ser  Trp Lys Ser Ile Val  Val Thr Arg
    2265                 2270

ttgtacaaag tttaatcatt tcaaattttg gcattgtttt aaaagacaac actattctgg  83449

ataacctggt ttcttcctga tgaacagttt gtttggttgt tgttttaaca taatactttt  83509

tttctgttgt agtattgttg gagacttttt cttccttgaa atgtttaact tgtttaacct  83569

tgtttgggtg gcagggcatg gaacagtgta gagctggggc tgggcgaagg agttggagct  83629

gtgtgtgcgt catgaagctg tcatcagcta tgagcctggg ctgaggctgc tcagcttctc  83689

ctgggtgcta tttttctcca actgcagctt cagcttcttg attgtataat ttgcttcctc  83749

aagtatgagc caggaataat tgagctgtct tgtcacaatg tgtggcatac tggatctagg  83809

ctgtgctgca atgcttttag agttatatcc tgggcaactt tctcttcaga tagccccaag  83869

agatgaattc agcaccagct ttgatgtttt actagcttct gctttctggt acttgatttt  83929

ctcccacccc gaacacatgg gattccaacc tgtgaaacta atttttgtgg ctatgaaaga  83989
```

```
ggtagtggta gtttatgagt aaacattcag tctgttgcca ctatcatcat gtgtggttca  84049
tcatgactgt gatgagtagg taaaaggctc tttgtgtcat tctcatttcc aattttaagc  84109
agctgcttca aggagtctgg aagtcattga ccagtgggat cctgcctgtg tcttttccca  84169
ttaaagccat cctgtatgaa gtggtatcct ttaccatcta gcacatctgc cgcccccatt  84229
tcaaaaggca tactcatctt tatctcaaca ttctcataca gttccttatg tccatgcacc  84289
tccaatgtcc cctttgatgt ctttgaggtt ttcatcttcc atgtctgcta tttggaatgg  84349
tcttgatggg aggcaagata gtgatcacta caactaggat gggagtctta gtaccgtgag  84409
gctacagcaa gtcccacaga gggcctgctg cactgtactt gcctctgtca accaagtcta  84469
aggagaaaga ttaagcaggc atattaaagg acagcccaga tggacatgaa gtcctggagg  84529
aggccttggt tcctgtccta atactaaacc tagagtaccc agaatccaca cttctccact  84589
ctagctctca cttttcccat ctacacactg ggaaaaatta ttctgtcaga aagccagtgt  84649
caaggtgaga acaaataaca aatgtgatga tatggagtgg gagaaggggt ctcttctact  84709
gtcttattgg accctagcag tggctctgag ccagcagtcc tgtcagttga tttcttggtc  84769
gttcctttgt tttcttctat aatcacatgt ggactcagaa tgaattttga gttactctga  84829
aatctattta ttcaacagat atttacttag tacctcctat tgccagactc tgctttatgt  84889
tggatattat tttttaaaag cccaccttgc ctagatttcc tcaaaggacc aggtggcttc  84949
cctggttttg aaagacccta attcttacta tgatcttaag taaattatat cctttctgtg  85009
ggctcaagtt ctttctaaga gggctctttg gggctacaaa agaaattgtt agtgcaaaaa  85069
gagtttataa ggtttataaa tggttagtag aggtgatgat gatatttaac cataattgaa  85129
gatgactttg cattttagat catatacgtg tttttcgtct gagaacgata caggtcactg  85189
agcataccat aagccttcag taaatcattt gcagaagaca ttgcagaaga cataagtcta  85249
agtagaaatc tcttgacaga gagaaggctc gttttgatcc ttgacctcaa atttaggttc  85309
cctaaatcca ttaaaaaaga gaaagaaaaa gaaaaaaagt tactaaagtt taaatctggg  85369
aggattatat acccttctca ataaagcagt ttagagagat ctcttttggg acccatgaca  85429
caggtcttgc tcatgctgac atctttatag ttgctttatt atttattcaa caaacttagt  85489
aacacgtatt ctatgtcagg ccttttcctg actactggga caaaccaggg tgatgtgggg  85549
gctgttttag atagggtgat cagaggaggc ctctctgttt gggtggcttt tgaatagaaa  85609
attagatgaa gtgaaggagt aagcttctga tatttcactg tttacttgtg gtagatctgt  85669
gataatctct gtcaggttaa aaacattccc ttctaatcta agtttctaag atctatcaaa  85729
agctgtttga atatatttag acaatcataa ttttcctttc ttgtattatc ctagcagatt  85789
ttgttgccaa agctatactg gccattttaa cttagaatgc agtctttcta ttcatttctc  85849
tggaaaagtt tggatattgt aagcattatt tttctttagg tatgatgaac ctgcagaact  85909
gtttggttca attatgaatt tttttttct ggagtctgta tttttttgaa ctattaatca  85969
tttctttaat gattataaat ctattcagat ttttacaagc tttatccctc tcccatcata  86029
cactattttt cttacccatg cttttgcaca attttttcct ctcccttagt gttttcctac  86089
ctagatacct cctatgtgtg tctgtgtatg tgagaaaagc tttttatttg ccatctttat  86149
atttctaaga atatctagta atacagaatt ttatattctg aagaatttta ctttgcattt  86209
tcttattttg tgattgaaaa aaggtattaa ttttaaaatg gtcaaatcag gctccatcct  86269
tggaaaatac ccaaatcctt tattttgatt gggccatctg ttaattaggg ataccttatc  86329
```

```
tcttgccacc actttttaat gctaaataaa tatgtagcta aaactttgac tagaagaaac  86389

agtaaaataa gatattcttg cttattttta gtacagttat ttgaactgac ttttaaatca  86449

gtgacataaa ttatttgcca tgtctatact ttttttcctt atacttttag a atg tat   86506
                                                          Met Tyr
                                                              2275

gaa acc aag tta aaa  gaa ttg gaa act gat  att gcc aaa aaa aat      86551
Glu Thr Lys Leu Lys  Glu Leu Glu Thr Asp  Ile Ala Lys Lys Asn
                2280                 2285                 2290

caa agc att act gac  ctt aaa cag ctt gta  aaa gaa gca aca gag      86596
Gln Ser Ile Thr Asp  Leu Lys Gln Leu Val  Lys Glu Ala Thr Glu
                2295                 2300                 2305

aga gaa caa aaa gtt  aac aaa tac aat gaa  gac ctt gaa caa cag      86641
Arg Glu Gln Lys Val  Asn Lys Tyr Asn Glu  Asp Leu Glu Gln Gln
                2310                 2315                 2320

gtaagtaacg taatttttct ttacatgata aaataatgca taatatcgca agatgttcct  86701

tgcattgtct tatatagata aaaatggact ctattaagaa gacccatcta actgaagggc  86761

accccattca cccatttgct taagccagaa actttggatc atcaacgact tcattctttt  86821

cattctccac attttctatc attaaatcat gtcagctcta ttttcaaact atatcctaaa  86881

tatgaccact tcttggtatc ttgagacatc actaccagtc ttgtccaagc tattgtttta  86941

tacctgaata actgcaataa tttccaagct ggtatctcag cttccactct tggattattt  87001

caccctattt ctatttctgg gctgtctcca cacagttgcc aggtaaccct tttaaaacat  87061

aaagcacatc acaaagcaca aagtcctatc ctcagaatct tccagtggtt ctccatcacc  87121

ctaaaataaa acttaaaagt tcttttcata tcccaaaaca acatatgagg tctggcaccc  87181

agttttcttc ccaatctcat cttctactac ttttcccttc atttcattca caatgtttta  87241

accacagtaa ccttctttca gtactttaaa caatccaaac tcgtttaagc gtcaagtcct  87301

tatacttgtt tcctttgttt agaatactgt tcacccaaat attctcatag cttgctccca  87361

gacttcatgt ctctgctgaa atagaggctc cttagagaga ccttccctaa ccctaaccct  87421

aaccctatac tacttgccat cactctttat cctcttaccc tggattattt tttcttgata  87481

gctcttccta ccatctggca ctatattaca tcatatcata ttaaacacac attctttgtg  87541

cttccccact aaacaaggac catgcaagat ggaacattgc cattttgttc actgctgtta  87601

gcctctgtgc ctaggacaat gccagttatg cagtagttac tcaatacttg ttgaatgaat  87661

ggtgaataga acatagaaat ttgcctatgc gtgcttttga aaaccatatt ttaatattac  87721

gctttgttaa aaatgtgtat ctttataaat cctcatattt ccatggcaaa ccttatcttc  87781

taacttttca ttgtcctcaa ag att aag att ctt aaa  cat gtt cct gaa      87830
                         Ile Lys Ile Leu Lys  His Val Pro Glu
                                         2325

ggt  gct gag aca gag caa  ggc ctt aaa cgg gag  ctt caa gtt ctt     87875
Gly  Ala Glu Thr Glu Gln  Gly Leu Lys Arg Glu  Leu Gln Val Leu
2330                 2335                 2340

ag   gtacatcatg tattcatatg actactttgt ttttttcttt aaaaaaaaaa        87927
Arg
2345

ttattagttt ttatatactc cgaattgcta caactagaga caagcatttt tcgactttac  87987

tgcctaacag gcttattagg tccttatttc ttccctctaa tgctaatcac tctttttcat  88047

aatacacact agaaaaaaag gataaaccca actctaagtt tccagtttgt aatttagttt  88107

aaacttttct aagagcatag aatgagttaa accttagctt cccagaggaa aatactaatg  88167

aaagagaaca agtaattttt ttactttcag gggtctctgt agcctgcttt cattaagctc  88227
```

```
ctcttataac gaaaccacac ttgcaaatgc catcaggtca gatattaaga aaaacgtgaa  88287

ggcttttgta ttccaggctt tttgtttgag aatggtgaca ttgtagcatt gagagtaaat  88347

gtttacttcg ataaaggcta gcttgttctg attactgtac atcactagtt cataagaaat  88407

gcccatatat tttatgaagc aatatctgct ttattttttt aacacattat cattgtgttc  88467

tag a tta gct aat cat cag  ctg gat aaa gag aaa  gca gaa tta atc    88513
      Leu Ala Asn His Gln  Leu Asp Lys Glu Lys  Ala Glu Leu Ile
                     2350                 2355

cat  cag ata gaa gct aac  aag gac caa agt gga  gct gaa agc acc     88558
His  Gln Ile Glu Ala Asn  Lys Asp Gln Ser Gly  Ala Glu Ser Thr
2360                 2365                 2370

ata  cct g gtaatgtatt ttaaaaaaca tgttagctac ccccaagttt ttgaatttgg  88615
Ile  Pro
2375

gtttgccttt tttttttttt tttggctcag atttctgatc attgtctccc tgtaaaatcg  88675

aattcctgat aagctttggg tcttttgtct ctctgtgcta ttaatataaa aatattccca  88735

tttttctctt tgtgttgttt atactataga gtagcaagta cccaagtgtt cttctctttg  88795

ttctccatct gggtgttaca gatttaatca caatacagtg ctaagcaatg aatactaaat  88855

ctgttgcttc cagtttctaa gtataggctc tttcaagtcc tctgaacatt tttaaaaact  88915

gcaaataagt aaatactgcc tatatttttt tccgtttaca aagtaaaaag aaaatctttc  88975

tgctcccttc cattcccatt caaaagtgat tactaatcat tcctcattcc tgcatataca  89035

tacacacata ttttgtatac atatatatca cacatatgca tacatgtgtt tgtatgttca  89095

tatgtacaat gtacatatcc tcattatttg tggattctgt attttctaaa tcacctcctc  89155

actaaagtgt gtatgtaatc ccaaatcaac actcgcagca catttgcaaa catccacaga  89215

gccttggaaa gtttgaataa tccaacctac atgtccccag cagaagtcca acaaggcagt  89275

gctcagtatc ctcatttcag ttttcataga gaaatgagca gaggatggag acagtagagg  89335

gcagcacagc atagtgcaag aagctgtggc tctggggcct ggtggaaggg atttgaatcc  89395

caattctgag gcttgttact gctctagcct taggagagtc atgtaacact tctgaatctt  89455

gttttcttat gtaaataaat agaatttacc aggatgagtt atctttagga tttaagatta  89515

tcatctgtgt gagatatgta ggtgtatgta tatatatgcg tgtatgtata tatatgcgtg  89575

tatgtatata tatgcatgtc tgtacatatt tcccgtagca gcagtggttt gatattcact  89635

aattgggcta actttataga ccaaaactac tatggataga gaatactttg tttgcattta  89695

cgtatatata ttttcttggc aagtaacata aaattgaact aatactatac acatttctag  89755

catatttgcc tttaacagtt tatcatggac atcttttgag gtctgttcat aaattatctc  89815

atccatttaa taattccata gtgtattatt gcatgtataa gcacatcgaa ccatttatgt  89875

tttgatggat atttagtttg cttccaagtt tctgcttcta taaaatatga ttaatctatt  89935

gacctaatta tgccattgtg ataggatgat agagatgcca ttctctccaa aggattatac  89995

caatttatat ctgaactatc tttgactatc tcttgtagct ttttcagtat gctatgtagt  90055

cctattacta atttgtaata aaagccatca tgtgtgagtt gtactagaca ctatgctaat  90115

tgccttacaa gcattctata tttacaacca tatatgatag gtattactgt ctccatttta  90175

tgtgataaac aaattcaaag tggttaagta accattccct aagccagcta ggaaatagag  90235

gcaggattaa aatctaaatg tatgaaactc cacagctcct tggcattcct agtccttaac  90295

ccgctatgct atgctacgtc ttggtaacta aaagtacata ttaaatactc tcaaaatatg  90355
```

```
tctcatagca gccagcttgg tatgtacact agacacagta ttaatgctgt tgatgtgagg  90415

aaaattttat aattttcctt ccatccatat actaaccagg cccaacagtg cttagcttct  90475

gagatcagag atcaggtgca tgtgcattaa gggtcatatg gccatagata gttctctaat  90535

ctttccattc ctcagtttct taagggaatt tctgaaccct caaaattcct tatttcctaa  90595

gtagacagat tacctgtcat ttttcaaaga ttaaggctta agatcaaacc agaactgttt  90655

tggaaattct aaatcactgt ctatataaat ggcaagataa cttttaagat atttatacca  90715

agcccagtac agtagcacac cacacctgta atcccagcac tttgggaggc tgaagtgggt  90775

ggatcacatg aggtcaggag ttcgagacca ctctggccaa catggtgaaa ccctgtctct  90835

actaaaaata taaaaattag ccaggcatgg tggcacttgc ctgttatccc agctacaagg  90895

gaggctaagg caggagaatc gctttaacct gggaggcagt ggttgttgca gtgagccaag  90955

attgcaccac tgcactctag cctgggcgac agagtgagac tgtctcaaaa aaaaaaaaaa  91015

aaaaaaagat acttgtccca gccatgaaaa tgtttgctgc cccttacttt cgcaaacttt  91075

tagtatttta ttatttttca atggctgtaa aatatgactt attaaatgta gtataatata  91135

aagaaaagag atatctagca aagatagcat taaagcaaaa atcctatttg cctgctgata  91195

aagttagagg tgttaacttg gagggtgaat ccaataaatt agaacttttg tgctatattt  91255

ggagactttt gttttcctac caaagtatca gggctatgtc ttacttatct ttgtattaca  91315

cagcctgcat gacacgtttt gcacatagta attgcacagt aaatgtgtaa taacctacat  91375

ggaatagcca gtgttgtgtt ggatagcggg agcatttggc tagcttatgg ttatagtccc  91435

ttacccaaca gtctgctttt cttctgttgt acttttagta cctaacaagt ttccctggct  91495

ttaggatttt ttccatgtaa aatttctatc atgtgaagaa aaaataactt ggcctacact  91555

tctaatacct agcacatacc tctttctgcc tgctatgaaa ttataatact tgatggaggg  91615

aggcagcatt aagtgtttac atcctgaagt atttcagcca taacatccag tgttttccag  91675

gttctaggtt tcataaaatg tatctctgtt ctctagaaca aatccattac cttgaactca  91735

ttcgtagtgg gaaaaagctg agtctaattt gtatgacttt ttcaacag at  gct gat   91791
                                                        Asp Ala Asp

caa  cta aag gaa aaa ata  aaa gat cta gag aca  cag ctc aaa atg     91836
Gln  Leu Lys Glu Lys Ile  Lys Asp Leu Glu Thr  Gln Leu Lys Met
2380                2385                 2390

tca  gat cta gaa aag cag  cat ttg aag gtaatattta attatatttt        91883
Ser  Asp Leu Glu Lys Gln  His Leu Lys
2395                2400

agtatcgttt tgtgaaaaca gctgttgaaa actattttca ttaccatctt taactacgta  91943

tcctaaaaaa ttcagtaata acatcttata tttgaccttt atattgcaaa gttaattatg  92003

ttcatctgac tattcctaac atattagagt taacaaaaaa ttcagactca acataggatt  92063

aagtagtaaa tttatttttt aattgtaaca aatatatgcc attagtatgt tcttaagttt  92123

tgggtcacat tggcaacagt gtctttattt ttttttgaa attcttttca ggaatcctaa  92183

ggttatagtt cccttaaaaa aatatttgct gttttacctc ttttaagact gtaaacagga  92243

caaaaaggca tggatatgag aattagctag tgatcactgg ctattctaaa tagtcactaa  92303

ggcttgaatt gtctcttcac cagatgcctg tcagaagtcc caaaggtttc cctgatcata  92363

ttaataactt tataaaaaat tgatcattat tcattaaata ttagatatta gtaaggaaaa  92423

tataaatgaa gtctaaacca aaactcttaa ccagactaac ttcaatgtta tgaatcacaa  92483

aatctttttg attgattgct ctattgacaa gctcttatat gcttttagag aaagattaag  92543
```

```
tcccattata agagatgata aattttagtc aaagactaga acacaactta cagaatacat  92603

aactggactt gacagttaac aacttagtta tttacactgt acaatggaac aaagaaaaat  92663

cttaattctt ctgcctttat tgctgtattt gaccattcag gaatactttg gctttcatat  92723

ttacaattaa atctccttgt tcaaacgtaa aatatgtata tttcctatat gcaactttta  92783

aagataatgt ttccattag gag gaa  ata aag aag ctg aaa  aaa gaa ctg     92832
                     Glu Glu  Ile Lys Lys Leu Lys  Lys Glu Leu
                         2405                 2410

gaa aat  ttt gat cct tca ttt  ttt gaa gaa att gaa  gat ctt aag     92877
Glu Asn  Phe Asp Pro Ser Phe  Phe Glu Glu Ile Glu  Asp Leu Lys
    2415                 2420                 2425

tat aat  tac aag gaa gaa gtg  aag aag aat att ctc  tta gaa gag     92922
Tyr Asn  Tyr Lys Glu Glu Val  Lys Lys Asn Ile Leu  Leu Glu Glu
    2430                 2435                 2440

aag gta  aaa aaa ctt tca gaa  caa ttg gga gtt gaa  tta act agc     92967
Lys Val  Lys Lys Leu Ser Glu  Gln Leu Gly Val Glu  Leu Thr Ser
    2445                 2450                 2455

cct gtt  gct gct tct gaa gag  ttt gaa gat gaa gaa  gaa agt cct     93012
Pro Val  Ala Ala Ser Glu Glu  Phe Glu Asp Glu Glu  Glu Ser Pro
    2460                 2465                 2470

gtt aat  ttc ccc att tac taa aggtcaccta taaactttgt ttcatttaac      93063
Val Asn  Phe Pro Ile Tyr
    2475

tatttattaa ctttataagt taaatatact tggaaataag cagttctccg aactgtagta  93123

tttccttctc actaccttgt acctttatac ttagattgga attcttaata aataaaatta  93183

tatgaaattt tcaacttatt                                              93203


<210> SEQ ID NO 2
<211> LENGTH: 7972
<212> TYPE: DNA
<213> ORGANISM: Homo sapiens
<220> FEATURE:
<221> NAME/KEY: CDS
<222> LOCATION: (345)..(7781)

<400> SEQUENCE: 2

atttgaagtc ctcgttccac gccttctcat catcctgaac accgagctct gggactccgg    60

cggagaatct aaacgtaaag catcacccac ggtcgtgaac tgtaggctct cctggcatcc   120

gggatcttat tctggccttg gcggagttgg ggatggtgtc gcctagcagc cgctgccgct   180

ttggcttgct cgggaccatt tggctggacc cagagtccgc gtggaaccgc gatagggatc   240

tgtcagggcc cgcggccggg tccagcttgg tggttgcggt agtgagaggc ctccgctggt   300

tgccaggctt ggtctagagg tggagcacag tgaaagaatt caag atg cca cct aat    356
                                                 Met Pro Pro Asn
                                                 1

ata aac tgg aaa gaa ata atg aaa gtt gac cca gat gac ctg ccc cgt     404
Ile Asn Trp Lys Glu Ile Met Lys Val Asp Pro Asp Asp Leu Pro Arg
5                   10                  15                  20

caa gaa gaa ctg gca gat aat tta ttg att tcc tta tcc aag gtg gaa     452
Gln Glu Glu Leu Ala Asp Asn Leu Leu Ile Ser Leu Ser Lys Val Glu
                25                  30                  35

gta aat gag cta aaa agt gaa aag caa gaa aat gtg ata cac ctt ttc     500
Val Asn Glu Leu Lys Ser Glu Lys Gln Glu Asn Val Ile His Leu Phe
            40                  45                  50

aga att act cag tca cta atg aag atg aaa gct caa gaa gtg gag ctg     548
Arg Ile Thr Gln Ser Leu Met Lys Met Lys Ala Gln Glu Val Glu Leu
        55                  60                  65
```

```
gct ttg gaa gaa gta gaa aaa gct gga gaa gaa caa gca aaa ttt gaa      596
Ala Leu Glu Glu Val Glu Lys Ala Gly Glu Glu Gln Ala Lys Phe Glu
    70                  75                  80

aat caa tta aaa act aaa gta atg aaa ctg gaa aat gaa ctg gag atg      644
Asn Gln Leu Lys Thr Lys Val Met Lys Leu Glu Asn Glu Leu Glu Met
85                  90                  95                  100

gct cag cag tct gca ggt gga cga gat act cgg ttt tta cgt aat gaa      692
Ala Gln Gln Ser Ala Gly Gly Arg Asp Thr Arg Phe Leu Arg Asn Glu
                105                 110                 115

att tgc caa ctt gaa aaa caa tta gaa caa aaa gat aga gaa ttg gag      740
Ile Cys Gln Leu Glu Lys Gln Leu Glu Gln Lys Asp Arg Glu Leu Glu
            120                 125                 130

gac atg gaa aag gag ttg gag aaa gag aag aaa gtt aat gag caa ttg      788
Asp Met Glu Lys Glu Leu Glu Lys Glu Lys Lys Val Asn Glu Gln Leu
        135                 140                 145

gct ctt cga aat gag gag gca gaa aat gaa aac agc aaa tta aga aga      836
Ala Leu Arg Asn Glu Glu Ala Glu Asn Glu Asn Ser Lys Leu Arg Arg
    150                 155                 160

gag aac aaa cgt cta aag aaa aag aat gaa caa ctt tgt cag gat att      884
Glu Asn Lys Arg Leu Lys Lys Lys Asn Glu Gln Leu Cys Gln Asp Ile
165                 170                 175                 180

att gac tac cag aaa caa ata gat tca cag aaa gaa aca ctt tta tca      932
Ile Asp Tyr Gln Lys Gln Ile Asp Ser Gln Lys Glu Thr Leu Leu Ser
                185                 190                 195

aga aga ggg gaa gac agt gac tac cga tca cag ttg tct aaa aaa aac      980
Arg Arg Gly Glu Asp Ser Asp Tyr Arg Ser Gln Leu Ser Lys Lys Asn
            200                 205                 210

tat gag ctt atc caa tat ctt gat gaa att cag act tta aca gaa gct     1028
Tyr Glu Leu Ile Gln Tyr Leu Asp Glu Ile Gln Thr Leu Thr Glu Ala
        215                 220                 225

aat gag aaa att gaa gtt cag aat caa gaa atg aga aaa aat tta gaa     1076
Asn Glu Lys Ile Glu Val Gln Asn Gln Glu Met Arg Lys Asn Leu Glu
    230                 235                 240

gag tct gta cag gaa atg gag aag atg act gat gaa tat aat aga atg     1124
Glu Ser Val Gln Glu Met Glu Lys Met Thr Asp Glu Tyr Asn Arg Met
245                 250                 255                 260

aaa gct att gtg cat cag aca gat aat gta ata gat cag tta aaa aaa     1172
Lys Ala Ile Val His Gln Thr Asp Asn Val Ile Asp Gln Leu Lys Lys
                265                 270                 275

gaa aac gat cat tat caa ctt caa gtg cag gag ctt aca gat ctt ctg     1220
Glu Asn Asp His Tyr Gln Leu Gln Val Gln Glu Leu Thr Asp Leu Leu
            280                 285                 290

aaa tca aaa aat gaa gaa gat gat cca att atg gta gct gtc aat gca     1268
Lys Ser Lys Asn Glu Glu Asp Asp Pro Ile Met Val Ala Val Asn Ala
        295                 300                 305

aaa gta gaa gaa tgg aag cta att ttg tct tct aaa gat gat gaa att     1316
Lys Val Glu Glu Trp Lys Leu Ile Leu Ser Ser Lys Asp Asp Glu Ile
    310                 315                 320

att gag tat cag caa atg tta cat aac cta agg gag aaa ctt aag aat     1364
Ile Glu Tyr Gln Gln Met Leu His Asn Leu Arg Glu Lys Leu Lys Asn
325                 330                 335                 340

gct cag ctt gat gct gat aaa agt aat gtt atg gct cta cag cag ggt     1412
Ala Gln Leu Asp Ala Asp Lys Ser Asn Val Met Ala Leu Gln Gln Gly
                345                 350                 355

ata cag gaa cga gac agt caa att aag atg ctc acc gaa caa gta gaa     1460
Ile Gln Glu Arg Asp Ser Gln Ile Lys Met Leu Thr Glu Gln Val Glu
            360                 365                 370

caa tat aca aaa gaa atg gaa aag aat act tgt att att gaa gat ttg     1508
Gln Tyr Thr Lys Glu Met Glu Lys Asn Thr Cys Ile Ile Glu Asp Leu
        375                 380                 385
```

```
aaa aat gag ctc caa aga aac aaa ggt gct tca acc ctt tct caa cag     1556
Lys Asn Glu Leu Gln Arg Asn Lys Gly Ala Ser Thr Leu Ser Gln Gln
    390                 395                 400

act cat atg aaa att cag tca acg tta gac att tta aaa gag aaa act     1604
Thr His Met Lys Ile Gln Ser Thr Leu Asp Ile Leu Lys Glu Lys Thr
405                 410                 415                 420

aaa gag gct gag aga aca gct gaa ctg gct gag gct gat gct agg gaa     1652
Lys Glu Ala Glu Arg Thr Ala Glu Leu Ala Glu Ala Asp Ala Arg Glu
                425                 430                 435

aag gat aaa gaa tta gtt gag gct ctg aag agg tta aaa gat tat gaa     1700
Lys Asp Lys Glu Leu Val Glu Ala Leu Lys Arg Leu Lys Asp Tyr Glu
            440                 445                 450

tcg gga gta tat ggt tta gaa gat gct gtc gtt gaa ata aag aat tgt     1748
Ser Gly Val Tyr Gly Leu Glu Asp Ala Val Val Glu Ile Lys Asn Cys
        455                 460                 465

aaa aac caa att aaa ata aga gat cga gag att gaa ata tta aca aag     1796
Lys Asn Gln Ile Lys Ile Arg Asp Arg Glu Ile Glu Ile Leu Thr Lys
    470                 475                 480

gaa atc aat aaa ctt gaa ttg aag atc agt gat ttc ctt gat gaa aat     1844
Glu Ile Asn Lys Leu Glu Leu Lys Ile Ser Asp Phe Leu Asp Glu Asn
485                 490                 495                 500

gag gca ctt aga gag cgt gtg ggc ctt gaa cca aag aca atg att gat     1892
Glu Ala Leu Arg Glu Arg Val Gly Leu Glu Pro Lys Thr Met Ile Asp
                505                 510                 515

tta act gaa ttt aga aat agc aaa cac tta aaa cag cag cag tac aga     1940
Leu Thr Glu Phe Arg Asn Ser Lys His Leu Lys Gln Gln Gln Tyr Arg
            520                 525                 530

gct gaa aac cag att ctt ttg aaa gag att gaa agt cta gag gaa gaa     1988
Ala Glu Asn Gln Ile Leu Leu Lys Glu Ile Glu Ser Leu Glu Glu Glu
        535                 540                 545

cga ctt gat ctg aaa aaa aaa att cgt caa atg gct caa gaa aga gga     2036
Arg Leu Asp Leu Lys Lys Lys Ile Arg Gln Met Ala Gln Glu Arg Gly
    550                 555                 560

aaa aga agt gca act tca gga tta acc act gag gac ctg aac cta act     2084
Lys Arg Ser Ala Thr Ser Gly Leu Thr Thr Glu Asp Leu Asn Leu Thr
565                 570                 575                 580

gaa aac att tct caa gga gat aga ata agt gaa aga aaa ttg gat tta     2132
Glu Asn Ile Ser Gln Gly Asp Arg Ile Ser Glu Arg Lys Leu Asp Leu
                585                 590                 595

ttg agc ctc aaa aat atg agt gaa gca caa tca aag aat gaa ttt ctt     2180
Leu Ser Leu Lys Asn Met Ser Glu Ala Gln Ser Lys Asn Glu Phe Leu
            600                 605                 610

tca aga gaa cta att gaa aaa gaa aga gat tta gaa agg agt agg aca     2228
Ser Arg Glu Leu Ile Glu Lys Glu Arg Asp Leu Glu Arg Ser Arg Thr
        615                 620                 625

gtg ata gcc aaa ttt cag aat aaa tta aaa gaa tta gtt gaa gaa aat     2276
Val Ile Ala Lys Phe Gln Asn Lys Leu Lys Glu Leu Val Glu Glu Asn
    630                 635                 640

aag caa ctt gaa gaa ggt atg aaa gaa ata ttg caa gca att aag gaa     2324
Lys Gln Leu Glu Glu Gly Met Lys Glu Ile Leu Gln Ala Ile Lys Glu
645                 650                 655                 660

atg cag aaa gat cct gat gtt aaa gga gga gaa aca tct cta att atc     2372
Met Gln Lys Asp Pro Asp Val Lys Gly Gly Glu Thr Ser Leu Ile Ile
                665                 670                 675

cct agc ctt gaa aga cta gtt aat gct ata gaa tca aag aat gca gaa     2420
Pro Ser Leu Glu Arg Leu Val Asn Ala Ile Glu Ser Lys Asn Ala Glu
            680                 685                 690

gga atc ttt gat gcg agt ctg cat ttg aaa gcc caa gtt gat cag ctt     2468
Gly Ile Phe Asp Ala Ser Leu His Leu Lys Ala Gln Val Asp Gln Leu
```

-continued

```
        695                 700                 705

acc gga aga aat gaa gaa tta aga cag gag ctc agg gaa tct cgg aaa      2516
Thr Gly Arg Asn Glu Glu Leu Arg Gln Glu Leu Arg Glu Ser Arg Lys
    710                 715                 720

gag gct ata aat tat tca cag cag ttg gca aaa gct aat tta aag ata      2564
Glu Ala Ile Asn Tyr Ser Gln Gln Leu Ala Lys Ala Asn Leu Lys Ile
725                 730                 735                 740

gac cat ctt gaa aaa gaa act agt ctt tta cga caa tca gaa gga tcg      2612
Asp His Leu Glu Lys Glu Thr Ser Leu Leu Arg Gln Ser Glu Gly Ser
                745                 750                 755

aat gtt gtt ttt aaa gga att gac tta cct gat ggg ata gca cca tct      2660
Asn Val Val Phe Lys Gly Ile Asp Leu Pro Asp Gly Ile Ala Pro Ser
            760                 765                 770

agt gcc agt atc att aat tct cag aat gaa tat tta ata cat ttg tta      2708
Ser Ala Ser Ile Ile Asn Ser Gln Asn Glu Tyr Leu Ile His Leu Leu
        775                 780                 785

cag gaa cta gaa aat aaa gaa aaa aag tta aag aat tta gaa gat tct      2756
Gln Glu Leu Glu Asn Lys Glu Lys Lys Leu Lys Asn Leu Glu Asp Ser
    790                 795                 800

ctt gaa gat tac aac aga aaa ttt gct gta att cgt cat caa caa agt      2804
Leu Glu Asp Tyr Asn Arg Lys Phe Ala Val Ile Arg His Gln Gln Ser
805                 810                 815                 820

ttg ttg tat aaa gaa tac cta agt gaa aag gag acc tgg aaa aca gaa      2852
Leu Leu Tyr Lys Glu Tyr Leu Ser Glu Lys Glu Thr Trp Lys Thr Glu
                825                 830                 835

tct aaa aca ata aaa gag gaa aag aga aaa ctt gag gat caa gtc caa      2900
Ser Lys Thr Ile Lys Glu Glu Lys Arg Lys Leu Glu Asp Gln Val Gln
            840                 845                 850

caa gat gct ata aaa gta aaa gaa tat aat aat ttg ctc aat gct ctt      2948
Gln Asp Ala Ile Lys Val Lys Glu Tyr Asn Asn Leu Leu Asn Ala Leu
        855                 860                 865

cag atg gat tcg gat gaa atg aaa aaa ata ctt gca gaa aat agt agg      2996
Gln Met Asp Ser Asp Glu Met Lys Lys Ile Leu Ala Glu Asn Ser Arg
    870                 875                 880

aaa att act gtt ttg caa gtg aat gaa aaa tca ctt ata agg caa tat      3044
Lys Ile Thr Val Leu Gln Val Asn Glu Lys Ser Leu Ile Arg Gln Tyr
885                 890                 895                 900

aca acc tta gta gaa ttg gag cga caa ctt aga aaa gaa aat gag aag      3092
Thr Thr Leu Val Glu Leu Glu Arg Gln Leu Arg Lys Glu Asn Glu Lys
                905                 910                 915

caa aag aat gaa ttg ttg tca atg gag gct gaa gtt tgt gaa aaa att      3140
Gln Lys Asn Glu Leu Leu Ser Met Glu Ala Glu Val Cys Glu Lys Ile
            920                 925                 930

ggg tgt ttg caa aga ttt aag gaa atg gcc att ttc aag att gca gct      3188
Gly Cys Leu Gln Arg Phe Lys Glu Met Ala Ile Phe Lys Ile Ala Ala
        935                 940                 945

ctc caa aaa gtt gta gat aat agt gtt tct ttg tct gaa cta gaa ctg      3236
Leu Gln Lys Val Val Asp Asn Ser Val Ser Leu Ser Glu Leu Glu Leu
    950                 955                 960

gct aat aaa cag tac aat gaa ctg act gct aag tac agg gac atc ttg      3284
Ala Asn Lys Gln Tyr Asn Glu Leu Thr Ala Lys Tyr Arg Asp Ile Leu
965                 970                 975                 980

caa aaa gat aat atg ctt gtt caa aga aca agt aac ttg gaa cac ctg      3332
Gln Lys Asp Asn Met Leu Val Gln Arg Thr Ser Asn Leu Glu His Leu
                985                 990                 995

gag tgt gaa aac  atc tcc tta aaa gaa  caa gtg gag tct ata  aat       3377
Glu Cys Glu Asn  Ile Ser Leu Lys Glu  Gln Val Glu Ser Ile  Asn
            1000                 1005                 1010

aaa gaa ctg gag  att acc aag gaa aaa  ctt cac act att gaa  caa       3422
```

```
Lys Glu Leu Glu  Ile Thr Lys Glu Lys  Leu His Thr Ile Glu  Gln
            1015                1020                1025

gcc tgg gaa cag  gaa act aaa tta ggt  aat gaa tct agc atg  gat      3467
Ala Trp Glu Gln  Glu Thr Lys Leu Gly  Asn Glu Ser Ser Met  Asp
            1030                1035                1040

aag gca aag aaa  tca ata acc aac agt  gac att gtt tcc att  tca      3512
Lys Ala Lys Lys  Ser Ile Thr Asn Ser  Asp Ile Val Ser Ile  Ser
            1045                1050                1055

aaa aaa ata act  atg ctg gaa atg aag  gaa tta aat gaa agg  cag      3557
Lys Lys Ile Thr  Met Leu Glu Met Lys  Glu Leu Asn Glu Arg  Gln
            1060                1065                1070

cgg gct gaa cat  tgt caa aaa atg tat  gaa cac tta cgg act  tcg      3602
Arg Ala Glu His  Cys Gln Lys Met Tyr  Glu His Leu Arg Thr  Ser
            1075                1080                1085

tta aag caa atg  gag gaa cgt aat ttt  gaa ttg gaa acc aaa  ttt      3647
Leu Lys Gln Met  Glu Glu Arg Asn Phe  Glu Leu Glu Thr Lys  Phe
            1090                1095                1100

gct gag ctt acc  aaa atc aat ttg gat  gca cag aag gtg gaa  cag      3692
Ala Glu Leu Thr  Lys Ile Asn Leu Asp  Ala Gln Lys Val Glu  Gln
            1105                1110                1115

atg tta aga gat  gaa tta gct gat agt  gtg agc aag gca gta  agt      3737
Met Leu Arg Asp  Glu Leu Ala Asp Ser  Val Ser Lys Ala Val  Ser
            1120                1125                1130

gat gct gat agg  caa cgg att cta gaa  tta gag aag aat gaa  atg      3782
Asp Ala Asp Arg  Gln Arg Ile Leu Glu  Leu Glu Lys Asn Glu  Met
            1135                1140                1145

gaa cta aaa gtt  gaa gtg tca aaa ctg  aga gag att tct gat  att      3827
Glu Leu Lys Val  Glu Val Ser Lys Leu  Arg Glu Ile Ser Asp  Ile
            1150                1155                1160

gcc aga aga caa  gtt gaa att ttg aat  gca caa caa caa tct  agg      3872
Ala Arg Arg Gln  Val Glu Ile Leu Asn  Ala Gln Gln Gln Ser  Arg
            1165                1170                1175

gac aag gaa gta  gag tcc ctc aga atg  caa ctg cta gac tat  cag      3917
Asp Lys Glu Val  Glu Ser Leu Arg Met  Gln Leu Leu Asp Tyr  Gln
            1180                1185                1190

gca cag tct gat  gaa aag tcg ctc att  gcc aag ttg cac caa  cat      3962
Ala Gln Ser Asp  Glu Lys Ser Leu Ile  Ala Lys Leu His Gln  His
            1195                1200                1205

aat gtc tct ctt  caa ctg agt gag gct  act gct ctt ggt aag  ttg      4007
Asn Val Ser Leu  Gln Leu Ser Glu Ala  Thr Ala Leu Gly Lys  Leu
            1210                1215                1220

gag tca att aca  tct aaa ctg cag aag  atg gag gcc tac aac  ttg      4052
Glu Ser Ile Thr  Ser Lys Leu Gln Lys  Met Glu Ala Tyr Asn  Leu
            1225                1230                1235

cgc tta gag cag  aaa ctt gat gaa aaa  gaa cag gct ctc tat  tat      4097
Arg Leu Glu Gln  Lys Leu Asp Glu Lys  Glu Gln Ala Leu Tyr  Tyr
            1240                1245                1250

gct cgt ttg gag  gga aga aac aga gca  aaa cat ctg cgc caa  aca      4142
Ala Arg Leu Glu  Gly Arg Asn Arg Ala  Lys His Leu Arg Gln  Thr
            1255                1260                1265

att cag tct cta  cga cga cag ttt agt  gga gct tta ccc ttg  gca      4187
Ile Gln Ser Leu  Arg Arg Gln Phe Ser  Gly Ala Leu Pro Leu  Ala
            1270                1275                1280

caa cag gaa aag  ttc tcc aaa aca atg  att caa cta caa aat  gac      4232
Gln Gln Glu Lys  Phe Ser Lys Thr Met  Ile Gln Leu Gln Asn  Asp
            1285                1290                1295

aaa ctt aag ata  atg caa gaa atg aaa  aat tct caa caa gaa  cat      4277
Lys Leu Lys Ile  Met Gln Glu Met Lys  Asn Ser Gln Gln Glu  His
            1300                1305                1310
```

```
aga aat atg gag  aac aaa aca ttg gag  atg gaa tta aaa tta  aag      4322
Arg Asn Met Glu  Asn Lys Thr Leu Glu  Met Glu Leu Lys Leu  Lys
            1315                 1320                 1325

ggc ctg gaa gag  tta ata agc act tta  aag gat acc aaa gga  gcc      4367
Gly Leu Glu Glu  Leu Ile Ser Thr Leu  Lys Asp Thr Lys Gly  Ala
            1330                 1335                 1340

caa aag gta atc  aac tgg cat atg aaa  ata gaa gaa ctt cgt  ctt      4412
Gln Lys Val Ile  Asn Trp His Met Lys  Ile Glu Glu Leu Arg  Leu
            1345                 1350                 1355

caa gaa ctt aaa  cta aat cgg gaa tta  gtc aag gat aaa gaa  gaa      4457
Gln Glu Leu Lys  Leu Asn Arg Glu Leu  Val Lys Asp Lys Glu  Glu
            1360                 1365                 1370

ata aaa tat ttg  aat aac ata att tct  gaa tat gaa cgt aca  atc      4502
Ile Lys Tyr Leu  Asn Asn Ile Ile Ser  Glu Tyr Glu Arg Thr  Ile
            1375                 1380                 1385

agc agt ctt gaa  gaa gaa att gtg caa  cag aac aag ttt cat  gaa      4547
Ser Ser Leu Glu  Glu Glu Ile Val Gln  Gln Asn Lys Phe His  Glu
            1390                 1395                 1400

gaa aga caa atg  gcc tgg gat caa aga  gaa gtt gac ctg gaa  cgc      4592
Glu Arg Gln Met  Ala Trp Asp Gln Arg  Glu Val Asp Leu Glu  Arg
            1405                 1410                 1415

caa cta gac att  ttt gac cgt cag caa  aat gaa ata cta aat  gcg      4637
Gln Leu Asp Ile  Phe Asp Arg Gln Gln  Asn Glu Ile Leu Asn  Ala
            1420                 1425                 1430

gca caa aag ttt  gaa gaa gct aca gga  tca atc cct gac cct  agt      4682
Ala Gln Lys Phe  Glu Glu Ala Thr Gly  Ser Ile Pro Asp Pro  Ser
            1435                 1440                 1445

ttg ccc ctt cca  aat caa ctt gag atc  gct cta agg aaa att  aag      4727
Leu Pro Leu Pro  Asn Gln Leu Glu Ile  Ala Leu Arg Lys Ile  Lys
            1450                 1455                 1460

gag aac att cga  ata att cta gaa aca  cgg gca act tgc aaa  tca      4772
Glu Asn Ile Arg  Ile Ile Leu Glu Thr  Arg Ala Thr Cys Lys  Ser
            1465                 1470                 1475

cta gaa gag aaa  cta aaa gag aaa gaa  tct gct tta agg tta  gca      4817
Leu Glu Glu Lys  Leu Lys Glu Lys Glu  Ser Ala Leu Arg Leu  Ala
            1480                 1485                 1490

gaa caa aat ata  ctg tca aga gac aaa  gta atc aat gaa ctg  agg      4862
Glu Gln Asn Ile  Leu Ser Arg Asp Lys  Val Ile Asn Glu Leu  Arg
            1495                 1500                 1505

ctt cga ttg cct  gcc act gca gaa aga  gaa aag ctc ata gct  gag      4907
Leu Arg Leu Pro  Ala Thr Ala Glu Arg  Glu Lys Leu Ile Ala  Glu
            1510                 1515                 1520

cta ggc aga aaa  gag atg gaa cca aaa  tct cac cac aca ttg  aaa      4952
Leu Gly Arg Lys  Glu Met Glu Pro Lys  Ser His His Thr Leu  Lys
            1525                 1530                 1535

att gct cat caa  acc att gca aac atg  caa gca agg tta aat  caa      4997
Ile Ala His Gln  Thr Ile Ala Asn Met  Gln Ala Arg Leu Asn  Gln
            1540                 1545                 1550

aaa gaa gaa gta  tta aag aag tat caa  cgt ctt cta gaa aaa  gcc      5042
Lys Glu Glu Val  Leu Lys Lys Tyr Gln  Arg Leu Leu Glu Lys  Ala
            1555                 1560                 1565

aga gag gag caa  aga gaa att gtg aag  aaa cat gag gaa gac  ctt      5087
Arg Glu Glu Gln  Arg Glu Ile Val Lys  Lys His Glu Glu Asp  Leu
            1570                 1575                 1580

cat att ctt cat  cac aga tta gaa cta  cag gct gat agt tca  cta      5132
His Ile Leu His  His Arg Leu Glu Leu  Gln Ala Asp Ser Ser  Leu
            1585                 1590                 1595

aat aaa ttc aaa  caa acg gct tgg gat  tta atg aaa cag tct  ccc      5177
Asn Lys Phe Lys  Gln Thr Ala Trp Asp  Leu Met Lys Gln Ser  Pro
            1600                 1605                 1610
```

```
act cca gtt cct  acc aac aag cat ttt  att cgt ctg gct gag  atg      5222
Thr Pro Val Pro  Thr Asn Lys His Phe  Ile Arg Leu Ala Glu  Met
            1615                 1620                 1625

gaa cag aca gta  gca gaa caa gat gac  tct ctt tcc tca ctc  ttg      5267
Glu Gln Thr Val  Ala Glu Gln Asp Asp  Ser Leu Ser Ser Leu  Leu
            1630                 1635                 1640

gtc aaa cta aag  aaa gta tca caa gat  ttg gag aga caa aga  gaa      5312
Val Lys Leu Lys  Lys Val Ser Gln Asp  Leu Glu Arg Gln Arg  Glu
            1645                 1650                 1655

atc act gaa tta  aaa gta aaa gaa ttt  gaa aat atc aaa tta  cag      5357
Ile Thr Glu Leu  Lys Val Lys Glu Phe  Glu Asn Ile Lys Leu  Gln
            1660                 1665                 1670

ctt caa gaa aac  cat gaa gat gaa gtg  aaa aaa gta aaa gcg  gaa      5402
Leu Gln Glu Asn  His Glu Asp Glu Val  Lys Lys Val Lys Ala  Glu
            1675                 1680                 1685

gta gag gat tta  aag tat ctt ctg gac  cag tca caa aag gag  tca      5447
Val Glu Asp Leu  Lys Tyr Leu Leu Asp  Gln Ser Gln Lys Glu  Ser
            1690                 1695                 1700

cag tgt tta aaa  tct gaa ctt cag gct  caa aaa gaa gca aat  tca      5492
Gln Cys Leu Lys  Ser Glu Leu Gln Ala  Gln Lys Glu Ala Asn  Ser
            1705                 1710                 1715

aga gct cca aca  act aca atg aga aat  cta gta gaa cgg cta  aag      5537
Arg Ala Pro Thr  Thr Thr Met Arg Asn  Leu Val Glu Arg Leu  Lys
            1720                 1725                 1730

agc caa tta gcc  ttg aag gag aaa caa  cag aaa gca ctt agt  cgg      5582
Ser Gln Leu Ala  Leu Lys Glu Lys Gln  Gln Lys Ala Leu Ser  Arg
            1735                 1740                 1745

gca ctt tta gaa  ctc cgg gca gaa atg  aca gca gct gct gaa  gaa      5627
Ala Leu Leu Glu  Leu Arg Ala Glu Met  Thr Ala Ala Ala Glu  Glu
            1750                 1755                 1760

cgt att att tct  gca act tct caa aaa  gag gcc cat ctc aat  gtt      5672
Arg Ile Ile Ser  Ala Thr Ser Gln Lys  Glu Ala His Leu Asn  Val
            1765                 1770                 1775

caa caa atc gtt  gat cga cat act aga  gag cta aag aca caa  gtt      5717
Gln Gln Ile Val  Asp Arg His Thr Arg  Glu Leu Lys Thr Gln  Val
            1780                 1785                 1790

gaa gat tta aat  gaa aat ctt tta aaa  ttg aaa gaa gca ctt  aaa      5762
Glu Asp Leu Asn  Glu Asn Leu Leu Lys  Leu Lys Glu Ala Leu  Lys
            1795                 1800                 1805

aca agt aaa aac  aga gaa aac tca cta  act gat aat ttg aat  gac      5807
Thr Ser Lys Asn  Arg Glu Asn Ser Leu  Thr Asp Asn Leu Asn  Asp
            1810                 1815                 1820

tta aat aat gaa  ctg caa aag aaa caa  aaa gcc tat aat aaa  ata      5852
Leu Asn Asn Glu  Leu Gln Lys Lys Gln  Lys Ala Tyr Asn Lys  Ile
            1825                 1830                 1835

ctt aga gag aaa  gag gaa att gat caa  gag aat gat gaa ctg  aaa      5897
Leu Arg Glu Lys  Glu Glu Ile Asp Gln  Glu Asn Asp Glu Leu  Lys
            1840                 1845                 1850

agg caa att aaa  aga cta acc agt gga  tta cag ggc aaa ccc  ctg      5942
Arg Gln Ile Lys  Arg Leu Thr Ser Gly  Leu Gln Gly Lys Pro  Leu
            1855                 1860                 1865

aca gat aat aaa  caa agt cta att gaa  gaa ctc caa agg aaa  gtt      5987
Thr Asp Asn Lys  Gln Ser Leu Ile Glu  Glu Leu Gln Arg Lys  Val
            1870                 1875                 1880

aaa aaa cta gag  aac caa tta gag gga  aag gtg gag gaa gta  gac      6032
Lys Lys Leu Glu  Asn Gln Leu Glu Gly  Lys Val Glu Glu Val  Asp
            1885                 1890                 1895

cta aaa cct atg  aaa gaa aag aat gct  aaa gaa gaa tta att  agg      6077
Leu Lys Pro Met  Lys Glu Lys Asn Ala  Lys Glu Glu Leu Ile  Arg
```

```
            1900                1905                1910

tgg gaa gaa ggt  aaa aag tgg caa gcc  aaa ata gaa gga att  cga      6122
Trp Glu Glu Gly  Lys Lys Trp Gln Ala  Lys Ile Glu Gly Ile  Arg
            1915                1920                1925

aac aag tta aaa  gag aaa gag ggg gaa  gtc ttt act tta aca  aag      6167
Asn Lys Leu Lys  Glu Lys Glu Gly Glu  Val Phe Thr Leu Thr  Lys
            1930                1935                1940

cag ttg aat act  ttg aag gat ctt ttt  gcc aaa gcc gat aaa  gag      6212
Gln Leu Asn Thr  Leu Lys Asp Leu Phe  Ala Lys Ala Asp Lys  Glu
            1945                1950                1955

aaa ctt act ttg  cag agg aaa cta aaa  aca act ggc atg act  gtt      6257
Lys Leu Thr Leu  Gln Arg Lys Leu Lys  Thr Thr Gly Met Thr  Val
            1960                1965                1970

gat cag gtt ttg  gga ata cga gct ttg  gag tca gaa aaa gaa  ttg      6302
Asp Gln Val Leu  Gly Ile Arg Ala Leu  Glu Ser Glu Lys Glu  Leu
            1975                1980                1985

gaa gaa tta aaa  aag aga aat ctt gac  tta gaa aat gat ata  ttg      6347
Glu Glu Leu Lys  Lys Arg Asn Leu Asp  Leu Glu Asn Asp Ile  Leu
            1990                1995                2000

tat atg agg gcc  cac caa gct ctt cct  cga gat tct gtt gta  gaa      6392
Tyr Met Arg Ala  His Gln Ala Leu Pro  Arg Asp Ser Val Val  Glu
            2005                2010                2015

gat tta cat tta  caa aat aga tac ctc  caa gaa aaa ctt cat  gct      6437
Asp Leu His Leu  Gln Asn Arg Tyr Leu  Gln Glu Lys Leu His  Ala
            2020                2025                2030

tta gaa aaa cag  ttt tca aag gat aca  tat tct aag cct tca  att      6482
Leu Glu Lys Gln  Phe Ser Lys Asp Thr  Tyr Ser Lys Pro Ser  Ile
            2035                2040                2045

tca gga ata gag  tca gat gat cat tgt  cag aga gaa cag gag  ctt      6527
Ser Gly Ile Glu  Ser Asp Asp His Cys  Gln Arg Glu Gln Glu  Leu
            2050                2055                2060

cag aag gaa aac  ttg aag ttg tca tct  gaa aat att gaa ctg  aaa      6572
Gln Lys Glu Asn  Leu Lys Leu Ser Ser  Glu Asn Ile Glu Leu  Lys
            2065                2070                2075

ttt cag ctt gaa  caa gca aat aaa gat  ttg cca aga tta aag  aat      6617
Phe Gln Leu Glu  Gln Ala Asn Lys Asp  Leu Pro Arg Leu Lys  Asn
            2080                2085                2090

caa gtc aga gat  ttg aag gaa atg tgt  gaa ttt ctt aag aaa  gaa      6662
Gln Val Arg Asp  Leu Lys Glu Met Cys  Glu Phe Leu Lys Lys  Glu
            2095                2100                2105

aaa gca gaa gtt  cag cgg aaa ctt ggc  cat gtt aga ggg tct  ggt      6707
Lys Ala Glu Val  Gln Arg Lys Leu Gly  His Val Arg Gly Ser  Gly
            2110                2115                2120

aga agt gga aag  aca atc cca gaa ctg  gaa aaa acc att ggt  tta      6752
Arg Ser Gly Lys  Thr Ile Pro Glu Leu  Glu Lys Thr Ile Gly  Leu
            2125                2130                2135

atg aaa aaa gta  gtt gaa aaa gtc cag  aga gaa aat gaa cag  ttg      6797
Met Lys Lys Val  Val Glu Lys Val Gln  Arg Glu Asn Glu Gln  Leu
            2140                2145                2150

aaa aaa gca tca  gga ata ttg act agt  gaa aaa atg gct aat  att      6842
Lys Lys Ala Ser  Gly Ile Leu Thr Ser  Glu Lys Met Ala Asn  Ile
            2155                2160                2165

gag cag gaa aat  gaa aaa ttg aag gct  gaa tta gaa aaa ctt  aaa      6887
Glu Gln Glu Asn  Glu Lys Leu Lys Ala  Glu Leu Glu Lys Leu  Lys
            2170                2175                2180

gct cat ctt ggg  cat cag ttg agc atg  cac tat gaa tcc aag  acc      6932
Ala His Leu Gly  His Gln Leu Ser Met  His Tyr Glu Ser Lys  Thr
            2185                2190                2195

aaa ggc aca gaa  aaa att att gct gaa  aat gaa agg ctt cgt  aaa      6977
```

```
Lys Gly Thr Glu  Lys Ile Ile Ala Glu  Asn Glu Arg Leu Arg  Lys
            2200                 2205                 2210

gaa ctt aaa aaa  gaa act gat gct gca  gag aaa tta cgg ata  gca      7022
Glu Leu Lys Lys  Glu Thr Asp Ala Ala  Glu Lys Leu Arg Ile  Ala
            2215                 2220                 2225

aag aat aat tta  gag ata tta aat gag  aag atg aca gtt caa  cta      7067
Lys Asn Asn Leu  Glu Ile Leu Asn Glu  Lys Met Thr Val Gln  Leu
            2230                 2235                 2240

gaa gag act ggt  aag aga ttg cag ttt  gca gaa agc aga ggt  cca      7112
Glu Glu Thr Gly  Lys Arg Leu Gln Phe  Ala Glu Ser Arg Gly  Pro
            2245                 2250                 2255

cag ctt gaa ggt  gct gac agt aag agc  tgg aaa tcc att gtg  gtt      7157
Gln Leu Glu Gly  Ala Asp Ser Lys Ser  Trp Lys Ser Ile Val  Val
            2260                 2265                 2270

aca aga atg tat  gaa acc aag tta aaa  gaa ttg gaa act gat  att      7202
Thr Arg Met Tyr  Glu Thr Lys Leu Lys  Glu Leu Glu Thr Asp  Ile
            2275                 2280                 2285

gcc aaa aaa aat  caa agc att act gac  ctt aaa cag ctt gta  aaa      7247
Ala Lys Lys Asn  Gln Ser Ile Thr Asp  Leu Lys Gln Leu Val  Lys
            2290                 2295                 2300

gaa gca aca gag  aga gaa caa aaa gtt  aac aaa tac aat gaa  gac      7292
Glu Ala Thr Glu  Arg Glu Gln Lys Val  Asn Lys Tyr Asn Glu  Asp
            2305                 2310                 2315

ctt gaa caa cag  att aag att ctt aaa  cat gtt cct gaa ggt  gct      7337
Leu Glu Gln Gln  Ile Lys Ile Leu Lys  His Val Pro Glu Gly  Ala
            2320                 2325                 2330

gag aca gag caa  ggc ctt aaa cgg gag  ctt caa gtt ctt aga  tta      7382
Glu Thr Glu Gln  Gly Leu Lys Arg Glu  Leu Gln Val Leu Arg  Leu
            2335                 2340                 2345

gct aat cat cag  ctg gat aaa gag aaa  gca gaa tta atc cat  cag      7427
Ala Asn His Gln  Leu Asp Lys Glu Lys  Ala Glu Leu Ile His  Gln
            2350                 2355                 2360

ata gaa gct aac  aag gac caa agt gga  gct gaa agc acc ata  cct      7472
Ile Glu Ala Asn  Lys Asp Gln Ser Gly  Ala Glu Ser Thr Ile  Pro
            2365                 2370                 2375

gat gct gat caa  cta aag gaa aaa ata  aaa gat cta gag aca  cag      7517
Asp Ala Asp Gln  Leu Lys Glu Lys Ile  Lys Asp Leu Glu Thr  Gln
            2380                 2385                 2390

ctc aaa atg tca  gat cta gaa aag cag  cat ttg aag gag gaa  ata      7562
Leu Lys Met Ser  Asp Leu Glu Lys Gln  His Leu Lys Glu Glu  Ile
            2395                 2400                 2405

aag aag ctg aaa  aaa gaa ctg gaa aat  ttt gat cct tca ttt  ttt      7607
Lys Lys Leu Lys  Lys Glu Leu Glu Asn  Phe Asp Pro Ser Phe  Phe
            2410                 2415                 2420

gaa gaa att gaa  gat ctt aag tat aat  tac aag gaa gaa gtg  aag      7652
Glu Glu Ile Glu  Asp Leu Lys Tyr Asn  Tyr Lys Glu Glu Val  Lys
            2425                 2430                 2435

aag aat att ctc  tta gaa gag aag gta  aaa aaa ctt tca gaa  caa      7697
Lys Asn Ile Leu  Leu Glu Glu Lys Val  Lys Lys Leu Ser Glu  Gln
            2440                 2445                 2450

ttg gga gtt gaa  tta act agc cct gtt  gct gct tct gaa gag  ttt     7742
Leu Gly Val Glu  Leu Thr Ser Pro Val  Ala Ala Ser Glu Glu  Phe
            2455                 2460                 2465

gaa gat gaa gaa  gaa agt cct gtt aat  ttc ccc att tac taaaggtcac    7791
Glu Asp Glu Glu  Glu Ser Pro Val Asn  Phe Pro Ile Tyr
            2470                 2475

ctataaactt tgtttcattt aactatttat taactttata agttaaatat acttggaaat   7851

aagcagttct ccgaactgta gtatttcctt ctcactacct tgtaccttta tacttagatt   7911
```

```
ggaattctta ataaataaaa ttatatgaaa ttttcaactt attaaaaaaa aaaaaaaaaa   7971

a                                                                   7972


<210> SEQ ID NO 3
<211> LENGTH: 2479
<212> TYPE: PRT
<213> ORGANISM: Homo sapiens

<400> SEQUENCE: 3

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
```

```
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780
```

```
Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu Cys Glu Asn  Ile Ser Leu Lys Glu  Gln Val Glu
        995                 1000                1005

Ser Ile  Asn Lys Glu Leu Glu  Ile Thr Lys Glu Lys  Leu His Thr
    1010                1015                1020

Ile Glu  Gln Ala Trp Glu Gln  Glu Thr Lys Leu Gly  Asn Glu Ser
    1025                1030                1035

Ser Met  Asp Lys Ala Lys Lys  Ser Ile Thr Asn Ser  Asp Ile Val
    1040                1045                1050

Ser Ile  Ser Lys Lys Ile Thr  Met Leu Glu Met Lys  Glu Leu Asn
    1055                1060                1065

Glu Arg  Gln Arg Ala Glu His  Cys Gln Lys Met Tyr  Glu His Leu
    1070                1075                1080

Arg Thr  Ser Leu Lys Gln Met  Glu Glu Arg Asn Phe  Glu Leu Glu
    1085                1090                1095

Thr Lys  Phe Ala Glu Leu Thr  Lys Ile Asn Leu Asp  Ala Gln Lys
    1100                1105                1110

Val Glu  Gln Met Leu Arg Asp  Glu Leu Ala Asp Ser  Val Ser Lys
    1115                1120                1125

Ala Val  Ser Asp Ala Asp Arg  Gln Arg Ile Leu Glu  Leu Glu Lys
    1130                1135                1140

Asn Glu  Met Glu Leu Lys Val  Glu Val Ser Lys Leu  Arg Glu Ile
    1145                1150                1155

Ser Asp  Ile Ala Arg Arg Gln  Val Glu Ile Leu Asn  Ala Gln Gln
    1160                1165                1170

Gln Ser  Arg Asp Lys Glu Val  Glu Ser Leu Arg Met  Gln Leu Leu
    1175                1180                1185
```

```
Asp Tyr  Gln Ala Gln Ser Asp  Glu Lys Ser Leu Ile  Ala Lys Leu
    1190                 1195                 1200

His Gln  His Asn Val Ser Leu  Gln Leu Ser Glu Ala  Thr Ala Leu
    1205                 1210                 1215

Gly Lys  Leu Glu Ser Ile Thr  Ser Lys Leu Gln Lys  Met Glu Ala
    1220                 1225                 1230

Tyr Asn  Leu Arg Leu Glu Gln  Lys Leu Asp Glu Lys  Glu Gln Ala
    1235                 1240                 1245

Leu Tyr  Tyr Ala Arg Leu Glu  Gly Arg Asn Arg Ala  Lys His Leu
    1250                 1255                 1260

Arg Gln  Thr Ile Gln Ser Leu  Arg Arg Gln Phe Ser  Gly Ala Leu
    1265                 1270                 1275

Pro Leu  Ala Gln Gln Glu Lys  Phe Ser Lys Thr Met  Ile Gln Leu
    1280                 1285                 1290

Gln Asn  Asp Lys Leu Lys Ile  Met Gln Glu Met Lys  Asn Ser Gln
    1295                 1300                 1305

Gln Glu  His Arg Asn Met Glu  Asn Lys Thr Leu Glu  Met Glu Leu
    1310                 1315                 1320

Lys Leu  Lys Gly Leu Glu Glu  Leu Ile Ser Thr Leu  Lys Asp Thr
    1325                 1330                 1335

Lys Gly  Ala Gln Lys Val Ile  Asn Trp His Met Lys  Ile Glu Glu
    1340                 1345                 1350

Leu Arg  Leu Gln Glu Leu Lys  Leu Asn Arg Glu Leu  Val Lys Asp
    1355                 1360                 1365

Lys Glu  Glu Ile Lys Tyr Leu  Asn Asn Ile Ile Ser  Glu Tyr Glu
    1370                 1375                 1380

Arg Thr  Ile Ser Ser Leu Glu  Glu Glu Ile Val Gln  Gln Asn Lys
    1385                 1390                 1395

Phe His  Glu Glu Arg Gln Met  Ala Trp Asp Gln Arg  Glu Val Asp
    1400                 1405                 1410

Leu Glu  Arg Gln Leu Asp Ile  Phe Asp Arg Gln Gln  Asn Glu Ile
    1415                 1420                 1425

Leu Asn  Ala Ala Gln Lys Phe  Glu Glu Ala Thr Gly  Ser Ile Pro
    1430                 1435                 1440

Asp Pro  Ser Leu Pro Leu Pro  Asn Gln Leu Glu Ile  Ala Leu Arg
    1445                 1450                 1455

Lys Ile  Lys Glu Asn Ile Arg  Ile Ile Leu Glu Thr  Arg Ala Thr
    1460                 1465                 1470

Cys Lys  Ser Leu Glu Glu Lys  Leu Lys Glu Lys Glu  Ser Ala Leu
    1475                 1480                 1485

Arg Leu  Ala Glu Gln Asn Ile  Leu Ser Arg Asp Lys  Val Ile Asn
    1490                 1495                 1500

Glu Leu  Arg Leu Arg Leu Pro  Ala Thr Ala Glu Arg  Glu Lys Leu
    1505                 1510                 1515

Ile Ala  Glu Leu Gly Arg Lys  Glu Met Glu Pro Lys  Ser His His
    1520                 1525                 1530

Thr Leu  Lys Ile Ala His Gln  Thr Ile Ala Asn Met  Gln Ala Arg
    1535                 1540                 1545

Leu Asn  Gln Lys Glu Glu Val  Leu Lys Lys Tyr Gln  Arg Leu Leu
    1550                 1555                 1560

Glu Lys  Ala Arg Glu Glu Gln  Arg Glu Ile Val Lys  Lys His Glu
    1565                 1570                 1575

Glu Asp  Leu His Ile Leu His  His Arg Leu Glu Leu  Gln Ala Asp
```

```
    1580                1585                1590

Ser Ser  Leu Asn Lys Phe Lys  Gln Thr Ala Trp Asp  Leu Met Lys
    1595                1600                1605

Gln Ser  Pro Thr Pro Val Pro  Thr Asn Lys His Phe  Ile Arg Leu
    1610                1615                1620

Ala Glu  Met Glu Gln Thr Val  Ala Glu Gln Asp Asp  Ser Leu Ser
    1625                1630                1635

Ser Leu  Leu Val Lys Leu Lys  Lys Val Ser Gln Asp  Leu Glu Arg
    1640                1645                1650

Gln Arg  Glu Ile Thr Glu Leu  Lys Val Lys Glu Phe  Glu Asn Ile
    1655                1660                1665

Lys Leu  Gln Leu Gln Glu Asn  His Glu Asp Glu Val  Lys Lys Val
    1670                1675                1680

Lys Ala  Glu Val Glu Asp Leu  Lys Tyr Leu Leu Asp  Gln Ser Gln
    1685                1690                1695

Lys Glu  Ser Gln Cys Leu Lys  Ser Glu Leu Gln Ala  Gln Lys Glu
    1700                1705                1710

Ala Asn  Ser Arg Ala Pro Thr  Thr Thr Met Arg Asn  Leu Val Glu
    1715                1720                1725

Arg Leu  Lys Ser Gln Leu Ala  Leu Lys Glu Lys Gln  Gln Lys Ala
    1730                1735                1740

Leu Ser  Arg Ala Leu Leu Glu  Leu Arg Ala Glu Met  Thr Ala Ala
    1745                1750                1755

Ala Glu  Glu Arg Ile Ile Ser  Ala Thr Ser Gln Lys  Glu Ala His
    1760                1765                1770

Leu Asn  Val Gln Gln Ile Val  Asp Arg His Thr Arg  Glu Leu Lys
    1775                1780                1785

Thr Gln  Val Glu Asp Leu Asn  Glu Asn Leu Leu Lys  Leu Lys Glu
    1790                1795                1800

Ala Leu  Lys Thr Ser Lys Asn  Arg Glu Asn Ser Leu  Thr Asp Asn
    1805                1810                1815

Leu Asn  Asp Leu Asn Asn Glu  Leu Gln Lys Lys Gln  Lys Ala Tyr
    1820                1825                1830

Asn Lys  Ile Leu Arg Glu Lys  Glu Glu Ile Asp Gln  Glu Asn Asp
    1835                1840                1845

Glu Leu  Lys Arg Gln Ile Lys  Arg Leu Thr Ser Gly  Leu Gln Gly
    1850                1855                1860

Lys Pro  Leu Thr Asp Asn Lys  Gln Ser Leu Ile Glu  Glu Leu Gln
    1865                1870                1875

Arg Lys  Val Lys Lys Leu Glu  Asn Gln Leu Glu Gly  Lys Val Glu
    1880                1885                1890

Glu Val  Asp Leu Lys Pro Met  Lys Glu Lys Asn Ala  Lys Glu Glu
    1895                1900                1905

Leu Ile  Arg Trp Glu Glu Gly  Lys Lys Trp Gln Ala  Lys Ile Glu
    1910                1915                1920

Gly Ile  Arg Asn Lys Leu Lys  Glu Lys Glu Gly Glu  Val Phe Thr
    1925                1930                1935

Leu Thr  Lys Gln Leu Asn Thr  Leu Lys Asp Leu Phe  Ala Lys Ala
    1940                1945                1950

Asp Lys  Glu Lys Leu Thr Leu  Gln Arg Lys Leu Lys  Thr Thr Gly
    1955                1960                1965

Met Thr  Val Asp Gln Val Leu  Gly Ile Arg Ala Leu  Glu Ser Glu
    1970                1975                1980
```

```
Lys Glu  Leu Glu Glu Leu Lys  Lys Arg Asn Leu Asp  Leu Glu Asn
    1985                 1990                 1995

Asp Ile  Leu Tyr Met Arg Ala  His Gln Ala Leu Pro  Arg Asp Ser
    2000                 2005                 2010

Val Val  Glu Asp Leu His Leu  Gln Asn Arg Tyr Leu  Gln Glu Lys
    2015                 2020                 2025

Leu His  Ala Leu Glu Lys Gln  Phe Ser Lys Asp Thr  Tyr Ser Lys
    2030                 2035                 2040

Pro Ser  Ile Ser Gly Ile Glu  Ser Asp Asp His Cys  Gln Arg Glu
    2045                 2050                 2055

Gln Glu  Leu Gln Lys Glu Asn  Leu Lys Leu Ser Ser  Glu Asn Ile
    2060                 2065                 2070

Glu Leu  Lys Phe Gln Leu Glu  Gln Ala Asn Lys Asp  Leu Pro Arg
    2075                 2080                 2085

Leu Lys  Asn Gln Val Arg Asp  Leu Lys Glu Met Cys  Glu Phe Leu
    2090                 2095                 2100

Lys Lys  Glu Lys Ala Glu Val  Gln Arg Lys Leu Gly  His Val Arg
    2105                 2110                 2115

Gly Ser  Gly Arg Ser Gly Lys  Thr Ile Pro Glu Leu  Glu Lys Thr
    2120                 2125                 2130

Ile Gly  Leu Met Lys Lys Val  Val Glu Lys Val Gln  Arg Glu Asn
    2135                 2140                 2145

Glu Gln  Leu Lys Lys Ala Ser  Gly Ile Leu Thr Ser  Glu Lys Met
    2150                 2155                 2160

Ala Asn  Ile Glu Gln Glu Asn  Glu Lys Leu Lys Ala  Glu Leu Glu
    2165                 2170                 2175

Lys Leu  Lys Ala His Leu Gly  His Gln Leu Ser Met  His Tyr Glu
    2180                 2185                 2190

Ser Lys  Thr Lys Gly Thr Glu  Lys Ile Ile Ala Glu  Asn Glu Arg
    2195                 2200                 2205

Leu Arg  Lys Glu Leu Lys Lys  Glu Thr Asp Ala Ala  Glu Lys Leu
    2210                 2215                 2220

Arg Ile  Ala Lys Asn Asn Leu  Glu Ile Leu Asn Glu  Lys Met Thr
    2225                 2230                 2235

Val Gln  Leu Glu Glu Thr Gly  Lys Arg Leu Gln Phe  Ala Glu Ser
    2240                 2245                 2250

Arg Gly  Pro Gln Leu Glu Gly  Ala Asp Ser Lys Ser  Trp Lys Ser
    2255                 2260                 2265

Ile Val  Val Thr Arg Met Tyr  Glu Thr Lys Leu Lys  Glu Leu Glu
    2270                 2275                 2280

Thr Asp  Ile Ala Lys Lys Asn  Gln Ser Ile Thr Asp  Leu Lys Gln
    2285                 2290                 2295

Leu Val  Lys Glu Ala Thr Glu  Arg Glu Gln Lys Val  Asn Lys Tyr
    2300                 2305                 2310

Asn Glu  Asp Leu Glu Gln Gln  Ile Lys Ile Leu Lys  His Val Pro
    2315                 2320                 2325

Glu Gly  Ala Glu Thr Glu Gln  Gly Leu Lys Arg Glu  Leu Gln Val
    2330                 2335                 2340

Leu Arg  Leu Ala Asn His Gln  Leu Asp Lys Glu Lys  Ala Glu Leu
    2345                 2350                 2355

Ile His  Gln Ile Glu Ala Asn  Lys Asp Gln Ser Gly  Ala Glu Ser
    2360                 2365                 2370
```

```
Thr Ile  Pro Asp Ala Asp Gln  Leu Lys Glu Lys Ile  Lys Asp Leu
    2375                 2380                 2385

Glu Thr  Gln Leu Lys Met Ser  Asp Leu Glu Lys Gln  His Leu Lys
    2390                 2395                 2400

Glu Glu  Ile Lys Lys Leu Lys  Lys Glu Leu Glu Asn  Phe Asp Pro
    2405                 2410                 2415

Ser Phe  Phe Glu Glu Ile Glu  Asp Leu Lys Tyr Asn  Tyr Lys Glu
    2420                 2425                 2430

Glu Val  Lys Lys Asn Ile Leu  Leu Glu Glu Lys Val  Lys Lys Leu
    2435                 2440                 2445

Ser Glu  Gln Leu Gly Val Glu  Leu Thr Ser Pro Val  Ala Ala Ser
    2450                 2455                 2460

Glu Glu  Phe Glu Asp Glu Glu  Glu Ser Pro Val Asn  Phe Pro Ile
    2465                 2470                 2475

Tyr


<210> SEQ ID NO 4
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: 128 nucleotide aberrant CEO290 exon

<400> SEQUENCE: 4

tagagatggg gtttcacctt gttagccagg atggtgtcga tctcctgaac tcgtgatcca     60

cccgcctcgg cctcctaaag tgctgggatt acagatgtga gccaccgcac ctggccccag    120

ttgtaatt                                                             128


<210> SEQ ID NO 5
<211> LENGTH: 997
<212> TYPE: PRT
<213> ORGANISM: Homo sapiens
<220> FEATURE:
<221> NAME/KEY: misc_feature
<222> LOCATION: (1)..(997)
<223> OTHER INFORMATION: Aberrant CEP290 polypeptide

<400> SEQUENCE: 5

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140
```

```
Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285

Thr Asp Leu Leu Lys Ser Lys Asn Glu Glu Asp Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                325                 330                 335

Lys Leu Lys Asn Ala Gln Leu Asp Ala Asp Lys Ser Asn Val Met Ala
            340                 345                 350

Leu Gln Gln Gly Ile Gln Glu Arg Asp Ser Gln Ile Lys Met Leu Thr
        355                 360                 365

Glu Gln Val Glu Gln Tyr Thr Lys Glu Met Glu Lys Asn Thr Cys Ile
    370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
        515                 520                 525

Gln Gln Tyr Arg Ala Glu Asn Gln Ile Leu Leu Lys Glu Ile Glu Ser
    530                 535                 540

Leu Glu Glu Glu Arg Leu Asp Leu Lys Lys Lys Ile Arg Gln Met Ala
545                 550                 555                 560
```

```
Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
        595                 600                 605

Asn Glu Phe Leu Ser Arg Glu Leu Ile Glu Lys Glu Arg Asp Leu Glu
    610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
        755                 760                 765

Ile Ala Pro Ser Ser Ala Ser Ile Ile Asn Ser Gln Asn Glu Tyr Leu
    770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
        835                 840                 845

Asp Gln Val Gln Gln Asp Ala Ile Lys Val Lys Glu Tyr Asn Asn Leu
    850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910

Glu Asn Glu Lys Gln Lys Asn Glu Leu Leu Ser Met Glu Ala Glu Val
        915                 920                 925

Cys Glu Lys Ile Gly Cys Leu Gln Arg Phe Lys Glu Met Ala Ile Phe
    930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975
```

```
Arg Asp Ile Leu Gln Lys Asp Asn Met Leu Val Gln Arg Thr Ser Asn
            980                 985                 990

Leu Glu His Leu Glu
        995


<210> SEQ ID NO 6
<211> LENGTH: 143
<212> TYPE: DNA
<213> ORGANISM: Homo sapiens
<220> FEATURE:
<221> NAME/KEY: misc_feature
<222> LOCATION: (1)..(143)
<223> OTHER INFORMATION: 143 nucleotide motif

<400> SEQUENCE: 6

tagagatggg gtttcacctt gttagccagg atggtgtcga tctcctgaac tcgtgatcca      60

cccgcctcgg cctcctaaag tgctgggatt acagatgtga gccaccgcac ctggccccag     120

ttgtaattgt gaatatctca tac                                             143


<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: 42 nucleotide motif

<400> SEQUENCE: 7

acagatgtga gccaccgcac ctggccccag ttgtaattgt ga                         42


<210> SEQ ID NO 8
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 24 nucleotide motif

<400> SEQUENCE: 8

ccaccgcacc tggccccagt tgta                                             24


<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-1

<400> SEQUENCE: 9

taatcccagc actttaggag                                                  20


<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-2
```

<400> SEQUENCE: 10
gggccaggtg cggtgg 16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AON-3

<400> SEQUENCE: 11
aactggggcc aggtgcg 17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AON-4

<400> SEQUENCE: 12
tacaactggg gccaggtg 18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: AON-5

<400> SEQUENCE: 13
actcacaatt acaactgggg 20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: SON-3

<400> SEQUENCE: 14
cgcacctggc cccagtt 17

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic PCR primer

<400> SEQUENCE: 15
tgctaagtac agggacatct tgc 23

-continued

```
<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16

agactccact tgttctttta aggag                                           25


<210> SEQ ID NO 17
<211> LENGTH: 36
<212> TYPE: DNA
<213> ORGANISM: Homo sapiens

<400> SEQUENCE: 17

cacctggccc cagttgtaat tgtgaatatc tcatac                               36


<210> SEQ ID NO 18
<211> LENGTH: 36
<212> TYPE: RNA
<213> ORGANISM: Homo sapiens

<400> SEQUENCE: 18

caccuggccc caguuguaau ugugaauauc ucauac                               36


<210> SEQ ID NO 19
<211> LENGTH: 36
<212> TYPE: DNA
<213> ORGANISM: Homo sapiens

<400> SEQUENCE: 19

cacctggccc cagttgtaat tgtgagtatc tcatac                               36


<210> SEQ ID NO 20
<211> LENGTH: 36
<212> TYPE: RNA
<213> ORGANISM: Homo sapiens

<400> SEQUENCE: 20

caccuggccc caguuguaau ugugaguauc ucauac                               36


<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

auacuacuaa uuacaacugg g                                               21
```